US008088897B2

(12) United States Patent
Lowery et al.

(10) Patent No.: US 8,088,897 B2
(45) Date of Patent: Jan. 3, 2012

(54) ASSAY METHOD FOR GROUP TRANSFER REACTIONS

(75) Inventors: Robert Lowery, Belleville, WI (US); Karen Kleman-Leyer, Madison, WI (US); Matt Staeben, Belleville, WI (US); Thane Westermeyer, Sun Prairie, WI (US)

(73) Assignee: BellBrook Labs, Inc., Madison, WI (US)

( * ) Notice: Subject to any disclaimer, the term of this patent is extended or adjusted under 35 U.S.C. 154(b) by 0 days.

(21) Appl. No.: 12/109,628

(22) Filed: Apr. 25, 2008

(65) Prior Publication Data

US 2008/0233592 A1   Sep. 25, 2008

Related U.S. Application Data

(63) Continuation-in-part of application No. 11/353,500, filed on Feb. 14, 2006, now Pat. No. 7,378,505, which is a continuation-in-part of application No. 10/769,578, filed on Jan. 30, 2004, now Pat. No. 7,332,278.

(60) Provisional application No. 60/443,746, filed on Jan. 30, 2003.

(51) Int. Cl.
*C07K 16/44* (2006.01)
(52) U.S. Cl. ............. 530/387.1; 530/388.21; 530/389.1; 530/389.8
(58) Field of Classification Search ........................ None
See application file for complete search history.

(56) References Cited

U.S. PATENT DOCUMENTS

| | | | |
|---|---|---|---|
| 4,208,479 A * | 6/1980 | Zuk et al. ........................ 435/7.9 |
| 5,723,591 A | 3/1998 | Livak et al. | |
| 5,779,868 A | 7/1998 | Parce et al. | |
| 5,858,195 A | 1/1999 | Ramsey | |
| 5,942,443 A | 8/1999 | Parce et al. | |
| 5,958,717 A | 9/1999 | Sundrehagen | |
| 6,461,829 B1 | 10/2002 | Kahne | |
| 6,551,790 B2 | 4/2003 | Trubetskoy et al. | |
| 6,599,711 B2 | 7/2003 | Crouch et al. | |
| 7,332,278 B2 | 2/2008 | Lowery et al. | |
| 7,355,010 B2 | 4/2008 | Lowery et al. | |
| 7,378,505 B2 | 5/2008 | Lowery et al. | |
| 2002/0197606 A1 | 12/2002 | Craig | |
| 2004/0018515 A1 | 1/2004 | Diener et al. | |
| 2008/0132684 A1 | 6/2008 | Lowery et al. | |
| 2008/0233592 A1 | 9/2008 | Lowery et al. | |
| 2008/0255341 A2 | 10/2008 | Lowery et al. | |

FOREIGN PATENT DOCUMENTS

WO   9846438        10/1998
WO   2004027421 A2  4/2004

OTHER PUBLICATIONS

Vincent et al. Tetrahedron Letters, 1998 vol. 39, p. 2321-2324.*
Muller et al. cancer reasearch, 1980, vol. 40, p. 887-896.*
Allen, M. et al., "A Homogenous High Throughput Nonradioactive Method for Measurement of Functional . . . ," Journal of Biomolecular Screening (2002) 7:35-44.
Bredehorst, R., et al., "Production of Antibodies Against ADP-ribose and 5'-AMP with the Aid of N6-Carboxymethlated ADP-ribose . . . ," Eur. J. Biochem., (1978) 82:105-113.
Burkhart et al., "A Continuous Assay for the Spectrophotometric Analysis of Sulfotransferases Using Aryl Sulfotransferase IV," Analytical Biochemistry (1999) 274:131-137.
Debonis, Salvatore, et al., "In vitro Screening for Inhibitors of the Human Miotic Kinesin Eg5 with Antimitotic and Antiumor Activities," Mol Cancer Ther. (2004) 3:1079-1090.
Donnelly, J. G., et al., "Evaluation of the Abbott IMxTM Fluorescence Polarization Immunoassay and the Bio-Rad Enzyme . . . ," Ann Clin Biochem (2000) 37:194-198.
Ethel et al., "A Universal Radiochemical High-Performance Liquid Chromatographic Assay for the Determination of UDP-Glucuronosyltransferase Activity," Analytical Biochemistry (1998) 255:142-147.
Giovane et al., "1-N6-Etheno-ADP-ribosylation of elongation facto-2 by Diptheria Toxin," FEBS 3023 Oct. 1985, vol. 191, No. 299:191-194.
Glassler et al., "Bag-1M Accelerates Nucleotide Release for Human Hsc70 and Hsp7 and Can Act Concentration-dependent as Positive and Negative Cofactor," The Journal of Biological Chemistry (2001) 276(35):32538-32544.
Kawamitsu et al., "Monoclonal Antibodies to Poly(Adenosine Diphosphate Ribose) Recognize Different Structures," Biochemistry (1984) 23(16):3771-3777.
Kouri et al., "2,3,7,8-Tetrachlorodibeno-p-dioxin as Cocarcinogen Causing 3-Methylcholanthrene-initiated Subcutaneous Tumors in Mice Genetically Nonresponsive to *Ah locus*," Cancer Research (1978) 38:2777-2783.
Li et al., "An Ultra-High Throughput Screening Approach for an Adenine Transferase Using Fluorescence Polarization," Journal of Biomolecular Screening (2000) 5:31-37.
Meyer T., et al., "Production of anti-(ADP-ribose) Antibodies with the Aid of Dinucleotide-pyrophosphatase-resistant Hapten and Their Application for the Detection of Mono(ADP-ribosyl)ated Polypeptides," Eur. J. Biochem., (1986) 155:157-165.
Mulder et al., "Rapid NAD+—Linked Assay for Microsomal Uridine Diphosphate Glucuronyltransferase of Rat Liver and Some Observations of Substrate Specificity of the Enzyme," Biochem J. (1975) 151:131-140.
Otterness et al., "3' Phosphoadnosine 5' -Phosphosulfate: Photoaffinity Ligand for Sulfotransferase Enzymes," American Society for Pharmacology and Experimental Therapeutics (1991) 39(1):34-41.
Parker et al., "Development of High Throughput Screening Assays Using Fluroescence Polarization: Nuclear Receptor Ligand . . . ," J of Biomolecular Screening (2000) 5:77-88.

(Continued)

*Primary Examiner* — Yunsoo Kim
(74) *Attorney, Agent, or Firm* — Quarles & Brady LLP; Sara D. Vinarov

(57) ABSTRACT

An isolated antibody produced against a donor product of an enzymatically catalyzed group transfer reaction is disclosed. In one aspect, the antibody has the ability to preferentially recognize the donor-product guanosine diphosphate (GDP), in the presence of the donor molecule guanosine triphosphate (GTP). Immunuoassays using compositions including such antibodies and kits for performing the immunoassays are also disclosed.

11 Claims, 28 Drawing Sheets

OTHER PUBLICATIONS

Patton, Review, "Detection Technologies in Proteome Analysis," Journal of Chromatography B (2002) 771:3-31.

Seethala, R., et al., "A Fluorescence Polarization Competition Immunoassay for Tryosine Kinases," Analytical Biochemistry (1998) 255:257-262.

Seethala, "Fluorescence Polarization Competition Immunoassay for Tyrosine Kinases," Methods (2000) 22:61-70.

Sills et al., "Comparison of Assay Technologies for Tryosine Kinase Assay Generates Different Results in High Throughput Screening," Journal of Biomolecular Screening (2002) 7:191-214.

Walters et al, "Designing Screens: How to Make Your Hits a Hit," Nature Reviews (2003) 2:259-266.

Yuhasz, S.C et al., "Epitopic Discrimination by Monoclonal Antibodies Directed Against the Same . . . ," J of Biomolecular Structure & Cynamics (1989) 7:739-1102.

Zhang, Bin et al., "Development of a High-throughput Robotic Fluorescence-based Assay of HsEg5 Inhibitor Screening," Anal. Biochem (2005) 345:326-335.

U.S. Appl. No. 11/958,515, filed Dec. 18, 2007.

Notice of Allowance mailed on Oct. 8, 2010 (U.S. Appl. No. 12/029,932, filed Feb. 12, 2008).

U.S. Appl. No. 11/958,515, filed Dec. 18, 2007.

* cited by examiner

UGT Reaction Conditions:

50 mM KPO$_4$ pH 7.5
5 mM MgCl$_2$
80 mM EGTA
0.7% v/v UGT Assay Antibody 1
1 nM 488-UTP Tracer UGT preparations (50-300 ug/mL)*
70 μM UDPGA*
100 μM Test Compounds*

* Provided by customer

ASSAY METHOD FOR GROUP TRANSFER REACTIONS

CROSS-REFERENCE TO RELATED APPLICATIONS

This application is a continuation-in-part of U.S. application Ser. No. 11/353,500 filed Feb. 14, 2006, issued as U.S. Pat. No. 7,378,505, which is a continuation-in-part of U.S. application Ser. No. 10/769,578 filed Jan. 30, 2004, issued as U.S. Pat. No. 7,332,278, which claims the priority of U.S. Provisional Application No. 60/443,746 filed Jan. 30, 2003. This application also claims priority to U.S. application Ser. No. 11/137,947 filed May 26, 2005, issued as U.S. Pat. No. 7,355,010. The contents of all of these applications is incorporated by reference here in their entirety.

STATEMENT REGARDING FEDERALLY SPONSORED RESEARCH OR DEVELOPMENT

This invention was made with United States government support awarded by the National Institutes of Health under grant numbers: GM59542, GM69258 and CAI 10535. The United States government has certain rights in this invention.

TECHNICAL FIELD

The present invention relates to group transfer reaction methodologies. The invention provides methods for the detection and quantification of donor-products and the catalytic activities generating the donor-products in group transfer reactions. The invention also provides methods for high throughput screening to identify acceptor substrates, inhibitors, or activators of enzymes catalyzing group transfer reactions. The invention further provides immunoassays, antibodies and related kits for practicing the invention.

BACKGROUND OF THE INVENTION

There are many important biological reactions where the substrates are modified by chemical groups that are donated by other substrates, known as activated donor molecules. These biological reactions are broadly recognized as "group transfer reactions" and have the general reaction:

donor-X+acceptor→donor-product+acceptor-X.

Typically, donor-X, the activated donor molecule, is a nucleotide attached to a covalent adduct. The donor-X is activated by formation of a phosphoester bond in the nucleotide donor. Also the acceptor substrates can include small molecules such as steroid hormones or water, or macromolecules such as proteins or nucleic acids. Products of this reaction are the modified acceptor, acceptor-X and the donor-product molecule.

There are many enzymes that catalyze group transfer reactions such as for example kinases, which use ATP to donate a phosphate group; sulfotransferases (SULTs), which use phosphoadenosine-phosphosulfate (PAPS) to donate a sulfonate group; UDP-glucuronosyltransferases (UGTs), which use UDP-glucuronic acid to transfer a glucuronic acid group; methyltransferases, which use s-adenosyltransferase to donate a methyl group; acetyl transferase, which use acetyl coenzymeA to donate an acetyl group; and ADP-ribosyltransferases, which use nicotinamide adenine dinucleotide (NAD) to donate an ADP-ribose group. Enzymes such as the ones named above, which catalyze group transfer reactions in which the acceptor is a molecule other than water, are classified by the Enzyme Commission as "Transferases" (Transferases are classified as EC2 by the Nomenclature Committee of the International Union of Biochemistry and Molecular Biology [IUBMB]). Enzymes that catalyze group transfer reactions in which water is the acceptor, also known as "hydrolysis" reactions are classified as "Hydrolases" (EC3), and include enzymes such as ATPases, GTPases, and nucleotidases. Many of the enzymes catalyzing group transfer reactions of both types are of interest to pharmaceutical companies.

Automated high throughput screening (HTS) assays are the paradigm for identifying interactions of potential drug molecules with proteins in a drug discovery setting, and this format requires simple, robust molecular assays, preferably with a fluorescent or chemiluminescent readout. The most suitable format for HTS is a homogenous assay, (e.g., "single addition" or "mix and read" assay), which does not require any manipulation after the reaction is initiated and the assay signal can be monitored continuously. Despite their importance from a drug discovery perspective, the incorporation of group transfer enzymes into pharmaceutical HTS programs is being slowed or prevented for a number of reasons: a) homogenous assay methods are not currently available, b) the detection methods used place serious limits on the utility of the assay, and c) the non-generic nature of the assay requires the development of many specific detection reagents to test diverse acceptor substrates.

The approach currently used to identify sulfotransferase substrates or inhibitors requires the use of radioactivity and involves cumbersome post-reaction separation steps, such as precipitation or chromatography. For instance, $^{35}$S-PAPS is used in a sulfotransferase reaction and the labeled product is quantified by scintillation counting after selective precipitation of unreacted $^{35}$S-PAPS (Foldes, A. and Meek, J. L., Biochim Biophys Acta, 1973, 327:365-74). This approach is not desirable in a high throughput screening (HTS) format because of the high radiation disposal costs and because the incorporation of separation steps complicates the automation process. Other SULT assays have been developed using colorimetric and fluorescent means, but they are dependent on the use of a specific acceptor substrate for detection, so their use is limited to a single SULT isoform, and they cannot be used to screen for diverse substrates (Burkart, M. D. and Wong, C. H., Anal Biochem, 1999, 274:131-7; Frame, L. T., Ozawa, S. et al., Drug Metab Dispos, 2000, 28:1063-8). As a result, SULT interaction studies are currently not included during the preclinical development of drugs. Also UGTs are currently assayed using radiolabeled donor molecules and require post-reaction separation steps such as thin layer chromatography (TLC) or high pressure liquid chromatography (HPLC) which seriously hampers preclinical HTS programs (Ethell, B. T., Anderson, G. D. et al., Anal Biochem, 1998, 255:142-7). Likewise, traditionally, kinases have been assayed by filter capture or precipitation of radiolabeled polypeptide substrates produced using $^{32}$P-ATP or $^{33}$P-ATP as donor. However, since this method requires a separation step such as filtering or centrifugation, it cannot be easily adapted to an automated HTS format. Surface proximity assays (SPA) allow radioassays in a multiwell format with no separation (Mallari, R., Swearingen, E. et al., J Biomol Screen, 2003, 8:198-204) but their use by pharmaceutical companies is declining because of the disposal and regulatory costs of handling radioisotopes.

Because of the high level of interest in developing kinase inhibitor drugs, there has been a great deal of effort among scientists to develop improved assay methods for this enzyme family. Homogenous assay methods have been developed, in which highly specific reagents are used to detect the reaction products in the presence of the other components of the reaction using a light-based readout, such as fluorescence or chemiluminescence. The most common homogenous approach used for kinase assays is immunodetection of phosphopeptide products exhibiting different fluorescence properties (Zaman, G. J., Garritsen, A. et al., Comb Chem High Throughput Screen, 2003, 6:313-20). In this method, phosphorylation of substrate peptide leads to displacement of a fluorescent phosphopeptide tracer from an anti-phosphopeptide antibody and causes a change in its fluorescence properties. This basic approach has been adapted to several different readout modes used for competitive immunoassays including Fluorescence polarization (FP) (Parker, G. J., Law, T. L. et al., J Biomol Screen, 2000, 5:77-88); time resolved fluorescence (Xu, K., Stem, A. S. et al., J Biochem Mol Biol, 2003, 36:421-5); fluorescence lifetime discrimination (Fowler, A., Swift, D. et al., Anal Biochem, 2002, 308:223-31); and chemiluminescence (Eglen, R. M. and Singh, R., Comb Chem High Throughput Screen, 2003, 6:381-7).

The shortcoming with this approach is the requirement for phosphopeptide-specific antibodies. Though generic phosphotyrosine antibodies are common, phosphoserine and phosphothreonine antibodies are notoriously difficult to produce and only recognize phospho-serine or -threonine in the context of specific flanking amino acids (Eglen and Singh, 2003). There are over 400 kinases in humans and their specificity for phosphorylation sites vary widely. Thus, different antibodies are needed for assaying diverse kinases or profiling acceptor substrates. This greatly complicates the incorporation of new kinases into HTS, especially if their substrate specificity is not well defined. It also creates analysis problems in comparing data among kinases with different substrate selectivities, because the output of the assay depends on the particular antibody(Ab)-phosphopeptide pair used. Although efforts to develop generic phospho-serine antibodies and identify more generic kinase substrates continue (Sills, M. A., Weiss, D. et al., J Biomol Screen, 2002, 7:191-214), research in this direction has not been very successful to date.

A number of alternative approaches have been developed to circumvent the problem of context-specific Ab-phosphopeptide interactions, including use of metal complexes to bind phosphopeptides (Scott, J. E. and Carpenter, J. W., Anal Biochem, 2003, 316:82-91) and the use of modified ATP analogs that allow covalent tagging of phosphopeptide products (Allison Miller-Wing, E. G., Barbara Armstrong, Lindsey Yeats, Ram Bhatt, Frank Gonzales, and Steven Gessert., SBS 9th Annual Conference and Exhibition, Portland, Oreg., 2003). Chemical phosphate binding reagents suffer from background binding to nucleotide phosphates, requiring the use of very low, non-physiological levels of ATP and limiting assay flexibility. Modified nucleotides do not provide a generic format because the ability to use the ATP analogs as donors varies among kinases, requiring the development of a number of different analogs. Also competition of inhibitors with the modified nucleotides at the kinase ATP binding site—the most frequent site for kinase inhibitor binding—does not reflect the physiological situation. Differences in protease sensitivity caused by peptide phosphorylation have also been exploited in developing fluorescence based kinase assays (Kupcho, K., Somberg, R. et al., Anal Biochem, 2003, 317:210-7), but these assays are not truly homogenous; i.e. they require the post-reaction addition of developing protease reagents. In addition, the applicability of this method is limited to peptides where kinase and protease specificity overlap.

There are also a few methods that are dependent on interaction of reaction products with specific multiwell plate chemistries, but these are not truly homogenous in that they require post reaction reagent additions and/or processing. Also the requirement for specialized instrumentation for processing and/or detection does not fit with the open architecture desired by most pharmaceutical HTS platforms.

Furthermore, microfluidics-based kinase assays that rely on electrophoretic separation of reaction products have been developed (Xue, Q., Wainright, A. et al., Electrophoresis, 2001, 22:4000-7). In these assays, phosphorylated peptide products are electrophoretically separated from the non-phosphorylated acceptor substrates, thus eliminating the need for specialized detection reagents. However, in practice, the kinase assays are often run in multiwell plates and then the products are transferred to microfluidic devices for separation—a cumbersome process for an HTS format.

In summary, the non-generic nature of the current group transfer assays is resulting in significant expense and delays for drug discovery because of the need to develop assays for individual enzymes or small subgroups within a family. Also, because many of the current assays are based on modification and detection of specific tagged acceptors, there is limited ability for testing different acceptor substrates. Often the tagged acceptor substrates used are different from the substrates that are phosphorylated in vivo, thus the physiological relevance of the assay is questionable. In addition, a major concern in the pharmaceutical industry is that because of the non-generic nature of the current assays, investigators are sometimes forced to use different methods for different kinases. However, studies have shown that there are significant differences in the pharmaceutical targets identified using different assays methods (Sills, M. A. et al., J Biomol Screen, 2002, 7:191-214), which is a significant problem for profiling inhibitor selectivity across several kinases. These shortcomings of the existing HTS assay methods for group transfer reactions are hampering the rapid analysis of important enzyme families in pharmaceutical drug discovery programs.

Other existing approaches for assaying group transfer reactions have been to enable screening of diverse chemicals as substrates for group transfer reactions by detecting the donor molecule product, because it is the same regardless of the acceptor being modified. Detection of the donor product has been thought to provide the basis of a generic assay method, ADP is always a product of a kinase reaction and phosphoadenosine-phosphate (PAP) is always the product of a sulfotransferase reaction. Detection of these products, however, is complicated because the cleaved mono- and di-nucleotides cannot be differentiated from the activated donor molecules based on absorbance or fluorescence properties because for example ADP has the same fluorescence and absorbance properties as ATP. Separation of the donor product from the donor can be effected using chromatographic methods, such as thin layer chromatography or high pressure liquid chromatography, but incorporation of these methods into an HTS format is cumbersome.

To circumvent this difficulty, detection of the donor product has been achieved by using additional enzymes to generate a detectable product from the primary reaction product—the cleaved mono- or di-nucleotide; this is known as an enzyme coupled reaction. For instance, enzymes and other small molecules can be used for ADP-dependent generation of NADPH, which is detected by absorbance or fluorescence at 340 nm (Walters, W. P. and Namchuk, M., Nat Rev Drug Discov, 2003, 2:259-66). An enzyme coupled reaction has also been developed for UGTs, another type of group transfer enzyme (Mulder, G. J. and van Doom, A. B., Biochem J, 1975, 151:131-40). However, the optical interference of drug compounds with absorbance assays, especially in the ultra violet, is a widely recognized problem with this approach. Another shortcoming of this approach is that all of the enzymes used to couple the detection are subject to potential inhibition from the chemicals being screened.

Another generic approach is to monitor ATP consumption using Luciferase as a reporter to detect protein kinase activity. An example of this method was disclosed by Crouch et al., in U.S. Pat. No. 6,599,711. Their method entailed determining the activity of a protein kinase to be tested by adding a substrate capable of being phosphorylated by the protein kinase to a solution having ATP and a protein kinase to be tested, and another solution having ATP in the absence of the kinase to be tested. The concentration or the rate of time change of ATP and/or ADP was then measured using bioluminescence. However this assay is not optimal because it relies on small decreases in a high initial signal. The need to keep ATP concentrations low to minimize background results in nonlinear reaction kinetics if assay conditions are not carefully controlled. In a related method, competition binding assays using fluorescent ATP analogs have also been developed, but these do not give a measure of enzyme catalytic activity, thus are of limited utility.

Enzymes that catalyze group transfer reactions where water is the acceptor, hydrolases, present an even more difficult assay challenge because generally the products are all small molecules, and thus more difficult to detect than a covalently adducted peptide or nucleic acid, which can be detected easily with an antibody. An example of such a reaction is that catalyzed by an ATPase: $ATP+H_2O \rightarrow ADP+$phosphate. Below we describe the HTS methods used to detect some types of hydrolases and their shortcomings.

A number of ATPases and GTPases are of significant interest for drug discovery because they are involved in cellular and subcellular movement (Pellegrini, F. and Budman, D. R., Cancer Invest, 2005, 23:264-73), ion transport or drug transport (Xie, Z. and Xie, J., Front Biosci, 2005, 10:3100-9), signal transduction (Kimple, R. J., Jones, M. B. et al., Comb Chem High Throughput Screen, 2003, 6:399-407), and the control of protein stability (Workman, P., Curr Cancer Drug Targets, 2003, 3:297-300).

The most common non-radioactive method used to detect ATPases and GTPases is colorimetric determination of inorganic phosphate using dyes like malachite green (Rowlands, M. G., Newbatt, Y. M. et al., Anal Biochem, 2004, 327:176-83). This method is problematic for HTS because the colorimetric readout is not very sensitive and is also subject to interference from colored test compounds. Other methods of phosphate detection have been developed more recently using fluorescently labeled phosphate binding proteins that undergo a change in fluorescence associated with conformational changes induced by phosphate binding (Brune, M., Hunter, J. L. et al., Biochemistry, 1994, 33:8262-71). Though fluorescence is preferable to absorbance as a detection mode for HTS, any method that relies upon phosphate detection is going to suffer from background signal because of the high phosphate concentrations found in biological samples and its use as a common biological buffer reagent. Detection of ADP using a coupled enzyme assay linked to NADPH formation is also used as an HTS assay approach for ATPases (DeBonis, S., Skoufias, D. A. et al., Mol Cancer Ther, 2004, 3:1079-90), but this method again relies on absorbance detection and so suffers from low sensitivity and interference from colored compounds. The coupled enzyme approach has also been adapted for fluorescence detection (Zhang, B., Senator, D. et al., Anal Biochem, 2005, 345:326-35), but the requirement for several enzymes for signal generation greatly increases the potential for assay interference from test compounds.

In general, the use of enzymes that catalyze group transfer reactions into HTS assays has been hampered by the lack of universal, homogenous assay methods that are not subject to interference from molecules in pharmaceutical drug libraries. Accordingly, it would generally be desirable to provide universal methods for assaying enzymes involved in group transfer reactions that are well suited for HTS drug discovery.

BRIEF SUMMARY OF THE INVENTION

To enable facile incorporation of important group transfer enzymes into HTS assays, applicants have developed assays based on homogenous immunodetection of the donor product. The general equation for the group transfer reaction is: donor-X +acceptor→donor-product+acceptor-X, wherein the donor-product is detected by the general detection reaction: first complex+donor-product→second complex+displaced detectable tag. Because the donor product is the same for all enzymes that catalyze a given type of group transfer reaction, the same detection reagents can be used for all the members within a family of group transfer enzymes and with any acceptor substrate. The assay products can be detected using homogenous fluorescence or chemiluminescence methods which are not subject to significant interference or background signal from molecules in pharmaceutical drug libraries.

Thus, the present invention is summarized as methods and components thereof for detecting the activity of and screening acceptor substrates, inhibitors, or activators of enzymes catalyzing group transfer reactions to facilitate the development of more selective and therapeutic drugs. This is accomplished through a highly selective antibody used to bind the donor product of the group transfer reaction. Antibody-antigen interactions can be detected by a variety of detection assays described here such as fluorescence polarization immunoassay (FPIA) or fluorescence resonance energy transfer (FRET or TR-FRET) immunoassay.

The detection mode applicants have used to put the method into practice is a competitive FPIA, because it is well suited for pharmaceutical HTS assays. With this detection mode, enzymatically generated donor product displaces a fluorescent derivative of the donor product, called a tracer, from an antibody resulting in a decrease in tracer fluorescence polarization. The key reagents for the assay are an antibody that binds with high selectivity to the donor product, and not to the uncleaved donor molecule, and a tracer—a fluorescent derivative of the donor product that retains its structure sufficiently to bind the antibody. The invention provides a novel assay for detecting and quantifying activity for enzymes that catalyze group transfer reactions using diverse substrates. The invention also provides a method of screening for substrates, inhibitors, or activators of the group transfer reactions.

In one aspect, the invention provides a universal homogenous assay method for directly detecting a donor-product produced in a group transfer reaction in the presence of a donor molecule. The method includes a) reacting a donor molecule which is guanosine triphosphate (GTP), with an acceptor in the presence of a catalytically active enzyme to form the donor-product which is guanosine diphosphate (GDP), such that the GTP is partially consumed; b) combining the GDP produced in a group transfer reaction with a tracer and an antibody to provide a reaction mixture, the antibody being specific for the GDP, the tracer comprising a nucleotide conjugated to a fluorophore, and capable of binding to the antibody to produce a detectable change in fluorescence polarization; c) measuring the fluorescence polarization of the mixture to obtain a measured fluorescence polarization; and d) comparing the measured fluorescence polarization with a characterized fluorescence polarization value corresponding to a known GDP concentration to directly detect the GDP produced in the group transfer reaction.

In another aspect, the invention provides an antibody produced against a donor product of an enzymatically catalyzed group transfer reaction, wherein the antibody has the ability to preferentially recognize a donor-product in the presence of a donor molecule, and wherein the antibody binds the donor-product, nucleotide di-phosphate with at least ten-fold higher affinity than to the donor molecule.

An antibody produced against a donor product of an enzymatically catalyzed group transfer reaction, wherein the antibody has the ability to preferentially recognize a donor-product in the presence of a donor molecule, and wherein the antibody binds the donor-product, guanosine diphosphate (GDP) with at least ten-fold higher affinity than to the donor molecule, GTP.

In yet another aspect, the invention provides a universal homogenous assay method for directly detecting a donor-product produced in a group transfer reaction. The method including a) providing a reaction mixture having products of the group transfer reaction, a tracer and an antibody, wherein the products of the reaction include the donor-product which is a guanosine diphosphate (GDP), in the presence of a donor molecule which is a guanosine triphosphate (GTP), wherein the antibody is specific for the GDP, and wherein the tracer comprises a nucleotide conjugated to a fluorophore and is capable of binding to the antibody to produce a detectable change in the fluorescence properties of the tracer; b) measuring the fluorescence properties of the reaction mixture to obtain a measured value; and c) comparing the measured fluorescence properties with a characterized fluorescence property value corresponding to a known GDP concentration to directly detect the GDP produced in the group transfer reaction.

In yet another aspect, the invention provides assay kits for detecting a donor-product from a group transfer reaction catalyzed by a group transfer enzyme, including but not limited to adenosine triphosphatase (ATPase) or guanine triphosphatase (GTPase). The assay kit includes a macromolecule and a tracer, each in an amount suitable for at least one homogeneous fluorescence polarization assay for donor-product, wherein the macromolecule is an antibody or an inactivated enzyme.

In another aspect, the invention provides a tracer compound for use in a homogenous competitive binding assay to detect a donor-product of a group transfer reaction catalyzed by adenosine triphosphatase (ATPase) or guanine triphosphatase (GTPase), wherein the tracer comprises a fluorophore conjugated to a nucleotide.

In a related aspect, the invention provides a chemical linker positioned between a fluorophore and a nucleotide of a tracer compound; wherein the linker may include an aminoallyl, a diaminoalkane, or an aminoalkynyl group.

Other advantages and a fuller appreciation of specific adaptations, compositional variations, and physical attributes will be gained upon an examination of the following detailed description of the various embodiments, taken in conjunction with the appended claims.

Figure 1:
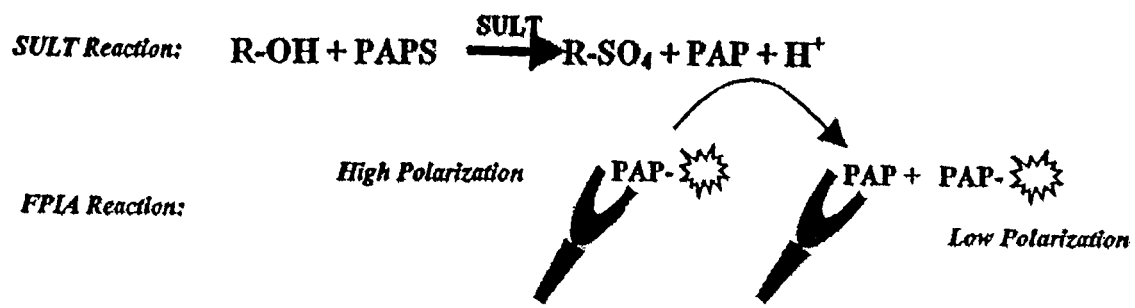
FIG. 1 illustrates a fluorescence polarization immunoassay (FPIA) reaction for the SULT reaction product, PAP.

Before the various embodiments of the invention are explained in detail, it is to be understood that the invention is not limited in its application to the details set forth in the following description. The invention is capable of being practiced or being carried out in a variety of ways. Also, it is to be understood that the phraseology and terminology used herein is for the purpose of description and should not be regarded as limiting in any way.

DETAILED DESCRIPTION OF THE INVENTION

The present invention broadly relates to novel assay methods for detecting and quantifying the donor-product or the catalytic activities generating the donor-product from group transfer enzymes using diverse substrates. The invention also provides the antibodies specific to the donor product and assay kits for practicing the invention in a high-throughput screening format. The general equation for the group transfer reaction includes a donor-X+acceptor→donor-product+acceptor-X, wherein the donor-product is detected by the general detection reaction: first complex+donor-product→second complex+displaced detectable tag. Thus, in accordance with the invention, a highly selective antibody is used to bind the donor product of the group transfer reaction, and this binding event is detected, using an immunoassay, such as for example a competitive binding FPIA which is well suited for pharmaceutical HTS assays. By using this detection mode, enzymatically generated donor product displaces a tracer, from an antibody resulting in a decrease in tracer fluorescence polarization. The key reagents for the assay are antibody that binds with high selectivity to the donor product, and not to the uncleaved donor molecule, and a tracer—a fluorescent derivative of the donor product that retains its structure sufficiently to bind the antibody.

In particular the invention provides a universal assay method in that a single set of detection reagents can be used for all of the enzymes in a given family of group transfer enzymes and all acceptor substrates for that family. Because of its universal nature, the invention will accelerate the incorporation of SULTs, protein kinases, ATPases or GTPases, and other group transfer enzymes into HTS screening. For example, there are eleven known SULT isoforms, using the method of the present invention, all eleven of the SULT isoforms may be screened for their ability to sulfate diverse compounds in the same experiment using the same detection reagents, protocol and instrumentation. This is an important capability because enzymes that catalyze xenobiotic conjugation (e.g., SULTs and UGTs) have very broad acceptor substrate specificity. With respect to kinases, there is even more diversity within the enzyme family. There are over 400 protein kinases in humans, and there is great diversity in their acceptors substrate specificity such that either physiological protein acceptor substrates as well as short peptides may be used.

Likewsie, a number of protein kinases may be used in the assay of the invention using their diverse acceptor substrates and screened for inhibitors using the same detection reagents, protocol and instrumentation. For these reasons and others provided below, the FPIA based donor product detection assays of the invention for group transfer reactions such as ATPases, GTPases, SULTs, UGTs and kinases, among others are very well suited for automated HTS applications.

Accordingly, the present invention will now be described in detail with respect to such endeavors; however, those skilled in the art will appreciate that such a description of the invention is meant to be exemplary only and should not be viewed as being limiting on the full scope thereof.

Definitions

Certain terms used herein are intended to have the following general definitions:

The term "group transfer reaction" as used herein refers to the general reaction:
donor-X+acceptor→donor-product+acceptor-X.

Representative group transfer reactions and their Enzyme Commission (EC) classifications by the Nomenclature Committee of the International Union of Biochemistry and Molecular Biology are shown as follows:

Kinase reaction: ATP+acceptor→ADP+acceptor-PO$_4$, EC 2.7;

Glycosyltransferase reaction: NDP-glycan+acceptor→NDP+acceptor-glycan, EC 2.4;

Sulfotransferase reaction: acceptor-XH+3'-phosphoadenosine 5'-phosphosulfate→acceptor-SO$_4$+3'-phosphoadenosine 5'-phosphate+H$^+$, EC 2.8.2;

Methyltransferase reaction: S-adenosylmethionine+acceptor→acceptor-CH$_3$+S-adenosylhomocysteine, EC 2.1.1;

Acetyl transferase reaction: acetyl CoenzymeA+acceptor→acceptor-COCH$_3$+CoenzymeA, EC 2.3.1;

ATPase reaction: ATP+H$_2$O→ADP+phosphate, EC 3.6.3, and 3.6.4;

GTPase reaction: GTP+H$_2$O→GDP+phosphate, EC 3.6.5;

5'-nucleotidase reaction: 5'-ribonucleotide+H$_2$O→ribonucleoside+phosphate, EC 3.1 and 3.5; and thymidylate 5'-phosphatase: thymidylate+H$_2$O→thymidine+phosphate, EC 3.1 and 3.35

Group transfer reactions in-part such as sulfation by SULTs, phosphorylation by kinases, UDP-glucuronidation by UGTs, and GTP hydrolysis are suitably applicable to the methods of the invention because one can isolate antibody/detectable tag pairs for the donor products, which are PAP, ADP, UDP, and GDP, respectively. Also group transfer reactions are generally involved in a number of biological processes, such as hormone biosynthesis and function; enzyme regulation and function; and xenobiotic metabolism.

The term "universal assay" and "generic assay" are used interchangeably to refer to a method whereby all members of the group transfer reaction enzyme family and all of their acceptor substrates can be detected with the same assay reagents.

The term "covalent adduct" refers to the moiety that is transferred from the donor molecule to the acceptor in a group transfer reaction; sulfonate, phosphate, and glucuronic acid respectively for SULTs, kinases, and UGTs.

The term "donor-product" as used herein refers to the product of a group transfer reaction that is the fragment of the donor molecule that is generated when the covalent adduct is transferred to acceptor. Often it is a nucleotide (naturally occurring or synthetic) such as a PAP, UDP or ADP; or a non-nucleotide such as a s-adenosylhomocysteine, nicotinamide or a CoenzymeA. The donor-product is detected by a general reaction including a first complex+donor-product→second complex+displaced detectable tag.

The term "tracer" as used herein refers to a displaced detectable derivative or tag of a donor product that retains its structure sufficiently to bind to a specific antibody.

The term "donor" as used herein refers to a substrate for an enzyme catalyzing a group transfer reaction that carries the activated covalent adduct. Examples of suitable donors include not only nucleotides, but also s-adenosyl methionine and acetyl-CoA, among others.

The term "donor-X" is another term for donor molecule in which X represents the covalent adduct.

The term "acceptor" as used herein refers to a substrate for an enzyme catalyzing a group transfer reaction to which the covalent adduct becomes covalently attached, wherein the substrate is a polypeptide, a protein, a nucleic acid, a carbohydrate, a lipid or a small molecule substrate such as a steroid or an amino acid.

The term "acceptor-X" as used herein refers to a reaction product in which X is the covalently bound covalent adduct; wherein the covalent adduct includes at least one of a phosphate, a sulfate, a carbohydrate, a naturally occurring amino acid, a synthetically derived amino acid, a methyl, an acetyl, or a glutathione moiety, and a combination thereof. The covalent adduct is capable of altering either the function, the stability, or both the function and the stability of the acceptor substrate. In the case of hydrolysis reactions, where the acceptor is water, the term "acceptor-X" refers to the adduct to which a water molecule has been added; e.g., phosphate for ATPases and GTPases.

The term "catalytically active enzyme" as used herein refers to at least one of the following enzymes: sulfotransferases, kinases, UDP-glucuronosyltransferases, methyl transferases, acetyl transferases, glutathione transferases, ATPases, GTPases, or ADP-ribosyltransferases.

The term "catalytic activity" as used herein refers to a chemical catalytic activity, an enzymatic activity, or a combination thereof.

The term "first complex" as used herein refers to a complex having a macromolecule (i.e., an antibody or an inactivated enzyme) and a detectable tag.

The term "second complex" as used herein refers to a macromolecule and the donor product wherein the detectable tag is competitively displaced by the donor-product.

The term "observable" as used herein refers to detectable change in fluorescence, fluorescence intensity, fluorescence lifetime, fluorescence polarization, fluorescence resonance energy transfer (FRET) or chemiluminescence of the second complex or the displaced detectable tag and a combination thereof to obtain a measured observable. The measured observable is compared with a characterized observable, wherein the characterized observable corresponds to the first complex.

The term "detectable tag" as used herein refers to a fluorescent or chemiluminescent tracer, which is conjugated to a donor product. Fluorescence is the preferred mode of detection for the invention. A suitable detectable tag may be produced by conjugating for example, a chemiluminescent tag or a fluorophore tag, to the donor product molecule in such a way that it does not interfere significantly with antibody binding (i.e., most likely attached via the base portion of the nucleotide). Fluorophores applicable to the methods of the present invention include but are not limited to fluorescein, rhodamine, BODIPY®, Texas Red, Alexa Fluors® and derivative thereof known in the art. Rhodamine conjugates and other red conjugates may be synthesized and optimized as detectable tags because their higher wavelength emission is less subject to interference from autofluorescence than the green of fluorescein.

Chemiluminescent tags applicable to the invention include Lumigen TMA-6 and Lumigen PS-3 (Lumigen, Inc., Southfield, Mich.) which have adequate chemiluminescence quantum yield. These reagents possess an easily measured signal by virtue of an efficient chemiluminescent reaction with a predictable time course of light emission. Furthermore, chemiluminescent tags contribute little or no native background chemiluminescence. Also, measurement of light intensity is relatively simple, requiring only a photomultiplier or photodiode and the associated electronics to convert and record signals. In addition, chemiluminescent signals can be generated in an immunoassay using enzyme fragment complementation methods, where the detectable tag would be the donor product conjugated to fragment A of a reporter enzyme, and its displacement from antibody by the donor product generated in the group transfer reaction would allow it to associate with fragment B of the enzyme resulting in formation of a catalytically active reporter enzyme capable of acting on a chemiluminescent substrate. This method has been described using β-galactosidase as a reporter enzyme in U.S. Pat. No. 4,708,929.

The term "immunoassay" as used herein may refer to a number of assay methods wherein the product is detected by an antibody such as for example a homogenous assay, homogeneous fluorescence immunoassay, a homogeneous fluorescence intensity immunoassay, a homogeneous fluorescence lifetime immunoassay, a homogeneous fluorescence polarization immunoassay (FPIA), a homogeneous fluorescence resonance energy transfer (FRET) immunoassay or a homogenous chemiluminescent immunoassay, or a non-homogenous assay such as enzyme-linked immunoassay (ELISA) and a combination thereof.

The term "fluorescence polarization immunoassay" or "FPIA" as used herein refers to an immunoassay for detecting the products of group transfer reactions. Fluorescence polarization (FP) is used to study molecular interactions by monitoring changes in the apparent size of fluorescently-labeled or inherently fluorescent molecules (Checovich, W. J., Bolger, R. E. et al., Nature, 1995, 375:254-6; Owicki, J. C., J Biomol Screen, 2000, 5:297-306). When a small fluorescent molecule (tracer) is excited with plane polarized light, the emitted light is largely depolarized because the molecule rotates rapidly in solution during the fluorescence event (the time between excitation and emission). However, if the tracer is bound to a much larger receptor, thereby increasing its effective molecular volume, its rotation is slowed sufficiently to emit light in the same plane in which it was excited. The bound and free states of the fluorescent molecule each have an intrinsic polarization value, a high value for the bound state and a low value for the free state. In a population of molecules, the measured polarization is a weighted average of the two values, thus providing a direct measure of the fraction of the tracer molecule that is bound. Polarization values are expressed as millipolarization units (mP), with 500 mP being the maximum theoretical value.

In practice, small molecules like fluorescein have polarization values of approximately 20 mP, and when bound by an antibody their polarization increases by 100 to 400 mP. In a competitive FPIA, a fluorescent tracer may be displaced from binding to antibody by the donor product, as shown in FIG. 1. The signal is proportional to the difference in the bound versus free tracer fractions, thus both the dynamic range and the sensitivity of the assay are dependent upon the affinity of the antibody for the tracer and the donor product. To establish a suitable dynamic range for an FPIA, approximately 70-80% of the tracer must be bound to antibody in the absence of competitor.

For example, FIG. 1 shows a schematic of a competitive FPIA for the SULT reaction product PAP in which the PAP produced from the SULT reaction competes with the tracer (fluorescently tagged PAP), for binding to anti-PAP antibody. In this format, the starting polarization of the tracer is high because it is almost all bound to antibody, and it decreases as the reaction proceeds and the tracer is displaced from the antibody. The amount of PAP produced in a SULT reaction can be quantified by using the following equation:

$$\log\,[PAP\,\text{product}] = \log\frac{(\text{highest polarization} - mP_{observed})}{(mP_{observed} - \text{lowest polarization})} + \log\,IC_{50}.$$

In the enzymatic assay encompassed by the present invention, the PAP for SULTs or ADP for kinases is produced in stoichiometric amounts with the sulfated product or phosphorylated peptide, respectively. Thus, the use of a standard curve for PAP or ADP among other donor products will allow a direct measure of enzyme turnover.

The term "high throughput screening" or "HTS" as used herein refers to the testing of many thousands of molecules (or test compounds) for their effects on the function of a protein. In the case of group transfer reaction enzymes many molecules may be tested for effects on their catalytic activity. HTS methods are known in the art and they are generally performed in multiwell plates with automated liquid handling and detection equipment; however, it is envisioned that the methods of the invention may be practiced on a microarray or in a microfluidic system.

The term "library" or "drug library" as used herein refers to a plurality of chemical molecules (test compounds), a plurality of nucleic acids, a plurality of peptides, or a plurality of proteins, and a combination thereof. Wherein the screening is performed by a high-throughput screening technique, wherein the technique utilizes a multiwell plate or a microfluidic system.

The terms "binding molecule" or "macromolecule" as used herein refers to an antibody or an inactivated enzyme.

The term "antibody" as used herein refers to a monoclonal, a polyclonal or recombinant antibody. The antibody is produced against a donor-product of a group transfer reaction and is able to preferentially distinguish between a donor-product and a donor in the presence of a high donor concentration. The antibody also exhibits specificity towards at least one of a phosphate portion of a nucleotide, (i.e., an ability to distinguish between a 5'-phosphate, a 5'-phosphosulfate, a 5'-diphosphate and a 5'-triphosphate). For example, in the SULT reaction, the antibody of the present invention differentiates with high stringency between PAP and PAPS. The donor-product molecule for the SULT reaction, PAPS, differs only by the addition of a sulfate group linked to the 5' terminal phosphate. This may seem like a relatively small structural difference, but the demonstrated ability of antibodies to discriminate between molecules that differ by a single phosphate—which is very similar in size and structure to a sulfate group—provides an important feature of the present invention. For example, an antibody may be raised against the ribosyl phosphate portion of the molecule. Furthermore, the FPIA-based SULT assay method of the present invention suitably requires an antibody that specifically binds the reaction product PAP in the presence of excess PAPS.

In practicing the invention with respect to kinases, antibodies that specifically recognize ADP and not ATP may be generated in animals or by in vitro recombinant methods using ADP conjugated to a carrier protein in such a way that the phospho-ribosyl portion of the molecule is exposed, but the adenine portion is largely hidden from immunoreactivity. Alternatively, with respect to methyltransferases and acetyltransferases, antibodies that specifically recognize small molecules other than nucleotides, respectively s-adenosyl homocysteine and Coenzyme A are used.

The term "inactivated enzyme" as used herein refers to a binding molecule that may bind to the donor product. In the case of a kinase, the ADP is the donor product and an inactivated nucleoside diphosphate (NDP) kinase may be the binding molecule. It is known that in many enzymes, separate domains are involved in binding and in catalysis. A selective destruction of the catalytic activity with preservation of the binding properties by genetic engineering, allosteric inhibition, or other chemical means such as taking out cofactors, heme groups, etc. may enable enzymes, particularly multi-subunit enzymes to function as specific carriers for their substrates that are no longer able to chemically modify these substrates.

The term "antibody-detectable tag pair" as used herein refers to an anti-donor product antibody and detectable tag (fluorescent-donor product) molecule that allow detection of donor product produced in a group transfer reaction. A suitable dissociation constant for binding of the antibody/detectable tag pair is $1 \times 10^{-5}$ M or lower, resulting in a minimal fluorescence polarization shift of 50 mP relative to the unbound detectable tag, and with minimal cross reactivity to the donor molecule at reaction concentrations. The optimal antibody-detectable tag pair may be identified by testing a number of different antibodies generated using different sites of attachment to the donor molecule, different linkers to the carrier protein, and including some non-hydrolyzable analogs for interaction with a set of detectable tags generated by varying the chemistry of donor molecule attachment to a fluorophore. The changes in fluorescence or chemiluminescence of the detectable tag upon interaction with an antibody that could have a fluorophore for example attached to it; may be used as a measure of their interaction.

The term "linker" as used herein refers to spacer arm structures that join the donor product to the carrier protein in the immunogen or to the fluorophore in the detectable tag. There are short linkers (i.e., carbamoyl and aminoethyl groups) that will sterically minimize the accessibility of the adenine ring and longer six carbon linkers that will allow more flexible presentation of the antigen. The linker molecule affects detectable tag characteristics in a number of important ways that impact both its antigenic and fluorescence properties. There is generally a balance that must be struck between separating the antigen from the fluorophore enough to allow unhindered interaction with antibody without creating too much freedom of motion for the fluorophore. The former result in lowered affinity antibody binding and in quenching of the fluorophore, whereas the latter reduces the polarization shift upon antibody binding, thereby reducing the dynamic range of the assay. Different linkers can be interchanged using relatively simple chemistry, thus the linker is varied in a number of ways in efforts to optimize the antigenic and fluorescence properties of the detectable tag. Furthermore, approaches may be employed similar to those described for PAP conjugation of an antibody involving heterobifunctional linkers to first introduce spacer arms and/or aromatic substituents onto PAP, followed by reaction with reactive fluorescein derivatives. This approach greatly expands the range of possible linker structures.

Methods and Materials

The following experimental protocols of the invention are not limited to the particular methodology, protocols, antibodies, enzymes, detectable tags, among other reagents described, as these may vary depending on the group transfer reaction. It is also to be understood that the terminology used herein is for the purpose of describing particular embodiments only, and is not intended to limit the scope of the present invention.

Development of Assay Reagents

In developing a successful HTS assay format for the invention the affinity and specificity of the antibody-detectable tag pair, and the resultant changes in detectable tag fluorescence properties ultimately define the overall performance of the assay, including sensitivity, dynamic range, and signal to noise ratios. As such, to optimize this interaction, applicants have provided an iterative co-development strategy for these key assay reagents.

This co-development strategy provides that several different antibodies be tested to identify one that specifically binds the donor product in the presence of excess donor molecule. For the immunogen used to generate antibody, the donor molecule may be conjugated to carrier protein (e.g., BSA or KLH) via attachment through different positions using linker molecules of varying lengths with reactive termini; e.g. amino groups. The same donor-linker reactive intermediates used for carrier protein conjugation may be used to synthesize fluorescein-PAP conjugates to test as detectable tags. The resulting matrix of antibodies and detectable tags may be tested for binding using FP assays, and the pairs that exhibit high affinity binding and maximal FP shifts may be used as the basis for further optimization of tracer characteristics. Optimized antibody-detectable tag pairs may be tested for detection of donor molecule production in enzymatic reactions.

Also, it is envisioned that several donor molecule antigens and detectable tags may be synthesized by conjugating the donor molecule to carrier protein and fluorescein, while retaining an overall structural bias that maximizes antibody recognition of the part of the molecule that differs from the donor so that crossreactivity with the donor is minimized. For a nucleotide donor products, this generally means attaching the linker to the base portion of the nucleotide so that the ribosyl-phosphate moiety is unaltered and fully exposed. For example, in the case of adenine nucleotide donor product, it is known in the art that conjugation to adenine will minimize antibody cross reactivity that could occur via binding to the adenine moiety (Goujon, L., et al., J. Immunol. Methods, 1998, 218:19-30; Horton, J. K., et al, J Immunol Methods, 1992, 155:31-40; Bredehorst, R., et al., Biochim Biophys Acta, 1981, 652:16-28). The site of hapten conjugation also can affect the affinity of the resulting antibodies (Crabbe, P., et al., J Agric Food Chem, 2000, 48:3633-8). With some larger donor products, such as Coenzyme A, it may be desirable to use only a portion of the molecule as antigen so that crossreactivity with the structural elements shared with the donor are minimized.

Generation of High Affinity, High Selectivity Antibodies

In accordance with methods of the present invention, one skilled in the art may readily prepare a variety of specific antibodies (i.e., polyclonal, monoclonal or recombinant) against donor molecules bound to carrier proteins.

In general polyclonal antibodies against a range of donor product antigens are suitably generated in rabbits. It is difficult to predict how the structure of the antigen will affect the affinity and selectivity of the resulting antibodies, but the carrier protein and mode of conjugation both can have a profound effect (Signorini, N., Molko, D. et al., Chem Res Toxicol, 1998, 11:1169-75; Crabbe, P., Van Peteghem, C. et al., J Agric Food Chem, 2000, 48:3633-8; Ishiguro, H., Shimokawa, T. et al., Oncogene, 2002, 21:6387-94). Accordingly, antibodies may be generated using conjugation to two different proteins via different sites on the donor product and using different length linker regions.

The injection of animals and collection of serum may be performed according to the following protocol. Three rabbits may be immunized with each of the antigens that may be developed. The yields of antiserum from a single rabbit (~100 ml) are suitable for many thousand to millions of FPIA assays depending on the titer, affinity, and the multivalent nature of polyclonal-antigen interactions resulting in very high affinity binding. As such, for these reasons polyclonals are frequently used for FPIAs (Nasir, M. S, and Jolley, M. E., Comb Chem High Throughput Screen, 1999, 2:177-90).

Also, encompassed within the scope of the present invention are monoclonal antibodies which may be produced according to the methods provided in previously published protocols (Harlow, E. L., D., 1999), which are fully incorporated herein by reference. Although mice are widely used for generation of monoclonal antibodies, rabbit hybridoma technology has also recently become available. Rabbits are believed to be more effective than mice for generation of high selectivity antibodies against small haptens, thus rabbit monoclonal antibodies may prove to be a better approach for generating the high selectivity and affinity desired for this application. Also, recombinant single chain antibodies, may be generated using the in vitro combinatorial evolution and display methods previously published (Breitling, F., Dubel, S., 1999; Schaffitzel, C., Hanes, J. et al., J Immunol Methods, 1999, 231:119-35). Examples of the preparation of recombinant antibodies are described in U.S. Pat. Nos. 5,693,780; 5,658,570; 5,876,961 (fully incorporated by reference herein).

In order to help elicit an immune response, bovine serum albumin (BSA) and keyhole limpet hemocyanin (KLH) may be used as carrier proteins for conjugation of the PAP antigen. KLH antigens generally elicit a stronger immune response in mammals, but also tend to be less soluble than BSA conjugates (Harlow, E. L., D., 1999). Donor products with an adenine ring such as ADP and PAP may be attached to both carrier proteins via the C2, C8 and N6 amino group of adenine. Donor products with a uridine ring can be conjugated via the C5 or C6 position of uridine. Either type of nucleotide may be conjugated through the ribose 2' and 3' hydrorxyls.

Conjugation Methods

The hapten conjugation chemistries used by the invention are well described single or two step synthetic approaches that have been used extensively for conjugating nucleotides for generation of immunogens or for immobilizing them on solid supports (Brodelius, P., Larsson, P. O. et al., Eur J Biochem, 1974, 47:81-9; Lindberg, M. and Mosbach, K., Eur J Biochem, 1975, 53:481-6; Camaioni, E., Boyer, J. L. et al., J Med Chem, 1998, 41:183-90). Most of the starting materials are commercially available, or can be obtained through custom synthesis, and it is understood that the reactions may proceed in good yield. These conjugation methods are described in the Examples in further detail. It is envisioned that the present invention may encompass but may not be limited by the hapten conjugation chemistries described herein. It is also envisioned that about 8-10 different antigens may be synthesized in all. Some antigens will have very short linkers such as C2 or C3 that will sterically minimize the accessibility of the base and others will have longer six carbon linkers that will allow more flexible presentation of the antigen.

Synthesis and Purification of Detectable Tags

In general, an FPIA detectable tag molecule can be divided into three different structural components: the antigen, the fluorophore, and the linker used to join them; an additional key structural variable is the site of attachment of the linker to the antigen. It is understood by one skilled in the art that suitable antigens, fluorophores and linkers are not limited to what is specifically described herein. However, in a suitable aspect of this invention, the same donor product-linker molecules that are used for conjugation to carrier proteins may be used for conjugation to several reactive fluorophore derivatives. The use of a range of reactive fluorophores may introduce additional structural diversity in the linker region. For instance, fluorescein succinimidyl esters are available with different length spacer arms, and DTAF (4,6-Dichlorotriazinylaminofluorescein) contains a bulky planar substituent adjacent to the site of attachment. Briefly, various donor product-linker molecules with reactive termini such as amino groups may be reacted with amine-reactive fluorophore derivatives and the resulting donor product-fluorophore conjugates may be tested for antibody binding affinity and changes in fluorescence polarization.

Purification of detectable tags can be performed by thin layer chromatography (TLC). TLC is used to separate reaction products because it allows several separations to be run in parallel, permits identification of fluorescent products by visualization and, provides sufficient quantities of fluorescent conjugates for thousands of binding assays in a single chromatography run. Thus, for pilot studies on fluorescent detectable tag molecules, TLC is superior to alternative separation methods like HPLC. Upon completion of the chromatography and elution of the donor product-fluorophore conjugates, the conjugates may be analyzed for intensity, basal polarization (absence of antibody), stability, binding to antibodies, and competition by unlabeled donor product and donor molecule, as described below.

Parameters Affecting the Antibody-Detectable Tag Interaction

In order to create the most sensitive assay method for detecting, quantifying, and screening products of group transfer methods, the parameters affecting the affinity of the antibody-detectable tag interactions is carefully monitored. Often, the cost of the enzyme is the limiting factor in an HTS assay. In general, it is desirable to have an antibody capable of detecting donor product at a concentration of 1 µM or lower. This allows the use of relatively small amounts of enzyme to produce a detectable amount of donor product within a practical time period of 0.5 to 4 hours.

Most antibody-antigen interactions with either polyclonal or monoclonal antibodies have a $K_d$ between 1 nM and 1 µM (Harlow, E. L., D., 1999), which is suitable for the above enzymatic detection parameters. The kinetics of the antibody-detectable tag interaction is a secondary consideration. If the donor product can displace the detectable tag rapidly enough, the FPIA can be used to monitor enzyme activity continuously in real time. This can be advantageous for some applications such as detailed kinetic studies. Also, obtaining screening data that includes time dependence can help to eliminate false positives resulting from autofluorescent compounds.

Furthermore, the difference in polarization of the probe in the free and bound states defines the total "spread" or dynamic range for the assay. A change of less than 50 mP may be sufficient for semi-quantitative detection of enzyme activity, but a change of 100 mP or greater may provide both much greater flexibility in designing the assay format, and more quantitative kinetic information. (It should be noted that improvements in instrumentation may soon make it possible to accurately detect very small changes in polarization.) Accordingly, polarization is proportional to molecular volume, and the change in effective volume upon binding of an antibody (150 kDa) to a small molecular weight fluorophore may be expected to cause an increase of at least 300 mP. However, there are other factors that can affect the observed polarization of both the free and bound detectable tag, such as, the fluorophore is attached to PAP by a flexible spacer arm. Thus, their maximum polarization is a function of the extent to which antibody binding decreases the mobility of the spacer and fluorophore; detectable tag "propeller effects" can lead to relatively low polarization values even for protein-bound fluorophores.

An additional consideration is whether there may be changes in the intensity of the fluorophores upon binding to receptor, including quenching from amino acid functional groups with overlapping spectra. Polarization is independent of fluorescence intensity (Owicki, J. C., J Biomol Screen, 2000, 5:297-306); however, because it is a ratio of intensity measurements taken in two planes, significant quenching may affect the antibody detectable tag interaction and result in decreased assay sensitivity. The changes in the fluorescence properties of a detectable tag when it becomes bound by antibody are a function of both interacting molecules and are difficult to predict. Thus, it is envisioned that different antibodies and detectable tag molecules will be tested in a matrix fashion. Further optimization of the detectable tag structure or the assay buffer to limit mobility of the bound detectable tag or to reduce quenching is also envisioned.

Identification of the Optimal Antibody/Detectable Tag Pair(s)

In order to identify optimal antibody/detectable tag pairs, a diverse set of fluorescent derivatives and linkage chemistries are generally evaluated. The synthesis and purification methods described above result in the isolation of several fluorescent products per reaction, so that at least a hundred fluorescent conjugates may be evaluated, requiring thousands of individual FP assays. The homogenous nature of FP assays and the availability of multiwell instruments makes the screening efforts very rapid; the rate-limiting steps are usually synthesis and purification, not testing for antibody-detectable tag binding properties. The antibody/detectable tag testing may be carried out in a Tecan Ultra multiwell FP reader in Tris or phosphate buffer in the presence of a low concentration of carrier protein (0.01% Bovine Gamma Globulin) to prevent non-specific interactions. The initial screen involves looking for the following desirable properties: low polarization in the absence of antibody (<100 mP); high affinity binding to the anti-donor product antibodies ($K_d$<1 µM); maximal difference in polarization between the bound and free states (ΔmP>100 mP); minimal fluorescence quenching upon binding antibody; selectivity for donor product (i.e., competitive displacement by donor product and not by donor molecule; rapid association/dissociation kinetics; and lack of interaction with other assay components.

Applicability of the Invention

The methods of the invention, as described in the examples below can be used as a measure of enzymatic activity in group transfer reactions. The methods are of particular importance in the pharmaceutical industry since they enable the analysis of group transfer enzymes in high throughput screening laboratories, e.g. for identification of drugs that can act as enzymatic modulators, especially inhibitors, and for determining how potential drug molecules are metabolized.

There is an increasing number of group transfer enzymes that are being targeted for the development of new therapeutics. Kinases are currently of highest interest, but SULTs, UGTs, ATPases, GTPases, methyltransferases, acetyltransferases, and ADP-ribosyltransferases are also being targeted. As this list increases it will become impractical and extremely expensive to use specific tests for each enzyme, or for small subgroups of enzymes that modify the same acceptor substrate. The assays and kits of the present invention allow for the detection of all of the enzymes in a given group transfer enzyme family and provide a common end point detection system for all of them. This allows for greater ease of use, particularly in high throughput screening laboratories, where robots can be set up with all the detection reagents and the various group transfer enzymes and potential substrates or inhibitors of interest can be tested in a matrix fashion.

In addition, the involvement of group transfer reactions in the conjugative metabolism of drugs and other xenobiotics is an important determinant in their pharmacodynamics, pharmacokinetics and side effects. In this regard, the assays and kits of the present invention allow for the screening of potential drug molecules with SULTs, UGTs, GTPases, ATPases, methyltransferases and acetyltransferases in an HTS format. There are many different xenobiotic conjugating isoforms, and because of the generic nature of the method, the kits of the present invention would greatly simplify their testing in a matrix fashion.

Thus, the general methods of the invention may be applied to a variety of different group transfer-related enzymatic processes, such as steroid hormone biosynthesis and function, xenobiotic metabolism, enzyme receptor regulation, and signal transduction in an effort to contribute to an integrated drug discovery approach discussed below.

Protein Kinases in Drug Discovery

Protein kinases catalyze the transfer of the terminal phosphate group from ATP or GTP to serine, threonine or tyrosine residues of acceptor proteins. They comprise one of the largest protein families in the human genome with more than 400 members (Kostich, M., English, J. et al., Genome Biol, 2002, 3:RESEARCH0043; Manning, G., Whyte, D. B. et al., Science, 2002, 298:1912-34; Hanks, S. K., Genome Biol, 2003, 4:111). In the broadest sense, they can be divided into serine/threonine or tyrosine kinases and soluble enzymes or transmembrane receptors. In the most recent and comprehensive genomic analyses, 428 human kinases were identified that comprise eight different homology groups, which also reflect differences in substrate specificity, structure/localization and/or mode of regulation (Hanks, S. K., Genome Biol, 2003, 4:111). For instance, there are 84 members of the Tyrosine Kinase group, which includes both transmembrane growth factor receptors such as EGFR and PDGFR and soluble enzymes such as the Src kinases, 61 members of the cyclic nucleotide dependent group, ser/thr kinases which include the PKC isoforms, and 45 members of the "STE" group, which includes the components of the mitogenic MAP kinase signaling pathway (Hanks, S. K., Genome Biol, 2003, 4:111).

Kinases are ubiquitous regulators of intracellular signal transduction pathways, and as such have come under intense focus by pharmaceutical companies searching for more selective therapies for a broad range of diseases and disorders (Cohen, P., Trends Biochem Sci, 2000, 25:596-601; Sridhar, R., Hanson-Painton, O. et al., Pharm Res, 2000, 17:1345-53; Cohen, P., Nat Rev Drug Discov, 2002, 1:309-15), especially cancers. Site specific protein phosphatases can catalyze the removal of phosphates from proteins, so that a tunable covalent modification cycle modulates protein function (Sridhar, R. et al., Pharm Res, 2000, 17:1345-53). Intracellular targets for phosphorylation include other kinases, transcription factors, structural proteins such as actin and tubulin, enzymes involved in DNA replication and transcription, protein translation, and metabolic enzymes (Cohen, P., Trends Biochem Sci, 2000, 25:596-601). Phosphorylation can cause changes in protein catalytic activity, specificity, stability, localization and association with other biomolecules. Simultaneous phosphorylation at multiple sites on a protein, with different functional consequences, is common and central to the integration of signaling pathways (Cohen, P., Trends Biochem Sci, 2000, 25:596-601).

The Kinase HTS Bottleneck

Recent clinical successes with small molecule kinase inhibitor drugs, most notably Gleevec, a BCR-Abl inhibitor used to treat non-Hodgkins lymphoma, and Iressa, an EGFR kinase inhibitor used for a number of solid tumors, has generated intense interest in the kinase family (Dancey, J. and Sausville, E. A., Nat Rev Drug Discov, 2003, 2:296-313). However, the ability to validate and pursue new kinases for drug discovery is being hampered by a lack of screening assays capable of accommodating diverse kinase isoforms. Most kinase assay methods rely on detection of a tagged phosphopeptide, and significant development or optimization is required to accommodate new peptide sequences. Protein kinases recognize specific linear sequences of their target proteins that often occur at beta bends. In general, amino acids that flank the phosphorylated residue for three to five residues on either side define a phosphorylation site. The Phospho.ELM database, which compiles known kinase phosphorylation sites, contains entries for 195 eukaryotic kinases (mostly human), less than half of the total kinases. Moreover, most, if not all of these specificity profiles are incomplete. Though there is significant overlap in substrate specificity among related kinases, there is no consensus sequence that is phosphorylated by a large number of kinases (Ross, H., Armstrong, C. G. et al., Biochem J. 2002, 366:977-81). The time and money required to develop phosphopeptide-based assay methods for kinases with novel recognition sequences is slowing the identification of selective inhibitors for validating new kinase targets or as potential lead molecules.

The assay development bottleneck extends further downstream in the discovery process as well. There is a great deal of structural similarity between kinase active sites, and a significant effort goes toward identifying the most selective inhibitors to minimize side effects from off-target activity. At some point following a primary screen, secondary screens are often run against a panel of 10-100 kinases to obtain selectivity profiles for the most promising hits. These profiling studies generally include potency determinations for compounds where significant off-target activity is observed. The available nonradioactive HTS assay methods are not suitable for quantitative assays with a broad spectrum or kinases, and studies have shown that there are significant differences in the identity and potency of hits determined with different HTS assay methods (Sills, M. A. et al., J Biomol Screen, 2002, 7:191-214). For these reasons, the bulk of selectivity profiling is done using the traditional $^{33}$P-radioassays. Most pharmas contract this work out at significant expense and inconvenience to service providers who are willing to assume the regulatory and disposal requirements.

Glycosyltransferases in Drug Discovery

There are over 200 glycosyltransferases encoded in the human genome, and most use UDP-activated sugars as the donor (Nat Rev Drug Discov, 1:665-73). From a functional standpoint, the reactions they catalyze can be divided into three major types, biosynthesis of disaccharides or polymers such as starch or hyaluronan, posttranslational modification of proteins, and glucuronidation of small molecules, including endogenous hormones and xenobiotics (Chene, P., Nat Rev Drug Discov, 2002, 1:665-73). All three types of glycosyltransferases are of interest in drug discovery. The role of the approximately 15 hepatic UDP-glucuronosyltransferases in drug metabolism has been an area of focus for several years (Tukey, R. H. and Strassburg, C. P., Annu Rev Pharmacol Toxicol, 2000, 40:581-616; Kiang, T. K., Ensom, M. H. et al., Pharmacol Ther, 2005, 106:97-132). More recently, protein glycosyltransferases and those involved in synthesis of biolypolymers have come under focus as therapeutic targets, for cancer (Dwek, M. V. and Brooks, S. A., Curr Cancer Drug Targets, 2004, 4:425-42; Fuster, M. M. and Esko, J. D., Nat Rev Cancer, 2005, 5:526-42) (Table 2) and lysosomal storage diseases (Butters, T. D., Mellor, H. R. et al., Philos Trans R Soc Lond B Biol Sci, 2003, 358:927-45). Bacterial glycosyltransferases involved in cell wall synthesis are also being targeted for development of new anti-infectives (Zawadzke, L. E., Wu, P. et al., Anal Biochem, 2003, 314:243-52; Kim, J., Felts, S. et al., J Biomol Screen, 2004, 9:375-81).

Glucuronidation of Drugs

Aside from P450-depedent oxidation, glucuronidation is the most important route of hepatic drug metabolism (Rowlands, M. G. et al., Anal Biochem, 2004, 327:176-83). Glucuronidation usually facilitates excretion of drugs by increasing their aqueous solubility, but in some cases it increases drug activity. A broad spectrum of drugs are eliminated or activated by this route, including non-steroidal anti-inflammatories, opioids, antihistamines, antipsychotics and antidepressants (Tukey, R. H. et al., Annu Rev Pharmacol Toxicol, 2000, 40:581-616; Kiang, T. K. et al., Pharmacol Ther, 2005, 106:97-132). Pharmaceutical companies have an immediate need for better methods to determine whether their potential drug candidates will be glucuronidated, and if so by which UGT isoform. The current state of the art is isolation and detection of glucuronides from in vitro enzymatic reactions using LC/MS, a method not suited for profiing large numbers of compounds. Fluorescent probe substrates and assay methods for detecting glucuronidation have been developed but have not been widely adapted because they cannot be used with all UGT isoforms (Broudy, M. C., CL; Patten, CJ, Trubetskoy, O. V. and Shaw, P. M., Drug Metab Dispos, 1999, 27:555-7).

Glucuronidation in Cancer

Glycans inside and outside the cell play significant roles at all pathophysiological stages of tumor development (Dwek, M. V. et al., Curr Cancer Drug Targets, 2004, 4:425-42; Fuster, M. M. et al., Nat Rev Cancer, 2005, 5:526-42). For example, hyaluronan, a polymer of repeating disaccharide units of D-glucuronic acid and N-aetylglucosamine, is an important component of the extracellular matrix that has been linked with many tumor-related activities including cell adhesion and motility, cell growth and differentiation, and angiogenesis (Adamia, S., Maxwell, C. A. et al., Curr Drug Targets Cardiovasc Haematol Disord, 2005, 5:3-14). Elevated levels of hyaluronan and hyaluronan synthase enzymes have been linked with high metastatic potential in prostate and breast cancer (Adamia, S. et al., Curr Drug Targets Cardiovasc Haematol Disord, 2005, 5:3-14), with tumor vascularization in prostate cancer (Simpson, M. A., Wilson, C. M. et al., Am J Pathol, 2002, 161:849-57) and with poor prognosis in multiple myeloma and ovarian cancer (Yabushita, H., Noguchi, M. et al., Oncol Rep, 2004, 12:739-43). N-acetylglucosaminyltransferase V is a protein glycosyltransferase that is overexpressed in many malignant cells (Fuster, M. M. et al., Nat Rev Cancer, 2005, 5:526-42). The resulting higher levels of β1,6-branched N-linked glycans on the cell surface proteins decreases cell-cell and cell-ECM interactions resulting in increased tumor cell motility and invasion across basement membranes (Guo, H. B., Lee, I. et al., Cancer Res, 2002, 62:6837-45).

Currently, efforts to identify glycosyltransferase inhibitors are largely dependent on assays that are specific for the glycosylated products, though more flexible methods have recently begun to emerge (Deng, C. and Chen, R. R., Anal Biochem, 2004, 330:219-26; Zhang, B. et al., Anal Biochem, 2005, 345:326-35). Because of the tremendous diversity in acceptor substrates and glycosylation sites, validation of glycosyltransferases as drug targets and identification and optimization of lead molecules will likely experience bottlenecks similar to those encountered with protein kinases.

Sulfotransferases in Drug Discovery

Sulfotransferase enzymes (SULTs) catalyze the conjugation of sulfonate groups onto a variety of xenobiotic and endogenous substrates primarily at hydroxyl groups to form a sulfate, but also at some aromatic amines resulting in sulfamate formation (Falany, C. N., Faseb J, 1997, 11:206-16). 3'-Phosphoadenosine 5'-phosphosulphate (PAPS) serves as the donor molecule for the activated sulfate. The product after sulfate transfer is the 3',5'-bisphosphate adenine ribonucleotide, known as phosphoadenosine phosphate (PAP).

There are two major classes of SULTs in humans that differ in solubility, size, subcellular distribution, and share less than 20% sequence homology (Hemmerich, S., Verdugo, D. et al., Drug Discov Today, 2004, 9:967-75). The 37 membrane bound enzymes are located in the golgi apparatus and sulfonate large endogenous molecules such as heparan, glycosaminoglycans, and protein tyrosines (Strott, C. A., Endocr Rev, 2002, 23:703-32). The 12 cytosolic sulfotransferases, conjugate small molecular weight xenobiotics and hormones. The golgi-associated sulfotransferases are being targeted for cancer and inflammation because they play roles similar to glycosyltransferases in cell-cell and cell-matrix interactions (Hemmerich, S. et al., Drug Discov Today, 2004, 9:967-75).

Xenobiotic Sulfation

Sulfation is the second most prevalent form of conjugative metabolism after glucuronidation (Glatt, H., Chem Biol Interact, 2000, 129:141-70; Coughtrie, M. W. and Johnston, L. E., Drug Metab Dispos, 2001, 29:522-8; Parkinson-A, Casaret & Doull's Toxicology, Sixth Edition, 2001, 133-224); together these two reactions account for more than two-thirds of total conjugative xenobiotic metabolism (Evans, W. E. R., M. V., Science, 1999, 286:487-491). Moreover, there is significant genetic variability in SULT genes, with functional consequences. Non-synonymous polymorphisms (i.e., mutations that result in a change in amino acid sequence) have been identified in more than half of the xenobiotic metabolizing SULTs (Carlini, E. J., Raftogianis, R. B. et al., Pharmacogenetics, 2001, 11:57-68; Freimuth, R. R., Eckloff, B. et al., Pharmacogenetics, 2001, 11:747-56; Thomae, B. A., Eckloff, B. W. et al., Pharmacogenomics J, 2002, 2:48-56; Adjei, A. A., Thomae, B. A. et al., Br J Pharmacol, 2003, 139:1373-82; Thomae, B. A., Rifki, O. F. et al., J Neurochem, 2003, 87:809-19), and many of these result in differences in enzyme activity levels, stability, or other properties (Carlini, E. J. et al., Pharmacogenetics, 2001, 11:57-68; Freimuth, R. R. et al., Pharmacogenetics, 2001, 11:747-56; Thomae, B. A. et al., Pharmacogenomics J, 2002, 2:48-56; Adjei, A. A. et al., Br J Pharmacol, 2003, 139:1373-82; Thomae, B. A. et al., J Neurochem, 2003, 87:809-19) with potential clinical relevance. For example, homozygous expression of the SULT1A1*2 allele has recently been linked with a three-fold increased risk of death in breast cancer patients receiving tamoxifen (Nowell, S., Sweeney, C. et al., J Natl Cancer Inst, 2002, 94:1635-40). The high frequency of functionally significant SULT polymorphisms and their association with differences in drug response highlights the need for implementing a pharmacogenomic approach for drug metabolism by sulfation. Recombinant SULT isoforms have been expressed and purified, and could be used to screen diverse molecules for sulfation; however, flexible HTS methods are not available.

Regulation of Hormones by Sulfation

Intertwined with its role in drug metabolism, sulfation also reversibly regulates the activity of many endogenous signaling molecules, including steroid hormones and catecholamines, that are involved in the pathology of diseases such as breast cancer (Chemite, G. S, and Pasqualini, J. R., J Steroid Biochem Mol Biol, 2001, 76:95-104; Adjei, A. A. and Weinshilboum, R. M., Biochem Biophys Res Commun, 2002, 292:402-8), cardiovascular disease (Merten, M., Dong, J. F. et al., Circulation, 2001, 103:2032-4; Song, C., Hiipakka, R. A. et al., Steroids, 2001, 66:473-9), and depression (Plassart-Schiess, E. and Baulieu, E. E., Brain Res Brain Res Rev, 2001, 37:133-40). For instance, estrogen sulfoconjugates are the main circulating forms of the hormone, and they require desulfation in the cell in order to bind and activate the estrogen receptor (Raftogianis, R., Creveling, C. et al., J Natl Cancer Inst Monogr, 2000, 113-24). The involvement of sulfation in disease pathology and drug metabolism raises the potential for unintended interactions between drugs and hormones competing for the same sulfotransferase and underscores the importance of HTS assay methods for delineating the selectivity of the SULTS during drug discovery.

ATPases in Drug Discovery

Adenosine triphosphatases (ATPases) are a class of enzymes that catalyze the decomposition of adenosine triphosphate (ATP) into adenosine diphosphate (ADP) and a free phosphate ion. This dephosphorylation reaction releases energy, which the enzyme (in most cases) harnesses to drive other chemical reactions that would not otherwise occur. This process is widely used in all known forms of life.

ATPase activity is associated with many different types of proteins, including molecular chaperones, myosin, kinesins, and transporter proteins where the ATP hydrolysis makes the overall reaction thermodynamically favorable (Chene, P., Nat Rev Drug Discov, 2002, 1:665-73; Xie, Z. et al., Front Biosci, 2005, 10:3100-9). Disruption of microtubule function and/or assembly is one approach that is being pursued for development of anticancer agents (Pellegrini, F. et al., Cancer Invest, 2005, 23:264-73), For example, agents that interfere with mitotic kinesin motor proteins such as Eg5 are currently in clinical trials (DeBonis, S. et al., Mol Cancer Ther, 2004, 3:1079-90; Pellegrini, F. et al., Cancer Invest, 2005, 23:264-73). Current molecular screening efforts are focused largely on identification of compounds that bind at the ATP binding site and inhibit hydrolysis. The molecular chaperone Hsp90 with its associated ATPase has emerged as an important drug target for cancer as well. Hsp90 is required for the proper folding and stability of a number of oncogenic 'client' proteins, including c-Raf-1, cdk4, ErbB2, and c-Met, so its inhibition could block multiple tumorigenic pathways (Workman, P., Curr Cancer Drug Targets, 2003, 3:297-300). HSP 90 inhibitors are currently in clinical trials, and efforts to identify new drug candidates that inhibit its ATPase activity are ongoing (Rowlands, M. G. et al., Anal Biochem, 2004, 327:176-83). However, these efforts are being hampered by the lack of robust HTS methods for ATPases, most of which rely on phosphate detection with its attendant problems of low sensitivity and high background in biological samples (Funk, C. J., Davis, A. S. et al., Anal Biochem, 2004, 329:68-76; Rowlands, M. G. et al., Anal Biochem, 2004, 327:176-83).

GTPases in Drug Discovery

Guanine triphosphatases (GTPases) are a large family of enzymes that can bind and hydrolyze GTP. The GTP binding and hydrolysis takes place in the highly conserved G domain common to all GTPases. GTPases play an important role in: signal transduction at the intracellular domain of transmembrane receptors, including recognition of taste, smell and light. GTPases are also involved in protein biosynthesis at the ribosome; control and differentiation during cell division; and translocation of proteins through membranes.

More specifically, ligand activated G-protein coupled receptors (GPCR) are the most frequently screened target class in drug discovery. They interact with heterotrimeric G-proteins, catalyzing GTP loading and liberation of beta-gamma subunits. Signal termination is effected by the intrinsic GTPase activity of the G-alpha subunit, which can be accelerated by regulators of G-protein (RGS) proteins (McCudden, C. R., Hains, M. D. et al., Cell Mol Life Sci, 2005, 62:551-77). Biochemical assays for G-proteins include measurements of GTP binding, GTP hydrolysis, and interaction with RGS proteins (Kimple, R. J. et al., Comb Chem High Throughput Screen, 2003, 6:399-407; Willard, F. S., Kimple, R. J. et al., Methods Enzymol, 2004, 389:56-71). Small G proteins, such as Ras, Rho regulate a variety of signaling events and are implicated in numerous cancers (Rojas, R. J., Kimple, R. J. et al., Comb Chem High Throughput Screen, 2003, 6:409-18). These proteins also have intrinsic GTPases that attenuates signaling, and measurement of this activity is one method used for their detection in screening applications. As in the case of ATP hydrolysis, the non-radioactive detection methods used for GTP hydrolysis are problematic for HTS because of their lack of sensitivity, low signal to noise, and potential for interference from test compounds. A simple, fluorescent detection method for GDP produced would provide a robust HTS assay method that would be applicable across the entire GPCR family.

It is envisioned that the FPIA-based donor product assay of the invention will be used to screen drug libraries for inhibitors or activators of kinases, glycosyltransferases, sulfotransferases, methyltransferases, acetyltransferases, ATPases, GTPases, 5'-nucleotidases and thymidylate 5'-phosphatases. It will also be useful for screening peptides, proteins or other molecules as acceptor substrates for any or all of these enzyme classes. In these applications, it will have the significant advantages over other methods such as the universal nature of the assay, simplified homogenous assay, no radioactivity, and the ability to quantify enzyme turnover.

Universal Assay Method

This method will accelerate the incorporation of the aforementioned enzymes, such as protein kinases into HTS screening programs because it is truly generic. For example, a single set of detection reagents can be used for all kinases and all acceptor substrates. An important advantage over most of the current assay methods is the capability to use physiological protein acceptor substrates as well as short peptides.

Homogenous

This assay is a single addition, mix and read format. This is an important factor driving decisions on assay selection in an automated high throughput environment (High Tech Business Decisions, M., CA, Commisioned Market Analysis, 2002). In addition, if antibodies with suitable binding kinetics are isolated, it allows a continuous assay format that provides more detailed kinetic information than a stop-time assay.

Fluorescence Detection

By employing fluorescent probes, the FPIA format eliminates radiation handling, disposal and costs. It should be noted that over the last few years FP has become one of the key HTS assay platforms used by pharma (Owicki, J. C., J Biomol Screen, 2000, 5:297-306). It is expected that in 2003 it will be used by pharma in approximately 12% of total primary screening assays; this is a doubling from the level of FP usage in 2001 (High Tech Business Decisions, M., CA, Commisioned Market Analysis, 2002). FP is a standard mode on several commercial HTS plate readers.

Quantitative

In the enzymatic assay of the invention, the donor product, for example, ADP is produced in stoichiometric amounts with the phosphorylated peptide or protein. Thus the use of a standard curve for ADP will allow a direct measure of enzyme turnover. Though the use of FP for HTS applications is a relatively recent development, the use of FPIAs for quantitative detection of hormones and metabolites in a diagnostic setting is very well established (Nasir, M. S. et al., Comb Chem High Throughput Screen, 1999, 2:177-90).

EXAMPLES

Example 1

Uridine Glucuronide Transferase Assay

Figure 2:
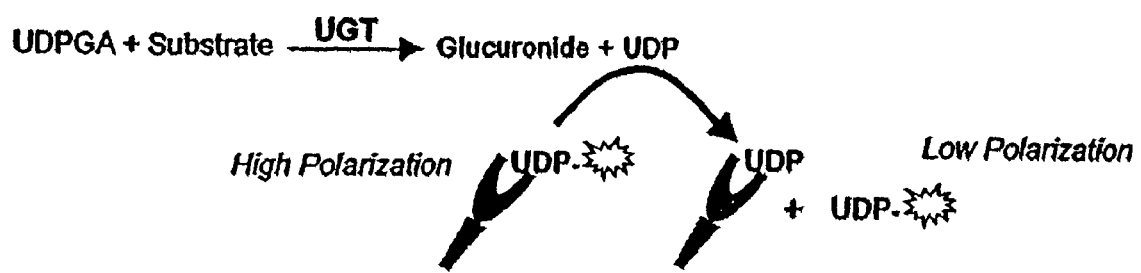
FIG. 2 illustrates use of FPIA to detect and quantify UDP formation, the donor product of the UGT reaction.
Figure 3:
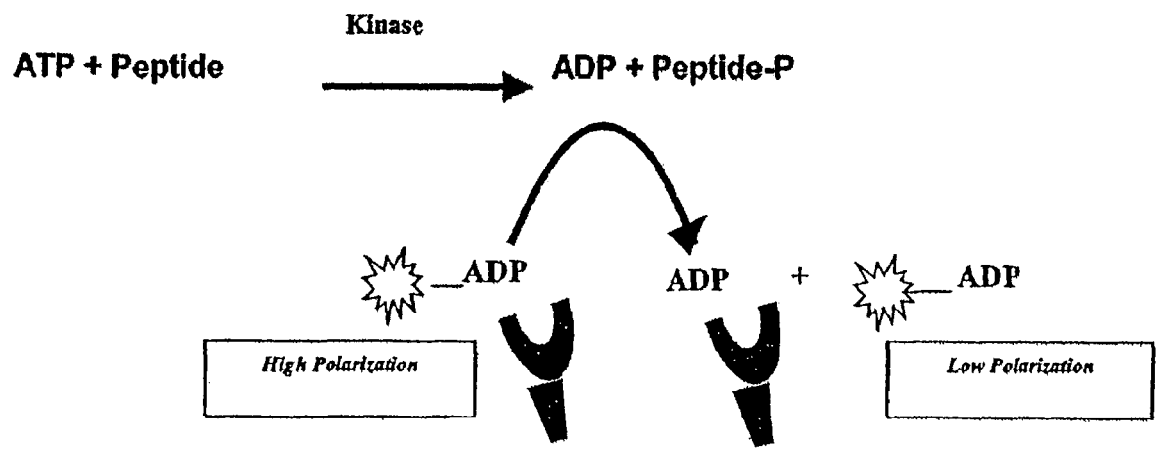
FIG. 3 illustrates use of FPIA to detect and quantify ADP formation, the donor product of the kinase reaction.

One embodiment of this application involves detecting the "donor product" of the UGT reaction using a competitive fluorescence polarization immunoassay where the antibody-bound tracer has a high polarization value which decreases when it is displaced by an analyte, such as UDP (as shown in FIG. 2). The main reagent required for this assay is the production of an antibody that binds UDP with high selectivity and has negligible binding to the donor, UDP-glucuronic acid (UDPGA). This highly selective antibody is used in combination with fluorescent UTP compounds (as substitutes for UDP tracers) to establish the assay. The polyclonal antibody produced against UDP required covalent binding of the nucleotide hapten to a carrier protein. UTP was used as the hapten only because reactive derivatives of the triphosphate, but not the diphosphate, were readily available that could be used for conjugation. It was reasoned that the majority of the triphosphate may be hydrolyzed to di- and mono-phosphate in animals. Several different chemistries for linking the UTP to carrier protein were investigated, because the nature of the linkage can have a profound affect on the resulting antibody specificity and affinity for antigen. Care was taken so that the linker molecule was attached to the uridine ring rather than the ribose or phosphate, thus maximizing the immunoreactivity with the portion of the UDP molecule that may differentiate it from the donor, UDPGA. One immunogen that proved particularly useful was 5-aminoallyl UTP (Sigma) conjugated to Keyhole Limpet Hemocyanin using glutaraldehyde.

Figure 4:
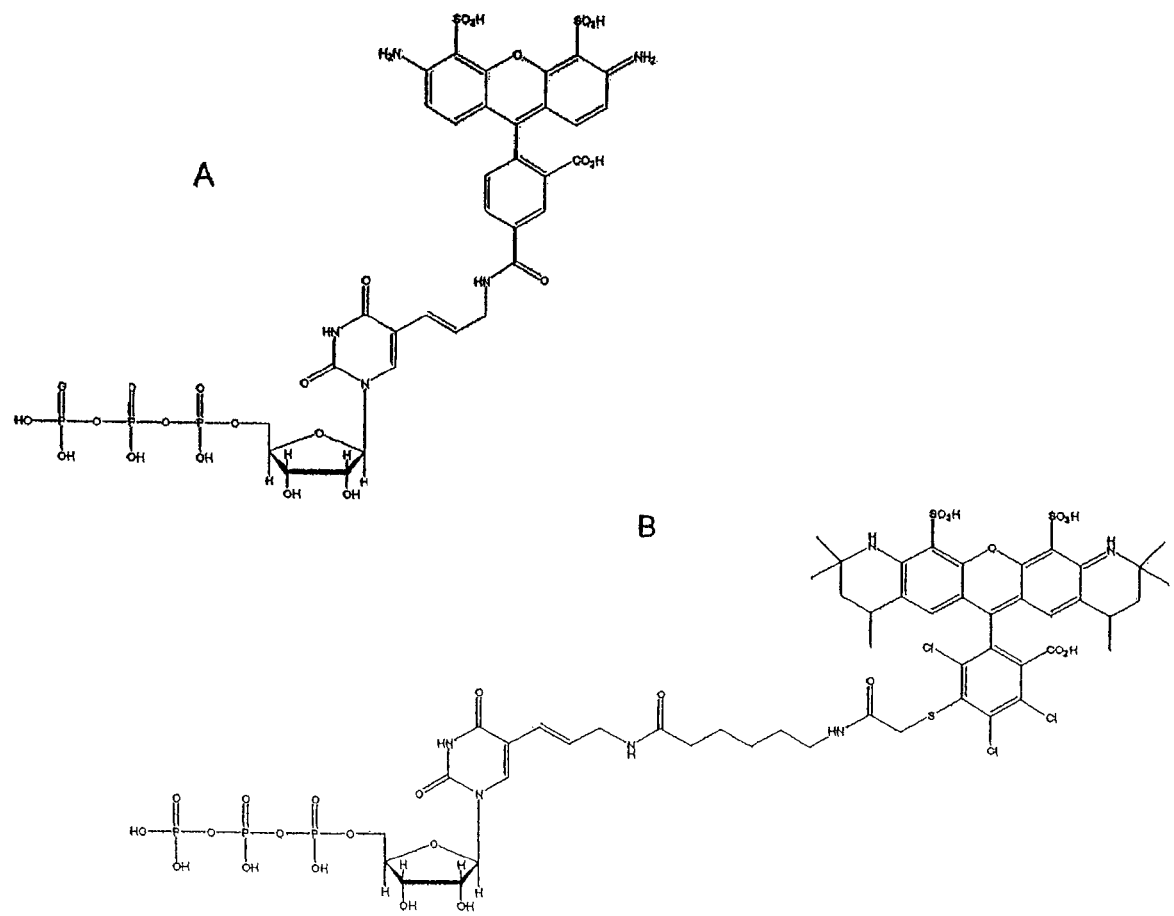
FIGS. 4 A-B depict examples of suitable tracers used to quantify UDP formation.

Tracers were synthesized in a manner similar to immunogens, by conjugating amine-reactive fluors to 5-aminoallyl UTP. Tracers based on fluorescein derivatives such as 5-and 6-fluorescein amine proved useful, but those based on the Alexa Fluors® (Molecular Probes) proved most suitable as they yielded higher polarization shifts when bound to antibody. Two such UTP tracers which can be used for UGT assay of the invention are shown in FIG. 4. Specifically, FIG. 4A depicts the chemical structure of Alexa Fluor® 488/aminoallyl-UTP and FIG. 4B depicts Alexa Fluor® 633/aminoallyl UTP. The structure of the allyl linker is an important component of the tracer because it reduces the flexibility of the linker region relative to single bonds, preventing rotation of the fluor and resultant lower polarization values for the bound tracer. Commercially available UTP tracers with alkynyl linkers (Molecular Probes, Corvallis, OR) have also worked well for the same reason. Applicants note that UTP was used for tracer synthesis for reasons of convenience because the aminoallyl derivative was commercially available. Tracers based on UDP have also been synthesized and have been shown to work equally well for the method of the invention, as would be expected.

Selectivity of the antibody for UDP

Figure 5:
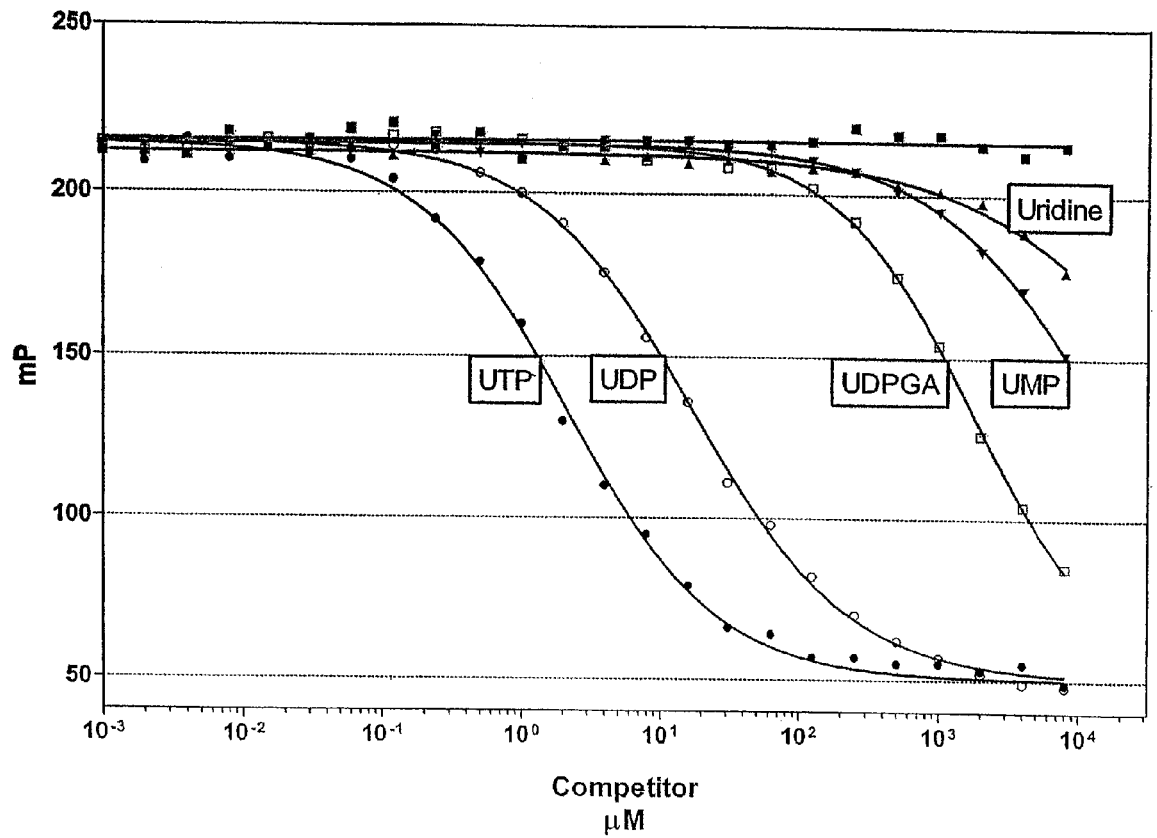
FIG. 5 shows titration or competitive displacement curves for uridine nucleotides using a polyclonal antibody raised against UDP/UTP and a commercially available tracer molecule (Alexa®-UTP).

To detect UGT catalytic activity a series of experiments were performed using the antibodies and tracers described above. For example, FIG. 5 shows titrations of antibody-tracer complex with various uridine nucleotides using polyclonal antibody raised against a mixture of UTP and UDP conjugated to KLH (UGT-1). The antibody and 2 nM of a commercially available Alexa® 488-5-aminoalkynyl-UTP molecule (Molecular Probes) were added to wells of a black multiwell plate (Thermo Labsystems Pt# 7605) containing the indicated amounts of uridine nucleotides in 50 mM KPO4 pH 7.5, 150 mM NaCl, 0.1 mg/ml BGG. Fluorescence polarization was read in a Tecan Ultra plate reader after several hours of equilibration at room temperature using a $Ex_{485}/Em_{535}$ filter set.

It is noted that UTP and UDP compete off the tracer with similar effectiveness, with half maximal values ($IC_{50}$) of 5 and 15 μM, respectively. In contrast, the donor molecule UDP-glucuronic acid (UDPGA) competes much less effectively, with an $IC_{50}$ of approximately 2 mM, indicating that this antibody is greater than 100× more selective for the reaction product UDP than the donor molecule, UDPGA using this displacement assay.

The crossreactivity with UTP was expected and is not problematic for the proposed assay because it is not present, nor is it produced, in UGT enzyme reactions. The ability of UDP to displace the tracer at low micromolar concentrations and the inability of UDPGA to do so indicates that this antibody is suitable for detection of UDP produced in UGT enzyme reactions.

Detection of UGT Catalytic Activity

Figure 6:
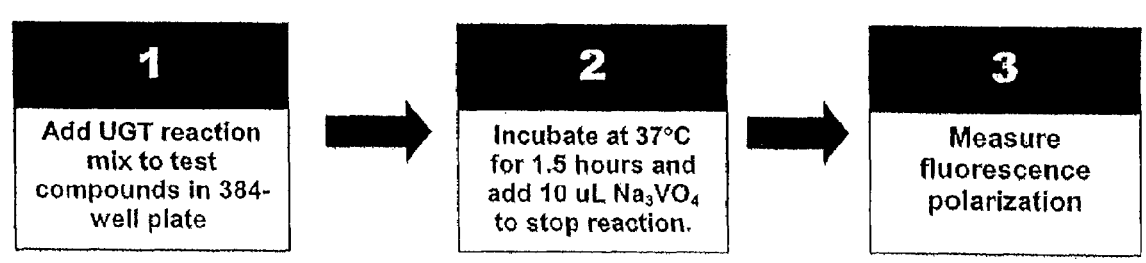
FIG. 6 shows standard UGT reaction conditions for detection of enzymatically generated UDP by competitive FPIA.
Figure 7:
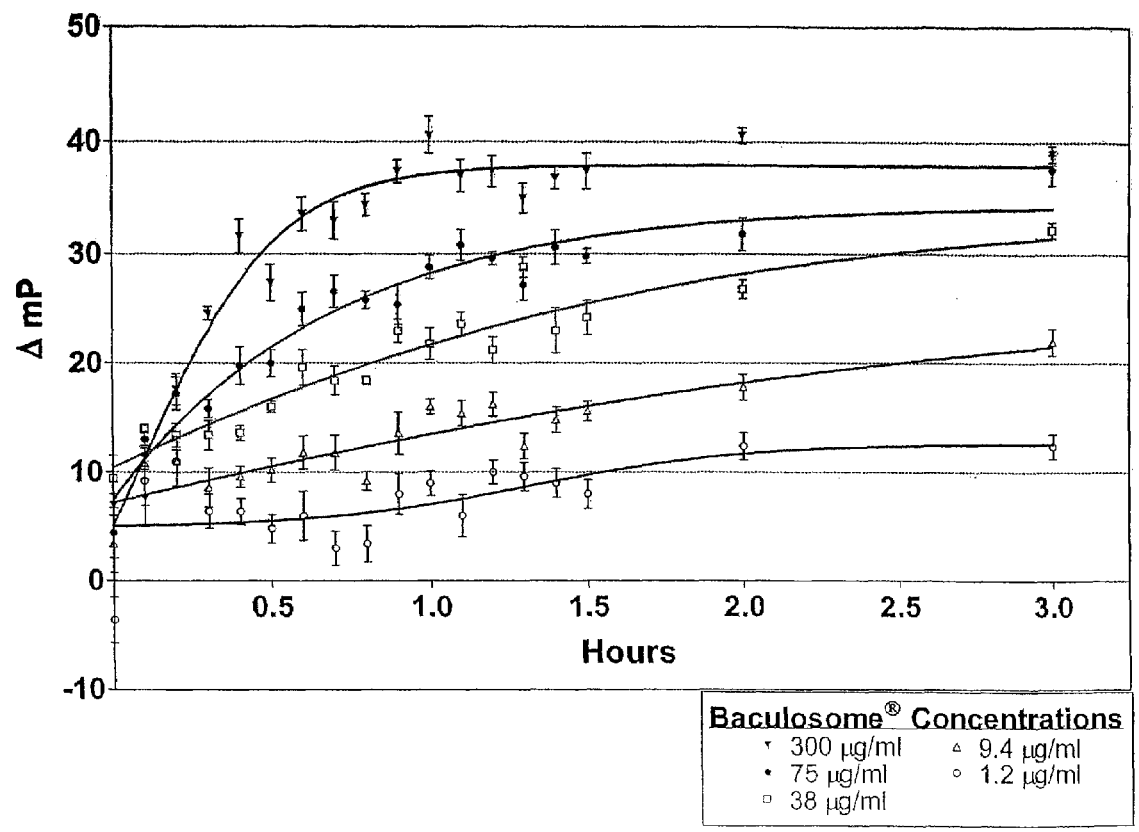
FIG. 7 shows the dependence of the FPIA-based UGT enzymatic assay on enzyme concentration and time.
Figure 8:
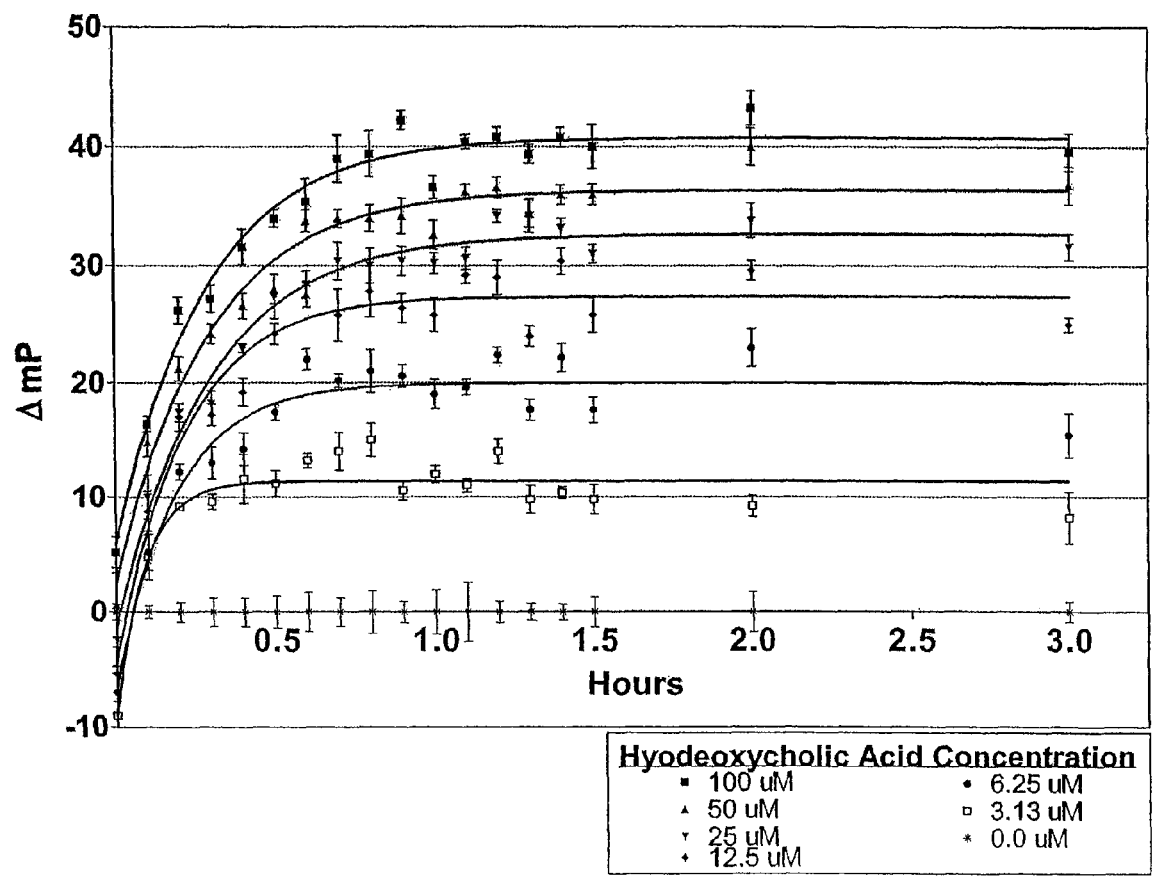
FIG. 8 shows the dependence of the FPIA-based UGT enzymatic assay on acceptor concentration.
Figure 9:
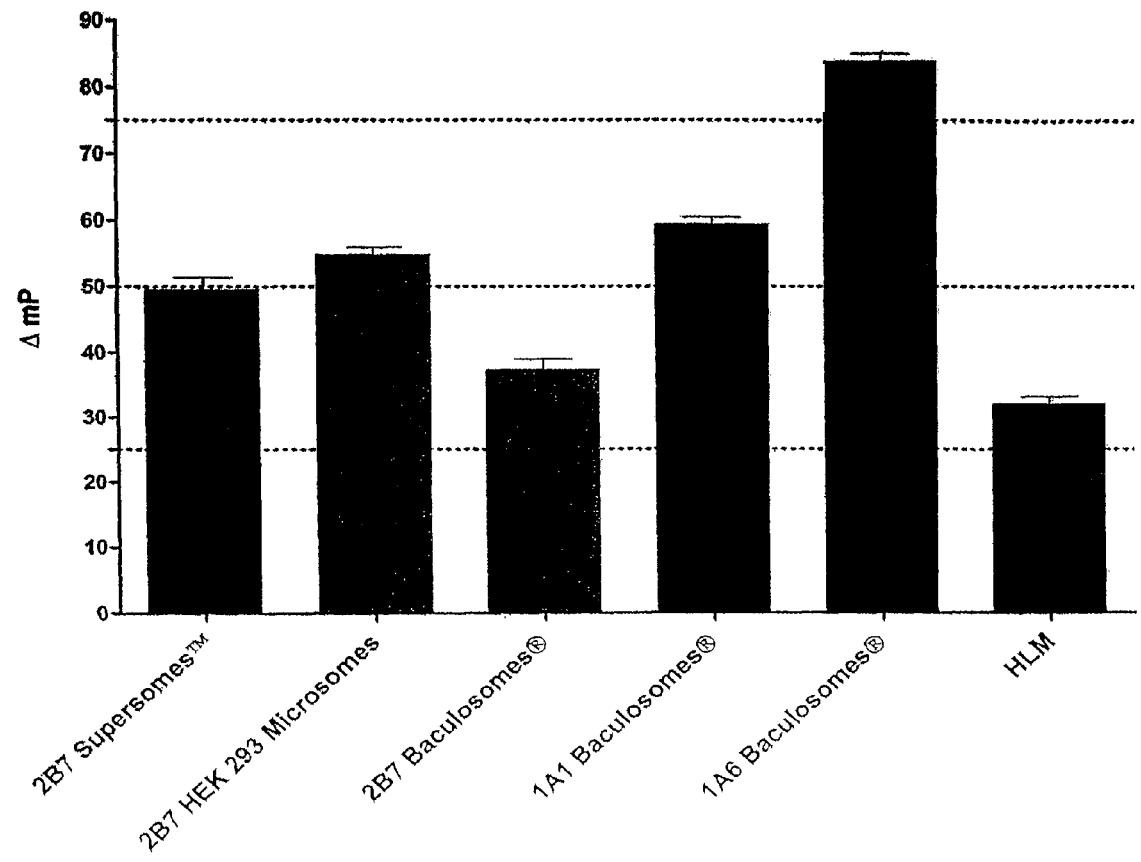
FIG. 9 shows use of the competitive FPIA for detection of UDP formation by diverse UGT isoforms and acceptor substrates.

To detect UGT catalytic activity, the assay protocol and the UGT reaction conditions set forth in FIG. 6 were followed. The experimental results of using the UGT-1 antibody and a UTP tracer for detection of UGT enzymatic activity in a multiwell format is shown in FIGS. 7-9. In these experiments a tracer synthesized from 5-aminoallyl UTP (Sigma), Alexa Fluor 488 (FIG. 4) and various commercially available sources of UGT enzymes were used. The dependence of the assay signal on time and UGT enzyme concentration is shown in FIG. 7. UGT assays were performed in 35 μl volumes with varying amounts of UGT 2B7 Baculosomes™ (Invitrogen), 100 μM hyodeoxycholic acid (HDCA), and 70 μM UDPGA in the present of the anti UDP/UTP Ab/tracer complex. The UTP tracer was synthesized in-house with AlexaFluor™ 488 (Molecular Probes). The standard assay buffer consisted of 50 mM $KPO_4$(pH 7.5), 150 mM NaCl, 5 mM $MgCl_2$, and 1% DMSO (v/v). Incubations were at 37° C. Δ mP=mP (reaction with acceptor)−mP (reaction without acceptor).

The dependence of the assay signal on acceptor substrate concentration is shown in FIG. 8. Similarly, UGT assays were performed in 35 μl volumes with 300 μg/ml of UGT 2B7 Baculosomes™ (Invitrogen), varying amounts of hyodeoxycholic acid (HDCA), and 70 μM UDPGA in the presence of the anti UDP/UTP Ab/tracer complex. The UTP tracer was synthesized in-house with AlexaFluor™ 488 (Molecular Probes). The standard assay buffer consists of 50 mM $KPO_4$ (pH 7.5), 150 mM NaCl, 5 mM $MgCl_2$, and 1% DMSO (v/v). Incubations were at 37° C. The experiments in FIGS. 7 and 8 were done with recombinant UGT 2B7 and hyodeoxycholic acid as an acceptor substrate.

FIG. 9 shows that the UGT assay can be used to detect glucuronidation of diverse acceptor substrates by different UGT isoforms, clearly illustrating the universal nature of the method. In this experiment a variety of UGT enzyme sources and acceptor substrates were tested in the UGT assay. The enzyme protein concentration and the acceptor substrate (@100 uM) for each of the reactions are as follows: 2B7 Supersomes™ (BD Biosciences)(50 ug/ml, HDCA), HEK293 2B7 microsomes (kind gift from Dr. Anna Radominska-Pandya)(50 ug/ml, HDCA), 2B7 Baculosomes™ (300 μg/ml, HDCA), 1A1 Baculosomes™ (300 μg/ml, octylgallate), 1A6 Baculosomes™ (300 μg/ml, 1-naphthol), and Human Liver Microsomes (HLM; XenoTech)(50 ug/ml, HDCA). It is noted that the reported AmP values are near the maxima achieved with a titration of enzyme; protein concentrations were based on vendor-supplied information.

Figure 10:
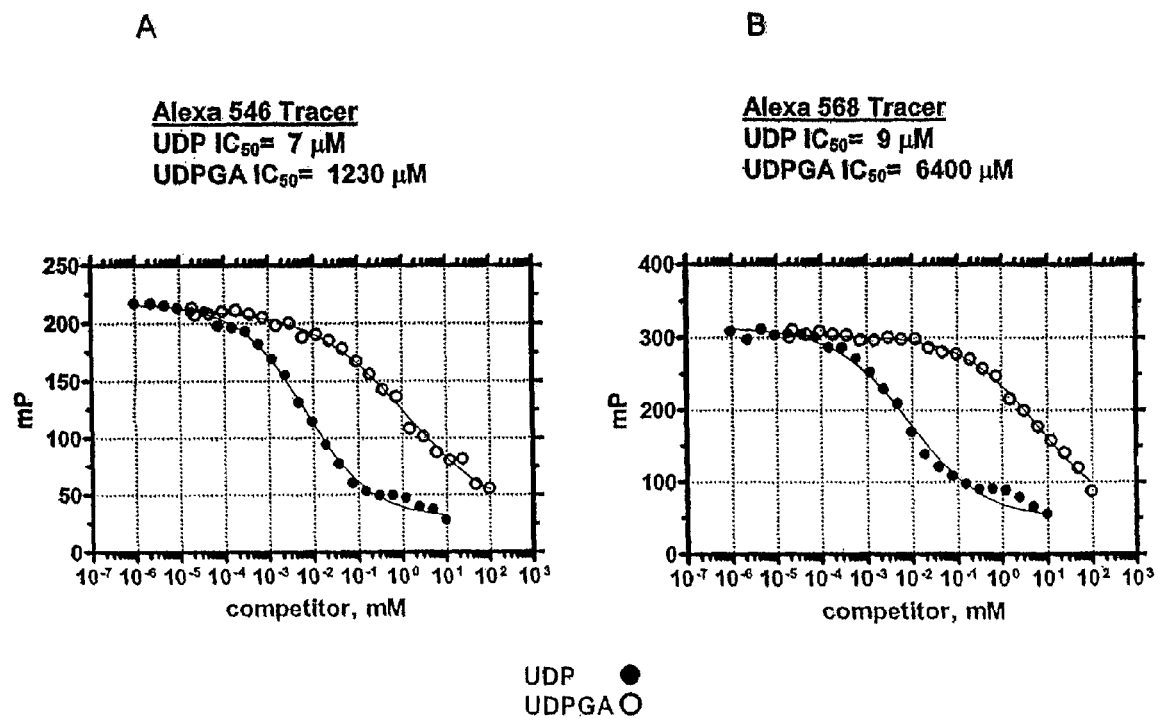
FIGS. 10 A-B show competitive displacement of two different Alexa Fluor®-UTP tracers from antibody by UDP and UDPGA.

Applicants further note that the ability of the antibody to selectively recognize low micromolar concentrations of UDP in the presence of UDPGA concentrations typically used for UGT assays —50-100μM —is important for achieving a low signal to background. Varying the structure of the immunogen, as mentioned above, is one way to change the relative binding properties of antibodies for UDP and UDPGA. Another way that is not as immediately obvious is to vary the tracer structure. The method depends on the relative ability of UDP and UDPGA to competitively displace the tracer from antibody, and it is reasonable to assume that not all tracers will show the same relative response to the two nucleotides. An example of such tracer effects is summarized in FIGS. 10 A and B. In this example, two different tracers are compared. The tracers are conjugates of 5-aminoallyl UTP to two different amine reactive Alexa Fluors®, one with an excitation peak of 546 and the other with an excitation of 568. Both of these tracers are displaced from antibody (anti-UDP rabbit polyclonal Ab or UGT-1) in a similar manner by UDP. $IC_{50}$ values of 7 and 9μM were observed for the Alexa® 546 and Alexa® 568 tracer, respectively. However, displacement by UDPGA differs significantly for the two tracers, with $IC_{50}$ values of 1.2 and 6.4mM observed for the Alexa® 546 and Alexa® 568 tracer, respectively. Thus, the signal to background of the UGT assay with a given antibody can be enhanced by identifying tracers that are displaced by UDP more effectively than UDPGA.

Signal stabilization and reaction quenching

Figure 11:
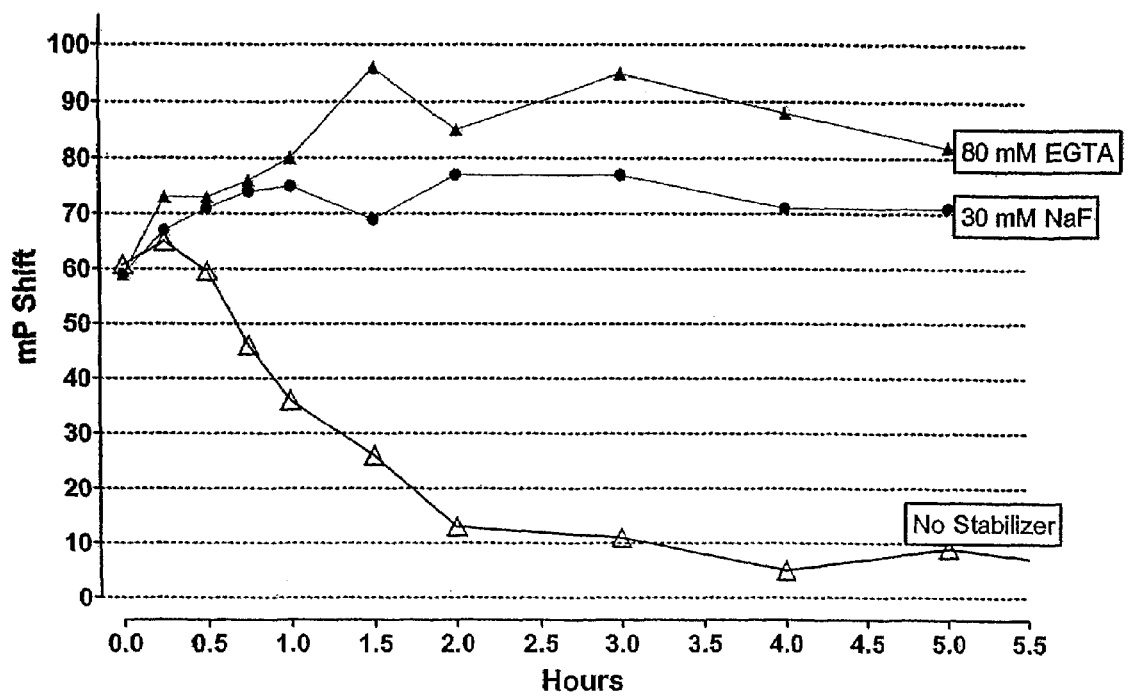
FIG. 11 shows the effect of stabilizing reagents on the FPIA signal in UGT reactions.

UGT enzymes are available only as crude membrane preparations that contain many other enzymes besides the desired UGT. Some of these contaminating enzymes can catalyze hydrolysis of the UDP molecule to UMP or Uridine, resulting in an unstable signal for the assay. To prevent this, agents such as sodium vanadate and EGTA are added to stabilize the assay signal by preventing breakdown of the UDP formed during the UGT reaction. To demonstrate effective signal stabilization and reaction quenching, mock UGT reactions were set up using standard conditions (50 mM $KPO_4$ pH 7.5, 5 mM $MgCl_2$, 0.7% v/v UGT Assay Antibody 1, 1 nM 488-UTP Tracer, 300 ug/mL UGT 2B7 Baculosomes™, 70 μM UDPGA) but lacking an acceptor substrate, so no enzymatic turnover would occur. UDP (5 μM) was added to simulate a situation where the reaction is complete and the plates are sitting waiting to be read.) As shown in FIG. 11, EGTA at 80 mM very effectively inhibits UDP breakdown, but has minimal effects on UGT activity and fluorescence polarization values so it can be included in UGT reactions. Sodium vanadate at 30 mM prevents UDP breakdown and in addition very effectively inhibits UGT activity, so it is added after the UGT reaction is complete to quench the reaction and stabilize the assay signal. The use of such a quenching reagent provides greater flexibility in experimental protocols because HTS assay plates may be read at any time after the quench reagent is added.

Despite their importance, the substrate specificity of the hepatic UDP UGTs that catalyze glucuronidation remain poorly understood because of a lack of flexible in vitro assay methods. The primary problem is that the catalytic assays used require separation of reactants from products, which involves substrate-specific chromatographic steps and thus is not practical in an HTS format. By establishing the concept for measuring the UGT reaction product, UDP in a fluorescent, homogenous format, the applicants have provided the technical foundation for solving this problem. Because the assay measures a product common to all UGT reactions, it allows a single mode of detection with any UGT isoform and any substrate. In addition, the method does not require separation of reactants from products, and is a significant improvement over other related assays because it uses fluorescence detection rather than calorimetric, making it more sensitive and more desirable for pharma HTS platforms, which have become largely reliant on fluorescence based detection. Also, it is a continuous assay method, thus can provide real time kinetic data on UGT enzyme turnover. In addition the antibody-antigen binding reaction is less susceptible to interference from test samples than a conventional coupled enzyme reaction that has been used in the past for donor product detection (Mulder, G. J. and A. B. D. Van Doorn, Biochem J., 1975, 151: p. 131-40). Thus, the novel assay method will enable screening of diverse compounds for metabolism by a panel of isolated UGT isozymes, which will greatly enhance preclinical metabolism studies, and potentially reduce the clinical attrition rate.

Example 2

Assays for Other Types of Glycosyltransferases

Glucuronic acid is one type of carbohydrate molecule that is activated by UDP for enzymatic transfer to other biomolecules; there are many other types of group transfer reactions that use UDP-sugar as an activated donor. These include protein glycosyltransferases that modulate the cellular localization and/or secretion of proteins via their carbohydrate modifications and biosynthetic enzymes that incorporate sugar monomers into polymers such as glycogen and bacterial peptidoglycan. Many of these enzymes are potential targets for therapeutic intervention, both in humans or for antimicrobials.

One class of microbial glycosyltransferases that are of interest from a drug discovery perspective include transferases involved in bacterial cell wall synthesis such as the UDP-galactofurnosyltransferase of *Mycobacterium tuberculosis* (Cren, S., Gurcha, S. S., Blake, A. J., Besra, G. S., Thomas, N. R. Org. Biomol. Chem. 2; 2418-2420. A mammalian glycosyltransferase that is of potential interest from therapeutic perspective is the O-linked protein glycosyltransferase (OGT), which transfers N-GlcNAc to serines and threonines of proteins, regulating their activity in a manner similar to phosphorylation (Zachara, E. N., and Hart, G. W., Biochim. Biophys Acta 1673: 13-28.) These and many other sugar transferases use UDP-activated donor molecules and thus can be detected using an anti-UDP antibody and UTP or UDP tracers described above, or similar antibody and tracer pairs. In addition, there are other classes of glycosyltransferases that use TDP— or CDP-activated donors which may also be detected with similar reagents using the invention herein. An antibody raised against UDP as described herein may have suitable cross reactivity for different purine diphosphates to be used for glycosyltransferases that produce CDP or TDP. Alternatively, different antibodies can be raised against these specific nucleotides.

Example 3

Kinase Assays

Figure 12:
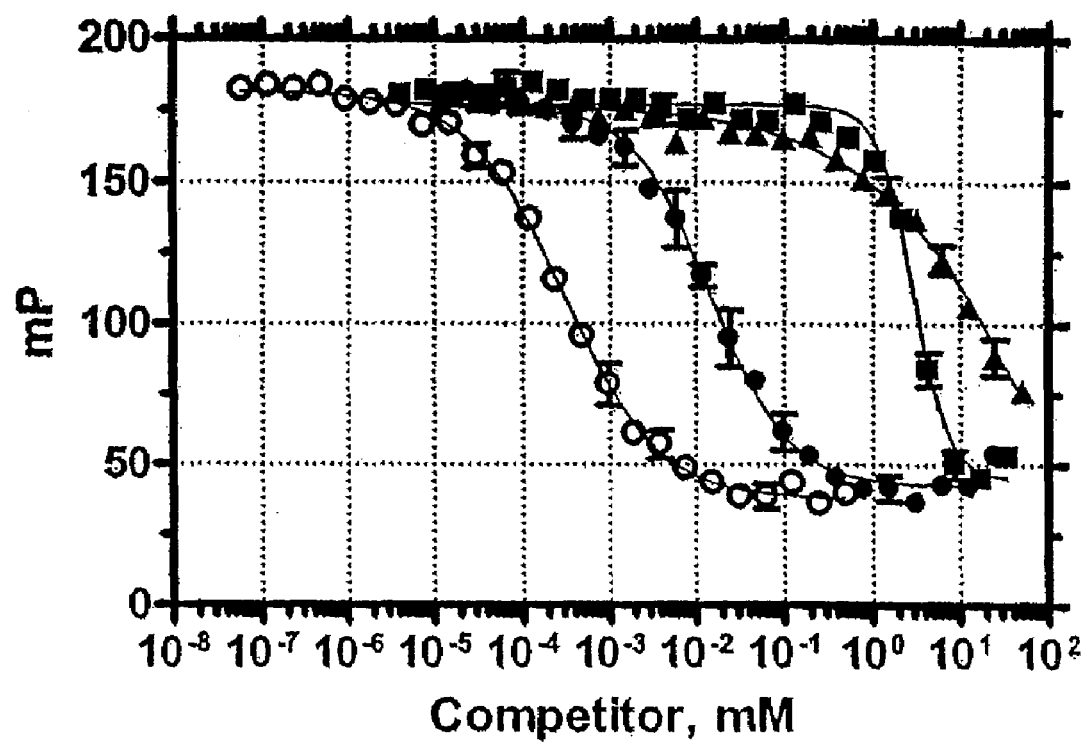
FIG. 12 shows FP competition curves for ADP, ATP and AMP using a polyclonal antibody against ADP and a 5-FAM-N-6-ADP tracer.

To develop an anti-ADP antibody, 6-aminobutyl-ADP (Biolog Life Science Inst., Bremen, Germany) was conjugated to keyhole limpet hemocyanin with a suitable reagent such as glutaraldehyde and used to immunize rabbits. Other carrier proteins such as BSA or ovalbumin and other conjugation chemistries may be used. Attachment to carrier protein via the adenine ring exposes the ribosyl-phosphate moiety, where selectivity is required, and minimizes exposure of the adenine ring. The resulting antisera was tested for ADP binding affinity and selectivity in competitive fluorescence polarization binding assays. Synthesis of the fluor-ADP conjugates used as tracers in these binding assays is described below. Crude serum from naïve rabbits can exhibit high background binding to ADP tracers, so the antiserum was purified using immobilized Protein G (Pierce, Rockford, Ill.) to isolate the IgG fraction. To show that ADP displaced tracer from the purified ADP polyclonal antibody much more effectively than ATP, applicants conducted a series of FP competition experiments using 5-FAM-N6-ADP tracer. The reaction mixtures consisted of 50 mM $KPO_4$, 150 mM NaCl, 0.1 mg/mL BGG, 1 nM tracer, 3% Protein G-purified Anti-ADP antibody, and competitor. The reaction mixtures were incubated for 19 hours at room temperature. Competitors included ADP (○), ATP (●), Adenosine (■), and AMP (▲). These results are shown in FIG. 12. The half maximal point in the competition curve ($IC_{50}$) for ADP is 300 nM, whereas for ATP it is 15 µM; much higher amounts of AMP and adenosine are required to displace the tracer.

These results prove that it is possible to generate antibody with high selectivity for ADP versus ATP, in this case a 50× difference was achieved. They also indicate that the phosphodiester bond in ADP is sufficiently stable in serum to allow an immune response to ADP with very little cross-reactivity to AMP, eliminating the need to use a non-hydrolyzable ADP analog for an immunogen. It should be noted that the use of nonhydrolyzable ADP analogs might enable the development of more selective antibodies.

In addition to the antibody production in rabbits, initial efforts to generate monoclonal antibodies in mice were undertaken, and yielded antibodies with properties similar to the polyclonal serum described above. The monoclonal efforts included the use of immunogens based on conjugation of carrier proteins to both the N6- and C8-positions in the adenine ring. Attachment at the N6 position of adenine yielded approximately 50× selectivity for ADP whereas attachment at the C8 position yielded less.

Tracer Synthesis.

Figure 13:
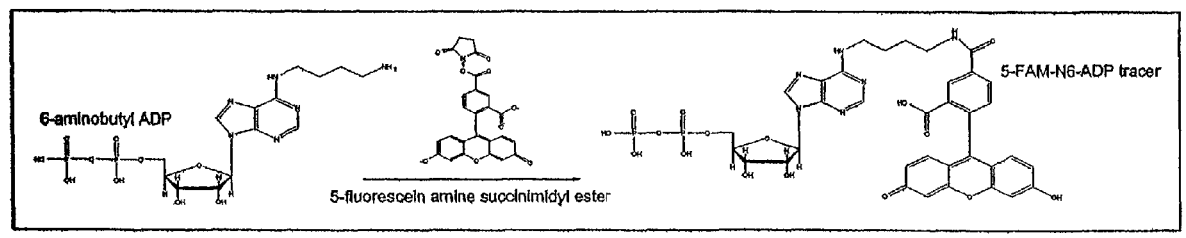
FIG. 13 shows synthesis of a 5-FAM-N-6-ADP tracer.

Tracers were synthesized by conjugating fluors to the N6 and C8 positions in the adenine ring using different linkers. Amine reactive fluors were conjugated to N6-aminobutyl ADP as shown for example in FIG. 13. To synthesize fluorescein-ADP conjugate used as tracer for competitive binding experiments, applicants added to 50 µL of N6-aminobutyl-ADP (Sigma) (54.3 mg/mL), 12 µL of 5-Fluorescein amine-N-succinimidyl ester (Molecular Probes) (20 mg/mL) followed by 138 µL of dimethyl sulfoxide. The reaction mixture was shaken for 72 hours and products were purified via preparative thin layer chromatography (Whatman LK-6F) using 70:30 Ethanol/2 ml ammonium acetate. Fluorescent bands were scraped off and desorbed using 1:1 Methanol/2 mM ammonium acetate, pH 5.5.

Attachment to the C8 of adenine required bromination of ADP, which occurs predominantly at C8, and subsequent nucleophilic displacement using diamino-alkanes, was followed by reaction with amine-reactive fluors. Initially, applicants limited fluors to fluorescein derivatives because there were numerous reactive derivatives available and because fluorescein was relatively hydrophilic, so generally yields tracers with low surface binding properties. Synthetic reactions with several combinations of ADP-linker molecules and amine reactive fluoresceins were run and the fluorescent products resolved by thin layer chromatography (TLC). HPLC can also be used for additional purification of tracer molecules if necessary.

Figure 14:
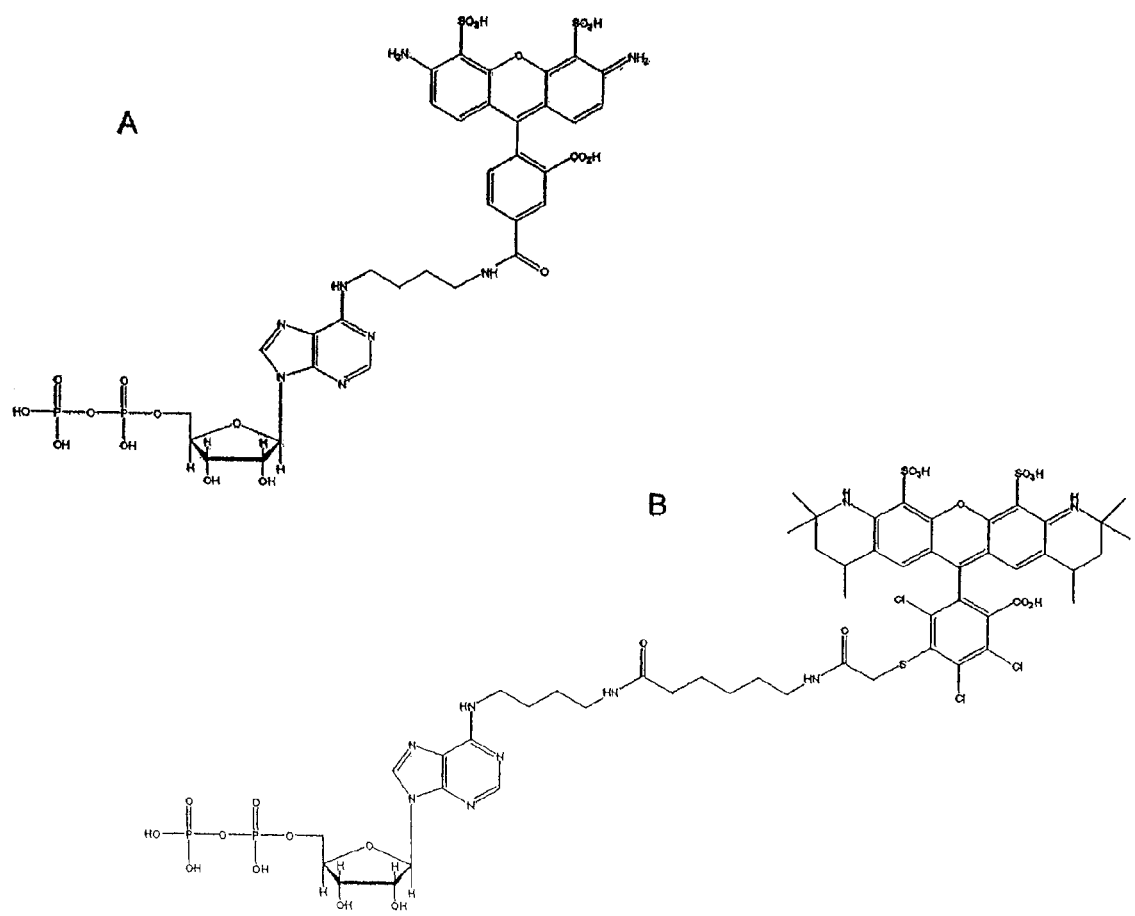
FIG. 14 shows examples of tracers used to quantify ADP formation.

The 5- and 6-fluorescein amine (FAM) conjugates to N6-aminobutyl ADP used for kinase assays exhibit highest affinity binding for the anti-ADP antibody used in initial studies. These FAM tracers were used in the competitive binding experiments as shown in FIG. 12. None of the tracers made from conjugates to the adenine C8 showed high affinity binding to antibody. Tracers based on Alexa Fluors® (Molecular Probes, Corvallis, OR) were synthesized using similar methods and showed antibody binding and fluorescence polarization properties similar or better than the fluorescein based tracers. Tracers based on Alexa Fluors® include for example, Alexa Fluor® 488/6-aminobutyl ADP and Alexa Fluor® 633/6-aminobutyl ADP as shown in FIGS. 14 A and B, respectively.

Figure 15:
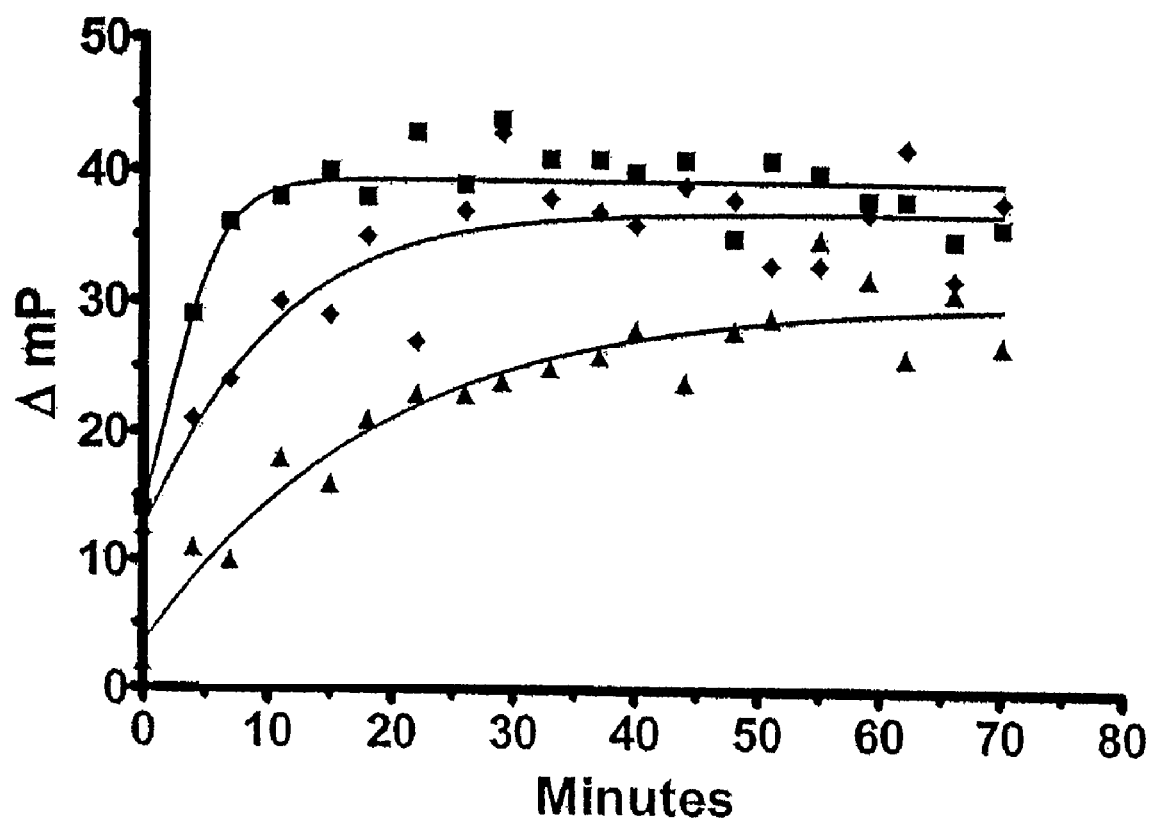
FIG. 15 shows the dependence of the FPIA-based kinase enzymatic assay on enzyme concentration and time.

The N6-aminobutyl ADP-5-FAM tracer and rabbit antiserum was used to detect Protein Kinase A (PKA) activity. In 384-well, black CliniThermo plates, various amounts of PKA were preincubated at 30° C. with kemptide substrate (Sigma, St, Louis, MO) in the presence of tracer/antibody complex. ATP was then added to start the reaction. The final assay conditions were 50 mM HEPES buffer (pH 7.5), 1 mM EGTA, 0.1 mg/ml BGG, 50 uM kemptide substrate, 10 uM ATP, and 10 mM $MgCl_2$, 1 nM fluorescein-labeled tracer (N6-AB-ADP 5FAM), and rabbit anti-ADP proteinG-purified polyclonal antibody in a total volume of 30 uL. The following amounts of PKA were used: ■, 3.0 ng, ♦, 0.3 ng, ▲, 0.2 ng. Reactions lacking PKA were used as controls. FIG. 15 shows the assay results for PKA using FPIA. As shown in FIG. 15, the slope of the assay response curve over time increased with increasing amounts of PKA as would be expected for an enzymatic reaction. Note that the detection reagents could also be added after the reaction has been quenched with an agent such as EDTA, as the FP signal is stable for several hours and such stop-time assays are often employed in automated HTS laboratories. In addition, an ADP standard curve may be generated to allow quantitative determination of enzyme turnover rates. The Alexa Fluor® tracers were used in similar experiments with both polyclonal and monoclonal antibodies for detection of PKA activity. In this example the acceptor substrate used was a small peptide, but a peptide or an intact protein could also be used which is not possible with many of the other currently available kinase assay methods.

Furthermore, it is noted that in screening for inhibitors, the compounds to be tested are generally dispensed into wells prior to addition of any other assay components. Control wells with no inhibitor added are also included for comparison. In screening for inhibitors that bind at the ATP site, it is often desirable to use a concentration of ATP that is close to the $K_m$ concentration for a particular kinase enzyme. Most kinases exhibit ATP $K_m$ values ranging from 0.5 to 200 µM. By increasing or decreasing the amount of antibody used for ADP detection and keeping the tracer constant, it is possible to shift the equilibrium binding curve to the left or right, and thus change the sensitivity of the FPIA, which enables its use over a broad range of starting ATP concentrations encompassing the full range of kinase ATP $K_m$ values.

Example 4

ATPase and GTPase Assays

The group transfer reaction assays described above, such as kinase assays are equally applicable to ATPases and GTPase. Specifically, protein kinase reactions require the addition of two substrates to the reaction: (1) ATP and (2) a peptide or protein. During the protein kinase reaction, the phosphate group on the ATP molecule is transferred from ATP to the protein or peptide substrate (ADP is generated during the transfer of this transfer reaction). FPIA detects the ADP that is produced. Alternatively, ATPases do not require the addition of a second substrate for the reaction to proceed. ATPases only require the addition of one substrate (1) ATP. During the ATPase reaction, a phosphate group on the ATP molecule is transferred from ATP to a water molecule (and ADP is generated). Similar to the kinase reaction, FPIA detects the ADP that is produced. This ATPase reaction is still a group transfer reaction because the water molecule is the acceptor of the phosphate group. Therefore, the phosphate group that is transferred from ATP is transferred to a water molecule.

To establish the universal applicability of the kinase assay described herein, now commercially known as Transcreener™ KINASE Assay (BellBrook Labs, LLC; Madison, Wis.), to other types of group transfer reactions, applicants conducted an ATPase titration assay. In general, the reagents required for an ATPase assay are the same as those described for the kinase assay: (1) an antibody that recognizes ADP with high selectivity over ATP and (2) a fluorescent ADP tracer molecule. Also, these reagents are used in a fashion similar to that described for the kinase assay.

More specifically, the ATPase assay conducted by applicants used purified recombinant ATPase protein, Hsp90; human heat shock protein 90 and Hsc70; recombinant bovine heat shock cognate protein-ATPase fragment; both of which can be expressed in *E. coli* and purified using affinity chromatography (Rowlands, M. G. et al., Anal Biochem, 2004, 327:176-83). Hsp90 and Hsc70 were each serially diluted two-fold in buffer (50 mM HEPES, pH 7.5, 20 mM KCl, 2 mM EGTA, 0.01% Brij-35). The ATPase reaction was initiated with 50 µM ATP and 2 mM $MgCl_2$ (final concentrations in 10 µL ATPase reaction) and placed at 37° C. for 3 hours. The ATPase reactions were stopped with EDTA. The ADP generated during the ATPase reaction was detected by adding an equal volume (10 µL) of 80 g/mL Transcreener™ ADP Antibody/Transcreener™ 4 nM ADP Far Red Tracer in 1× Transcreener™ Stop and Detect Buffer (50 mM HEPES, pH 7.5 containing 400 mM NaCl, 20 mM EDTA, and 0.02% Brij-35). The control reactions lacked the specific ATPases, Hsp90 and Hsc70.

Figure 26:
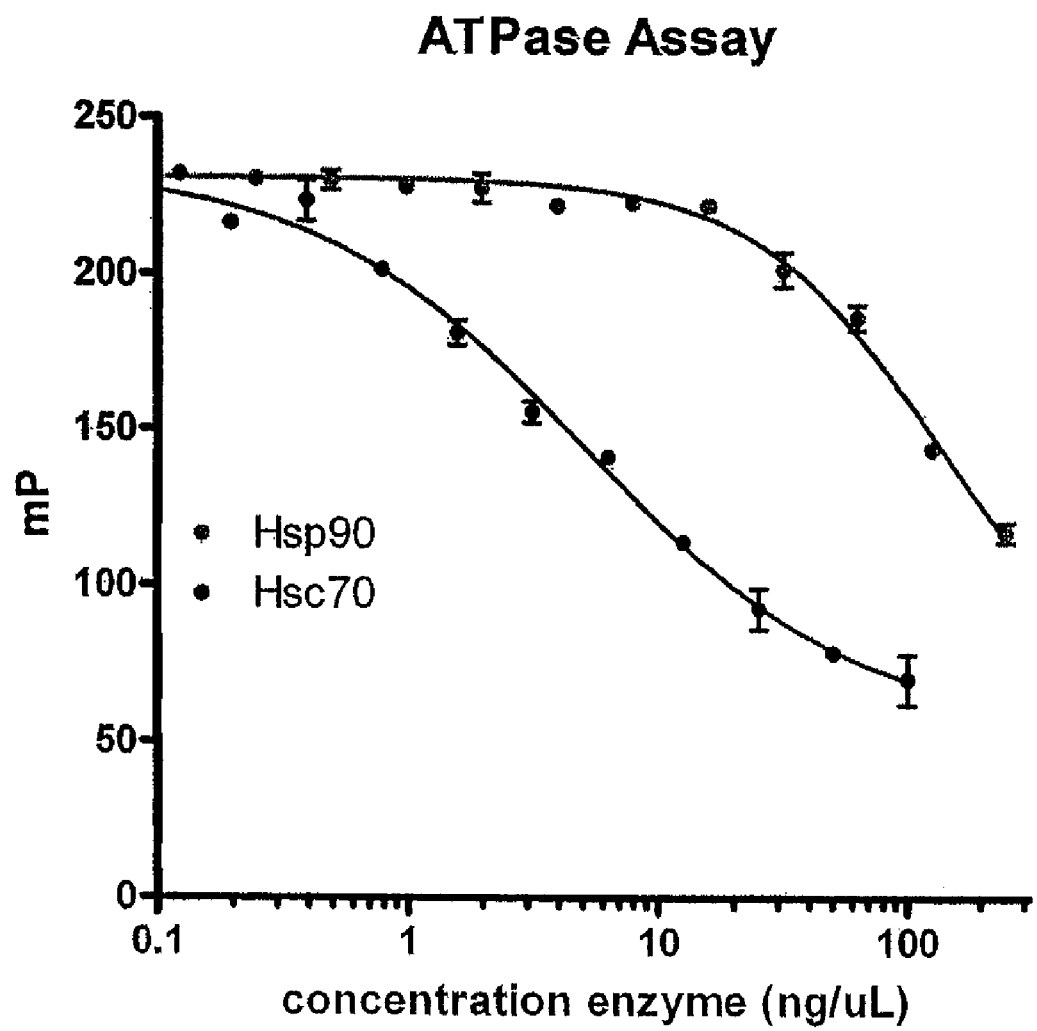
FIG. 26 shows the dependence of enzyme (ATPase) concentration on the production of ADP detected using the FPIA based assay described herein.

The fluorescence polarization values generated by the tracer were read using a multiwell reader such as the Tecan Ultra. The decrease in polarization in the wells containing enzyme relative to the control wells is used to determine the amount of ADP produced. It is noted that in HTS applications, the reactions are typically performed in 96-, 384-, or 1536-well plates made of opaque plastic. The results of the ATPase assay are depicted in FIG. 26, which shows the dependence of enzyme (ATPase) concentration on the production of ADP detected using the FPIA based assay described herein.

It is also envisioned that other types of ATPases, such as members of the mitotic kinesin family could be assayed in a similar manner, except for differences in buffer and additive requirements specific for the particular enzyme, known to those of skill in the art; e.g., the addition of microtubules (DeBonis, S. et al., Mol Cancer Ther, 2004, 3:1079-90). Using an antibody and tracer that have rapid dissociation kinetics, it is also possible to add the detection reagents during the course of the enzymatic reaction for continuous monitoring of ADP production.

Further, the assay described herein for is equally applicable to another enzyme catalyzing a group transfer reaction, GTPase. The detection reagents required to measure GTPase activity by FPIA are similar to those required for ATPase activity: (1) an antibody that recognizes GDP selectively over GTP and (2) a fluorescent GDP nucleotide tracer. The monoclonal antibodies produced for ADP have exhibited significant cross reactivity with GDP. As such, it is envisioned that the same antibody may be used for the specific detection of ADP or GDP. Further, the antibody is highly selective for the donor product, ADP or GDP, regardless of the enzyme used to catalyze the group transfer reaction.

Researchers in the field have historically used GTPase measurements of the intrinsic GTPase activity of the Gα subunit as one method of screening for pharmacological modulators of GPCR signal transduction (Kimple, R. J. et al., Comb Chem High Throughput Screen, 2003, 6:399-407), and for small G proteins such as Ras. To detect GTP hydrolysis by a Gα protein such as $G_{ai1}$, the recombinant, purified protein was preincubated with GTP in a suitable buffer, such as 50 mM HEPES, pH 7.4, 1 mM DTT, and 100 mM GTP at room temperature for one hour. The excess GTP was subsequently removed by passage over a gel filtration column or dialysis.

Recombinant "regulator of G protein" protein (RGS) was then added to the GTP-loaded $G_{ai1}$, initiating GTP hydrolysis. With the methods described herein, the GDP detection reagents, antibody and tracer, can be added to a screening assay, for example, while the reaction is occurring or after it is complete or has been quenched. The production of GDP can then be measured by the decrease in fluorescence polarization relative to reactions lacking GTPase. The GTPase activity can be enhanced by adding RGS.

Alternatively membrane fractions containing an expressed GPCR proteins can be reconstituted with heterotrimeric G proteins and RGS to generate an intact signal transduction system in vitro. Binding of agonist then initiates the cycle of GTP binding and hydrolysis that is detected using the FPIA for GDP. In this way, the FPIA for GDP could be used to screen directly for agonists or for antagonists of GPCRs.

As noted above, the reagents described herein can be used for detecting both ADP and GDP, regardless of the enzyme or where that detection takes place, namely in a solution, in vitro, in situ or in vivo. It is envisioned that the antibodies described herein are suitable for selectively detecting nucleotide di-phosphates as donor products without being limited to donor substrate molecules used in the enzyme reaction. Suitable nucleotide di-phosphates (donor products) include GDP, ADP, UDP, or CDP. Also, suitable donor molecules may include, but are not limited to GTP, ATP, GDP-sugars (GDP-mannose, GDP-fucose, and GDP-glucose), or ADP-sugars (ADP-glucose, ADP-ribose, and ADP-mannose) among others. The antibodies against the donor products allow for the detection of ADP/GDP group transferases (i.e., kinases), ATP/GTPase, ADP/GDP glycosyltransferases, as well as other known group transfer reactions.

Applicants have found that antibodies produced against ADP have about 5-fold higher affinity and similar selectivity for both ADP and GDP. Antibodies against GDP are also generated with the same immunogen as the ADP antibody, which is described here and in related patents by the applicants, such as U.S. Pat. Nos. 7,355,010 and 7,332,278 incorporated by reference in their entirety herein. Antibodies against GDP can utilize the same ADP (N6-antibody-ADP) tracer or a similar GDP tracer. Since the molecules and conjugation methods are similar, it is expected that ADP/GDP antibodies could also be produced with GDP immunogens.

It is contemplated that an antibody selectivity for the donor product (i.e., ADP or GDP) of about 10 times higher than the donor substrate is suitable for effective donor product detection. Of course, having a antibody with selectivity of higher than 10 fold is preferable, such as 20, 40, 50, 100, 120, 130, 150, 200, 300, 500, 1000 and higher. In regards to determining antibody selectivity, those skilled in the art recognize that this is dependent on the purity of the donor substrate (i.e., GTP). Any contaminating compounds, such as GDP that compete with the bound nucleotide tracer can reduce the apparent selectivity factor.

Described below are specific examples of assays where anti-ADP and anti-GDP antibodies were used to detect donor products of group transfer reactions.

Materials and Methods for ATPase and GTPase Assays

All assays were performed in black Corning® 384 Well Flat Bottom Microplates (Part #3654)(Corning, N.Y.) or black Corning® 384 Well Round Bottom Low Volume Polystyrene Non-Binding Surface Microplates (Part # 3676). Mixing after additions was performed by orbital shaking. Unless otherwise noted, reactions were equilibrated for one hour at room temperature before reading the plate on the instrument.

Fluorescence intensity and polarization measurements utilizing the ADP-Alexa Fluor® or GDP-Alexa Fluor® tracers were performed on a Tecan Ultra or Safire²™ plate reader (Durham, N.C.) using appropriate filter sets. For the ADP-Alexa Fluor®633 tracer, the filters for the Safire2 were 635 nm excitiation (LED) and 670 emission (20 nm bandwidth). The free tracer reference was set to 20 mP, and the buffer (with or without antibody) was used as the buffer blank for both the sample and free tracer reference wells. Data from binding and competition curves were fit to a variable slope sigmoidal dose-response curve and the $IC_{50}$ were calculated using GraphPad Prism (GraphPad Software, San Diego, Calif.).

Development and Optimization of Antibody Reagent for GDP Detection

A collection of adenosyl 5'-diphosphate (ADP) and guanosyl 5'-diphosphate (GDP) derivatives were synthesized at BellBrook Labs or Biolog (Germany) and were conjugated to Keyhole Limpet Hemocyanin (KLH) or bovine serum albumin (BSA) at different positions on the ADP or GDP molecule (BioSyn Lewisville, Tex.). These conjugates were used as immunogens or ELISA screening antigens for mouse monoclonal antibody production at Harlan Biosciences (Madison, Wis.). ADP/GDP antibodies from several clones were purified using immobilized Protein G at Covance (Denver, Pa.). ADP/GDP fluorescent tracers were synthesized from similar ADP/GDP intermediates and amine-reactive Alexa Fluor® dyes with emission peaks ranging from 535-633 nm (Molecular Probes, Eugene, Oreg.).

To identify suitable antibody/tracer pairs for FP assay development, equilibrium binding assays were performed by titrating ADP/GDP antibodies with a panel of ADP/GDP tracers (1-2 nM). The first well consisted of 1 mg/mL antibody in 30 µL of the final equilibrium buffer (i.e. 50 mM HEPES (pH 7.5), 0.01% Brij-35, 1 mM EGTA, 2 mM MgCl2, 0.5% DMSO, 20 mM EDTA, and 2 nM tracer). A two-fold serial dilution of the antibody was then performed in 15 µL of the same buffer. Antibody-tracer pairs that bound with reasonable affinity (<1 µM) and demonstrated >100 mP shift were then tested for GDP selectivity. Competition binding assays were performed in a like manner by titrating ADP, ATP, GDP, GTP, and other adenine derivatives in the same final equilibrium buffer containing the tracer and antibody (EC85 concentration). The time required to equilibrate the antibody/tracer complex and the antibody/tracer/nucleotide combinations was predetermined.

Figure 27:
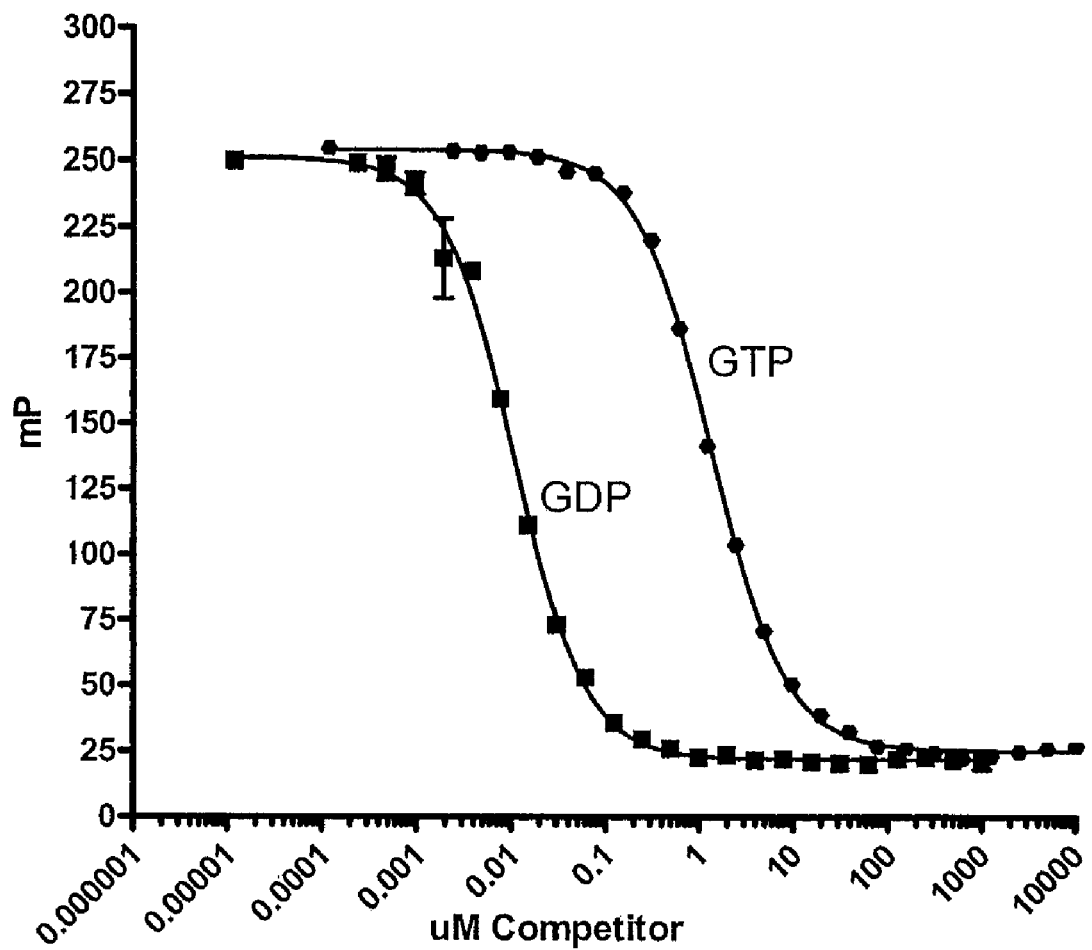
FIG. 27 shows GDP monoclonal antibody binding selectivity for GDP vs. GTP described herein.

In one example, the monoclonal antibody binding selectivity between GDP vs. GTP was analyzed and the results are set forth in FIG. 27. The antibody-tracer complex was incubated with increasing concentrations of GDP or GTP in 25 mM HEPES (pH 7.5), 2 mM $MgCl_2$, 1 mM EGTA, 0.5% DMSO, 0.01% Brij-35, 20 mM EDTA, 2 nM far red Tracer, and 0.85 µg/mL antibody for one hour. The $IC_{50}$ values for GDP and GTP are 0.01 µM and 1.3 µM, respectively, resulting in about 130-fold selectivity for GDP. Applicants results indicate that a selectivity of 10 fold or higher is suitable for the purposes described here. Further, in regards to determining antibody selectivity, those skilled in the art recognize that this is dependent on the purity of the donor substrate (i.e., GTP).

It is envisioned that the antibody binding selectively to GDP may be used in any immunoassay wherein the product is detectable by an antibody. Suitable immunoassays include but not limited to homogeneous fluorescence immunoassay, a homogeneous fluorescence intensity immunoassay, a homogeneous fluorescence lifetime immunoassay, a homogeneous fluorescence polarization immunoassay (FPIA), a homogeneous fluorescence resonance energy transfer (FRET) immunoassay or a homogenous chemiluminescent immunoassay, or a non-homogenous assay such as enzyme-linked immunoassay (ELISA).

Figure 28:
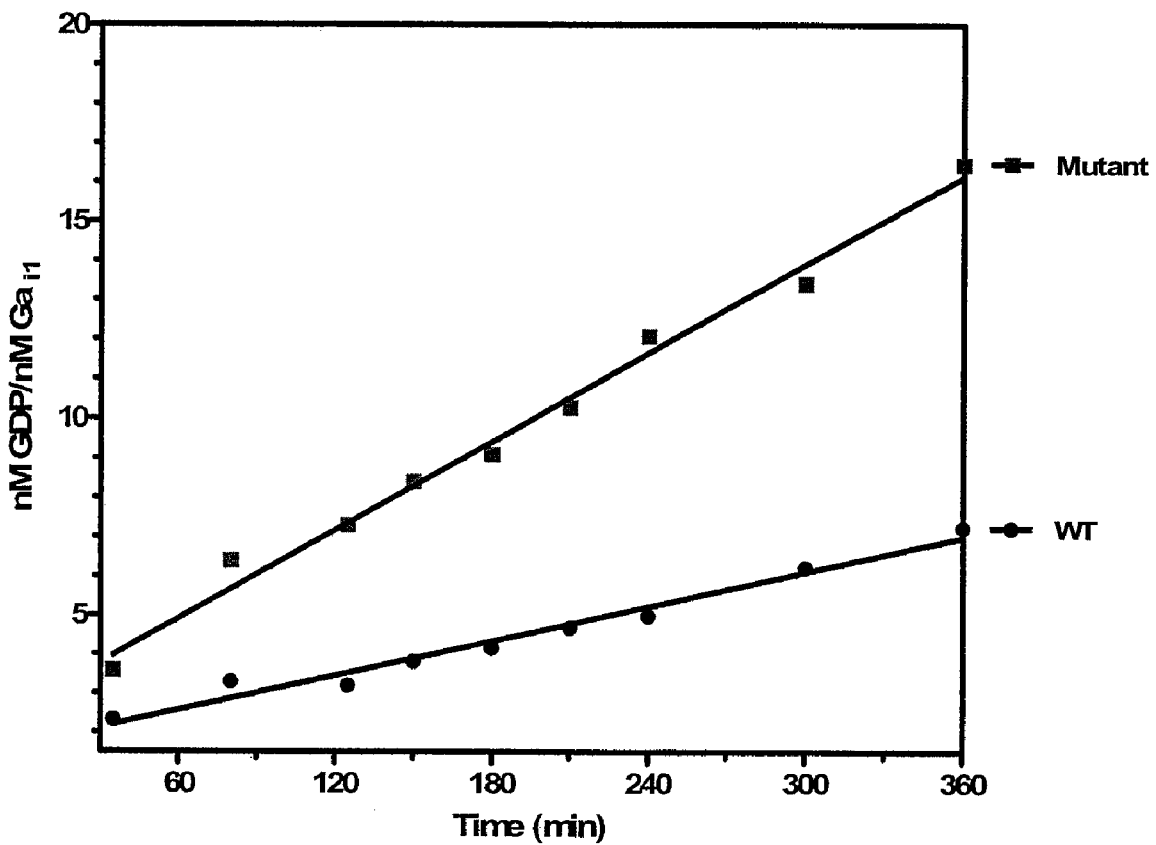
FIG. 28 shows the GDP production by wild type and mutant Gai1 protein (GTPase) using the Transcreener GDP Assay.

In one example, using the Transcreener® GDP Assay, GDP was produced by wild type and mutant Gai1 protein (GTPase activity). To perform the GDP assay, 100 mM Gai1 wild type or 100 nM Gai1 A326S Dissociation mutant was added to 20 uL reaction mix (20 mM Tris 7.5 pH, 1 mM EDTA, 10 mM $MgCl_2$, 10 µM GTP, 40 µg/mL GDP antibody, 2 nM GDP Tracer) in a 384 well plate and incubated at 30° C. The results are set forth in FIG. 28. Fluorescence polarization was measured over time on a Tecan Ultra-Ex/Em 612/670. Data in millipolarization units (mP) was converted to GDP produced using a GTP/GDP standard curve.

Example 5

Sulfotransferase Assays

Expression and Purification of SULT1E1

In order to establish a sulfotransferase HTS assay method, SULT1E1, a SULT isoform, was first subcloned into an E. coli expression vector with a C-terminal 6× histidine tag and the expressed protein was purified by affinity chromatography and characterized with respect to its physical and enzymatic properties.

The $V_{max}$ and estradiol $K_m$ values determined for the purified SULT1E compared favorably with published values for purified recombinant SULT1E1, which are 30-40 nmol/min/mg and 5-15 nM, respectively. The published data on acceptor substrate specificity is more varied, but the results reflect the general trend that estradiol and estrone are very good substrates, α-naphthol is intermediate, and DHEA and dopamine are very poor substrates. Thus, all of the SULT1E1 constructs applicants expressed showed native substrate specificity and catalytic rates similar to the highest published values.

Synthesis of Antigens and Generation of Antibodies

Development of the proposed FPIA-based SULT assay method requires an antibody that specifically binds the product of the SULT reaction, PAP, in the presence of excess PAPS; i.e., an antibody that discriminates on the basis of a single 5'-sulfate group. There is ample precedent for antibodies that discriminate between various nucleotides that differ only in the number of phosphates, which is similar in size and structure to a sulfate group as described above. However, there was no precedent for generation of antibodies that specifically recognize PAP.

Small molecules like PAP must be conjugated to a carrier protein in order to be used as an immunogen. Suitably, an antigen density of 10-20 per carrier protein is optimal. As discussed above, the two elements of our antigen synthesis strategy were a) synthesis and testing of several antigens because the site of attachment to nucleotide and linker structure can profoundly affect the properties of the resulting antibodies (Signorini, N. et al., Chem Res Toxicol, 1998, 11:1169-75; Crabbe, P. et al., J Agric Food Chem, 2000, 48:3633-8; Ishiguro, H. et al., Oncogene, 2002, 21:6387-94), and b) conjugation via the adenine ring because this may allow free exposure of the 5-phosphate group and limit immunoreactivity with the adenine portion of the molecule, resulting in antigens with the desired specificity. None of the nitrogens in the adenine ring were reactive enough to conjugate directly to protein or via crosslinking reagents, so reactive PAP derivatives were used as a starting point; the only commercially available reagent was N6-aminohexyl PAP. What initially appeared to be the most straightforward approach— reacting N6-aminohexyl-PAP with carrier proteins by carbodiimide coupling or amine-reactive crosslinkers-generated unacceptably low antigen density, despite a significant experimental effort.

Figure 16:
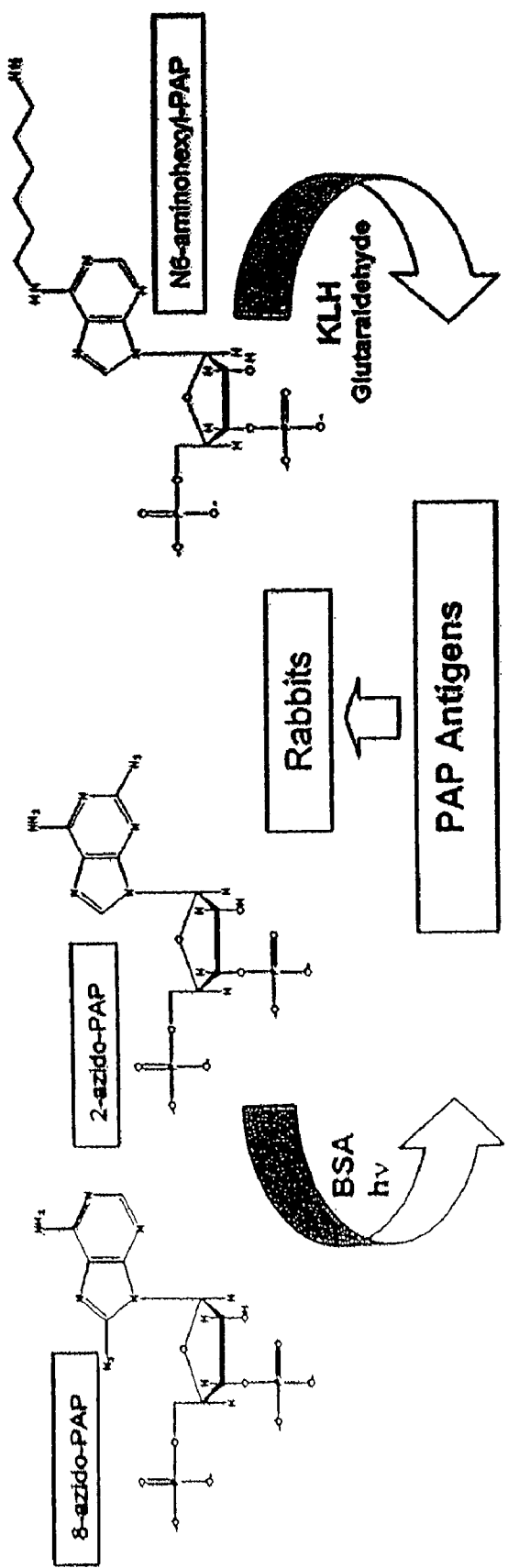
FIG. 16 shows the synthesis of PAP antigens.

To pursue alternative chemistries applicants synthesized the following photoreactive molecules: 2- and 8-azido-PAP and C8-hexylamino-PAP (FIG. 16). FIG. 16 shows the synthesis of PAP antigens. 2- and 8-azido-PAP, which were custom synthesized by ALT, Inc. (Lexington, Ky.) were irradiated (254 nm) in the presence of BSA; unreacted nucleotides were removed by filtration and dialysis. Final antigen densities of 7-12 PAP/BSA were obtained as determined by absorbance of the adenine ring (shifted to 270-280 nm). Rabbits (3 per antigen) were immunized by Lampire Biologicals (Ottsville, Pa.). N6-aminohexyl PAP (Sigma) was conjugated to KLH using glutaraldehyde and injected into three rabbits by Biosynthesis Corp. (Lewisville, Tex.). Immunization schedules were similar for all antigens and included 3-4 injections over a 4-6 week period.

Antigens from the two photoreactive PAP derivatives were produced and sent out for antibody production. The generation of antigen from N6-aminohexyl PAP using glutaraldehyde crosslinking to KLH and production of antibody was contracted out to a separate company (FIG. 16). All three antibodies were reported by the contract producers to bind PAP as determined by ELISA (data not shown).

In addition, applicants synthesized the reactive derivatives N6-carboxymethyl PAP and 2'-O-succinyl-PAP (FIG. 17); antibodies from these derivatives have not yet been produced. A detailed description of Ab binding properties using competitive FPIA is provided below following the description of tracer synthesis.

Synthesis of PAP-Fluor Tracers

An FPIA tracer molecule can be divided into three different structural components: the antigen, the fluor, and the linker used to join them; an additional key structural variable is the site of attachment of the linker to the antigen. Because identification of a tracer is largely empirical, applicants used a variety of linkers to join PAP and fluorescein via different sites on each molecule; in most cases the final linker region is a composite of the reactive fluorescein and PAP molecules used.

The antibody strategy was to conjugate through the adenine moiety in order to generate antibodies that bind specifically to the ribosyl-phosphate group of PAP. The same sites are the obvious sites for fluor conjugation as well in order to leave the desired immunoreactive portion of the tracer molecule free to bind Ab. Also, fluorescein was the preferred fluor used for conjugation. Though red-shifted fluors such as rhodamine are more desirable for HTS applications, development of FP tracers with fluorescein is usually more straightforward because it is less prone to non-specific binding effects and there are numerous activated derivatives available. As to the linker molecule, it affects tracer characteristics in a number of important ways that impact both its antigenic and fluorescence properties. There is generally a balance that must be struck between separating the antigen from the fluor enough to allow unhindered interaction with antibody without creating too much freedom of motion for the fluor. The former can result in lowered affinity Ab binding and in quenching of the fluor, whereas the latter reduces the polarization shift upon Ab binding, thereby reducing the dynamic range of the assay.

N6-aminohexyl PAP was the only activated PAP molecule used for immunogen synthesis that was useful for tracer synthesis; the photoactivation reactions required to conjugate the two azido-PAP derivatives may be inefficient for joining two small molecules. To provide PAP molecules activated at different positions and with different linker regions, applicants outsourced the production of C8-aminohexyl-PAP and synthesized in house two PAP derivatives with carboxy-terminal linkers: N6-carboxymethyl-PAP and 2'-O-succinyl-PAP. Though the latter compound is linked through the ribose hydroxyl rather than the adenine, this approach has been used to generate highly specific antibodies and tracers for cAMP (Horton, J. K., Martin, R. C. et al., J Immunol Methods, 1992, 155:31-40).

Below are brief descriptions of the synthesis and purification of activated PAP molecules and their conjugation to various activated fluors; tracer synthesis components are summarized in FIGS. 17 and 18. In general, PAP molecules with amino-terminal linkers were conjugated to fluors activated with succinimidyl esters (or isocyanate in one case) and PAP molecules with carboxy-terminal linkers were reacted with fluorescein derivates containing free amino groups using carbodiimide coupling.

Figure 17:
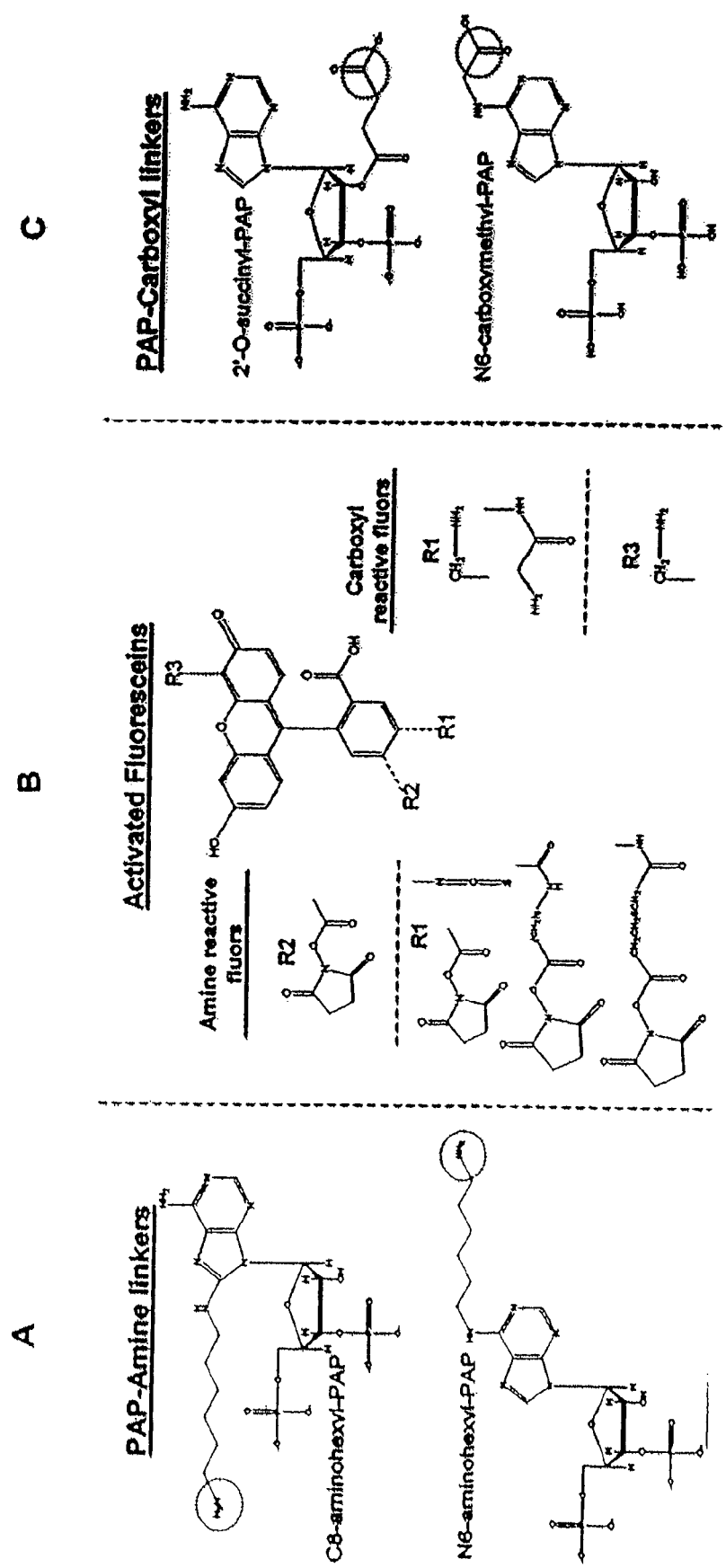
FIGS. 17 A-C show components of PAP tracer synthesis.
Figure 18:
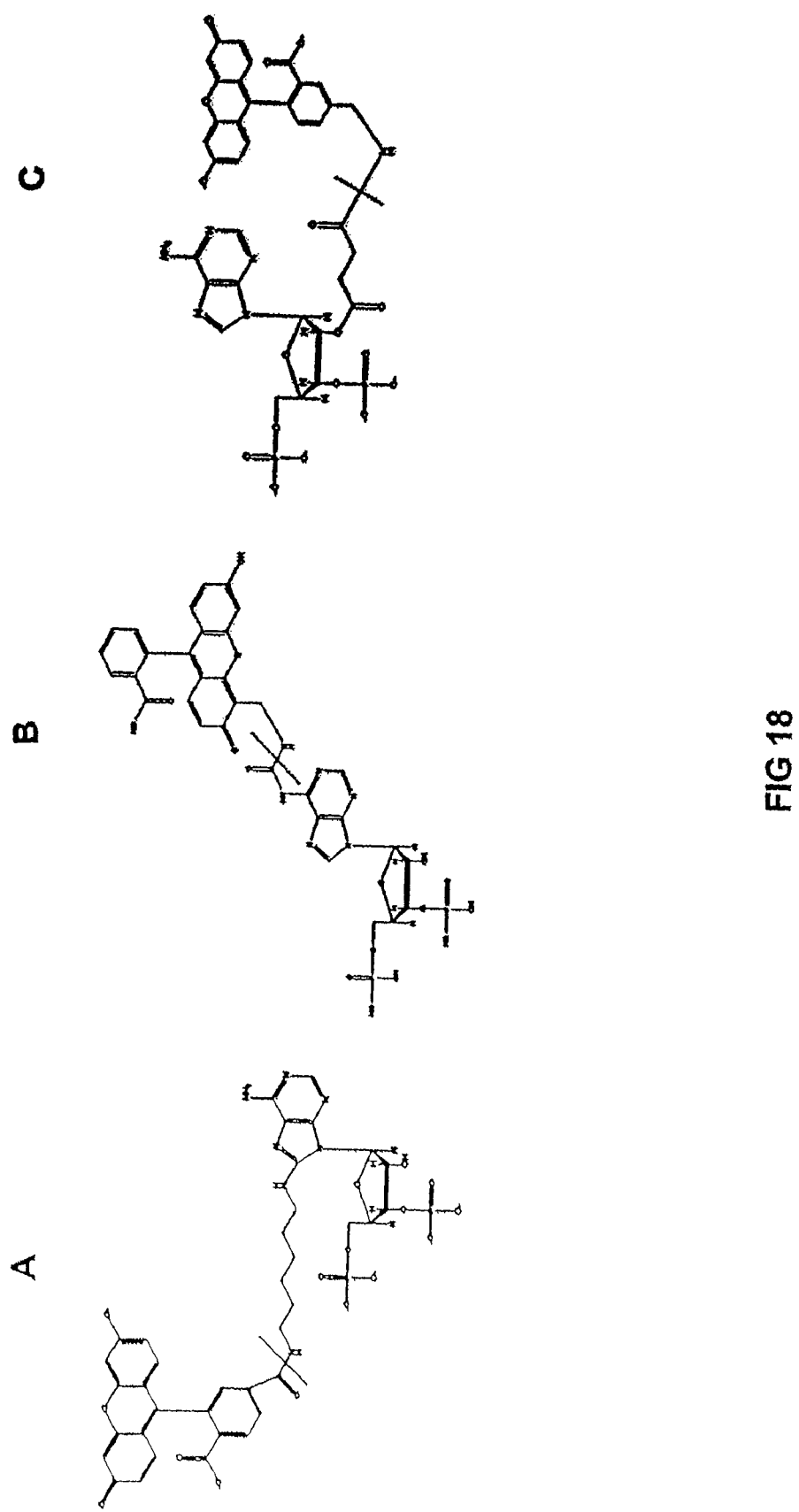
FIGS. 18 A-C show representative final PAP tracer structures.

FIG. 17 illustrates structures of components of Tracer Synthesis. FIG. 17 from left to right provides PAP molecules with amino-terminal linkers attached at the C8 and N6 position, amine- and carboxy-reactive fluorescein derivatives, and PAP molecules with carboxy-terminal linkers at the N6 and 2'-OH. The fluorescent PAP conjugates were separated by TLC and tested for binding to anti-PAP antibodies. In accordance to the invention, sixteen reactions were run containing different combinations of PAP and fluorescein derivatives and each reaction yielded 1-4 fluorescent products that could be resolved by TLC. In all, more than 40 tracers have been purified and tested for binding to Ab. N6-aminohexyl PAP (Sigma) and all of the reactive fluorescein derivatives (Molecular Probes) are commercially available. 2'-O-succinyl-PAP and N6-carboxymethyl-PAP were synthesized as described below; C8-aminohexyl PAP was synthesized by Jena Biosciences (Jena, Germany). FIG. 18 provides representative final tracer structures.

Preparation of N6-Carboxymethyl PAP

To prepare N6-carboxymethyl PAP, 100 mg PAP was incubated with 0.3 g Iodoacetic acid in 1.2 mL aqueous, adjusted to pH 6.5 with LiOH. The reaction proceeded at 30° C. for 5-7 days, periodically adjusting the pH to 6.5. The resulting 1-carboxymethyl-PAP product was precipitated with ethanol and reconstituted in distilled water and the pH was adjusted to 8.5 with LiOH. This reaction was heated at 90° C. for 1.5 hours to yield the N6-carboxymethyl PAP. This product was purified on a Dowex1-X2 (200-400 mesh) column equilibrated in 0.3 M LiCl, pH 2.75. A gradient was applied over 10 column volumes using 0.5M LiCl, pH 2.0. N6-carboxymethyl PAP eluted off the column as pure product and was confirmed by mass spectral analysis, ~20% yield.

Preparation of 2'-O-Succinyl-PAP

To prepare 2'-O-Succinyl-PAP, 10 mg (0.024 mmole) PAP and succinic anhydride (43 mg, 0.426 mmole) were dissolved in distilled $H_2O$ containing 10% triethylamine (v/v, 1 mL) and shaken for 1.5 hours with reaction progress monitored using reverse phase thin layer chromatography (RP-TLC). Upon completion, the reaction was lyophilized twice to ensure no residual triethylamine remained. The expected succinate was column purified using Fast Flow Sepharose-Q resin (Pharmacia) equilibrated with 50 mL 250 mM $NH_4OAc$, and eluted with a linear gradient of 500 mM to 750 mM $NH_4OAc$ (50 mL of each). Fractions containing the product were concentrated on a rotovap followed by lyophilization to furnish 8.4 mg or 67% yield as determined by absorbance measurement. Stock solution was stored at –20° C. for future use.

Preparation of Fluorescein Conjugates with Amino-Activated Pap

To prepare fluorescein conjugates with amino-activated PAP, 10 μL of a 100 mM solution of N6- or C8-aminohexyl-PAP in distilled $H_2O$ was combined in a screw cap vial with a molar equivalent of a fluorescein succinimidyl ester, the reaction was brought to a final volume of 200 μL using anhydrous dimethyl sulfoxide (DMSO), and shaken on a vortexer for 24 hours. Reaction progress was followed by RP-TLC using $H_2O$ as the developing media. Reaction products were purified using preparative TLC on normal phase silica gel using 1:1 EtOH/0.5 M NH4OAc. Fluorescein labeled compounds—generally 3-5 produced in each reaction—were visualized using UV light, scraped from the TLC plates, and extracted from the silica gel using 1:1 MeOH/0.5 M NH4OAc. Individual fractions were shaken on a vortex for 1 hour wrapped in aluminum foil and centrifuged at 4000 RPM for 8 minutes. The supernatants were transferred to a separate labeled vial and the extraction process repeated. Combined supernatants were standardized to 50 nM solution for future use and frozen in amber microfuge tubes at –20° C.

Preparation of Fluorescein Conjugates with Carboxy-Activated Pap

To prepare fluorescein conjugates with carboxy-activated PAP, 10 ml of a 100 mM solution of N6-carboxymethyl-PAP or 2'-O-succinyl-PAP in distilled $H_2O$ was combined with 50 equivalents of 1-ethyl-3-(dimethylaminopropyl) carbodiimide (EDC) (10 μL of a 1M solution in anhydrous. DMSO) followed by 75 equivalents of N-hydroxysuccinimide (15 μL of a 1000 mM solution in anhydrous DMSO), the reaction was brought to an intermediate volume of 180 μL with anhydrous DMSO and shaken for 48 hours. One molar equivalent (20 ml) of fluorescein derivative with a free primary amine was then added and the reaction was incubated with vortexing for 24 hr. Reaction progress was followed by RP-TLC using $H_2O$ as the developing media. Upon completion of the reaction, fluorescent products were purified by normal phase silica TLC and eluted as described above, except that 9:1 acetonitrile/2 mM NH4OAc, pH 5.5 was used as the TLC solvent and 8:2 acetonitrile/2 mM NH4OAc, pH 5.5 was used for elution.

A total of 16 unique combinations of activated PAP and fluorescein molecules were reacted and from these, more than 40 fluorescent products were isolated and tested for binding to antibodies. This approach can be viewed as sort of a "poor man's combinatorial chemistry," applicants have found it to be very successful for development of FP tracers in other instances. It is noted that the homogenous nature of FP assays and the availability of multiwell instruments makes the screening efforts relatively rapid.

Results of Ab-Tracer Interaction Studies

Initial screens for Ab-tracer binding were done by adding several concentrations of each antibody to 1 nm tracer in multiwell plates and monitoring for increases in tracer polarization. With all of the antibodies, purification of IgG fractions using immobilized Protein A or Protein G was required to remove non-specific binding components. All of the data shown is using antibodies purified on Protein G (Pierce Nab™ Protein G Spin Chromatography Kit). Tracer/Ab combinations that showed an interaction in the initial screen were analyzed in more detail for competitive displacement by PAP and selectivity of PAP over PAPS. A total of nine purified antibodies (3 antigens×3 rabbits) were tested for binding with 44 different fluorescein-labeled PAP tracers. All assays were done in black 96-well plates or black low-volume 384-well plates, which gave essentially identical results. Polarization values were read on a Tecan Ultra with a fluorescein filter set (excitation at 485 nm to emission at 535 nm) ($Ex_{485}/Em_{535}$).

Figure 19:
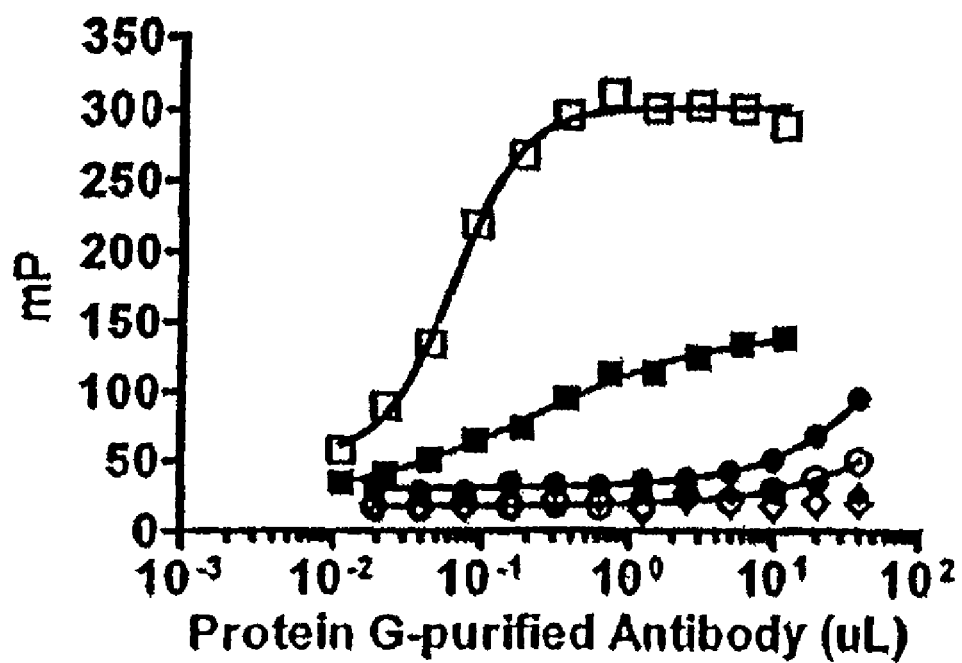
FIG. 19 shows binding isotherms for anti-PAP antibodies and PAP-fluorescein tracers.

It is noted that the binding isotherms in FIG. 19 were generated using the three antibodies and two tracers shown in Table 3 below, and are representative of experiments used to screen antibodies and tracers for binding. Shown are the N6-PAP-F8 tracer binding to Abs 1781 ○, 1810 ◇, and 3642□, and C8-PAP-F14 tracer with the same antibodies: 1781 ●, 1810 ◆, 3642 ■. Antibodies were serially diluted two-fold in 50 mM phosphate buffer (pH 7.4) containing 150 mM NaCl, 0.1 mg/mL BGG, and 1 nM tracer in a total volume of 100 uL in a 96-well plate or 12 ul in 384-well plates (results in the two plates are identical) and polarization values were read on the Tecan Ultra after one hour incubation at room temperature.

TABLE 3

Representative antibodies and tracers

| Abbreviation | Description |
|---|---|
| Ab 1781 | 8-azido-PAP-BSA immunogen |
| Ab 1810 | 2-azido-PAP-BSA immunogen |
| Ab 3642 | N6-aminohexyl-PAP-KLH immunogen |
| N6-PAP-F8 | N6-aminohexyl-PAP conjugated to 6-carboxyfluorescein succinimidyl ester |
| C8-PAP-F14 | C8-aminohexyl-PAP conjugated to 6-carboxyfluorescein succinimidyl ester |

The binding properties of antibodies generated from the same immunogen in different animals were similar, but not identical. In this experiment, the 3642 antibody bound both tracers significantly tighter than 1781, and 1810 did not bind either tracer even at the highest concentration tested. The maximal polarization values for 3642 binding to N6-PAP-F8 and C8-PAP-F14 were 140 and 300 mP, respectively; unbound tracer polarization was approximately 20 mP, so the shift observed is more than adequate for use in an FPIA. To test whether binding is specific, competitive displacement by PAP was assessed.

Figure 20:
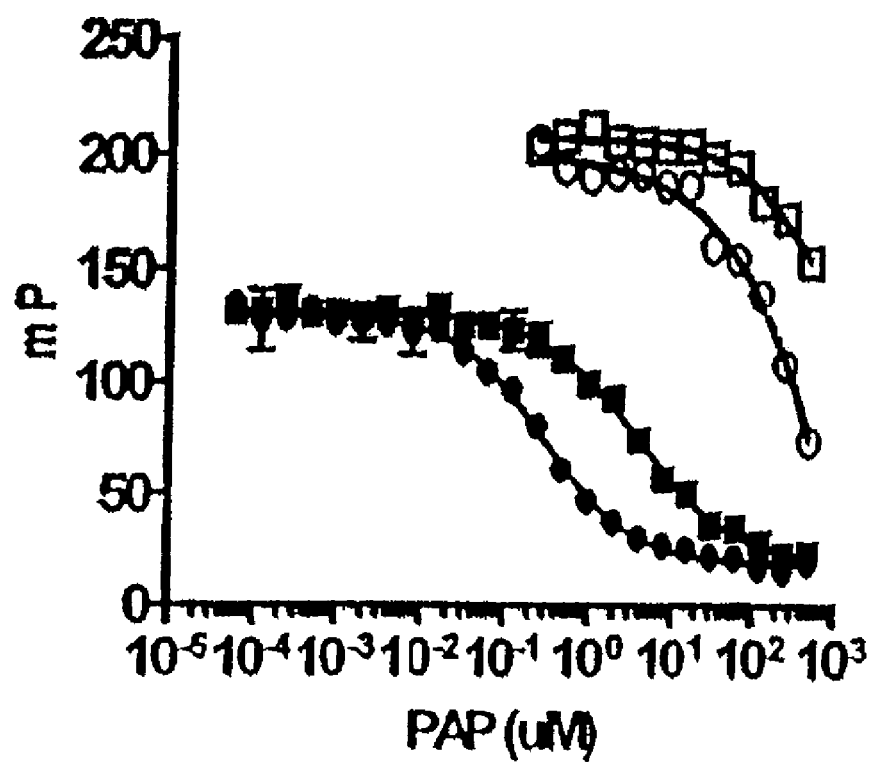
FIG. 20 shows competitive displacement of two different tracers from Ab 3642 by PAP and PAPS.

FIG. 20 shows PAP and PAPS competition curves for A δ 3642 and the same two tracers, PAP and PAPS. N6-PAP-6F8 tracer is represented by the open symbols: ○ (PAP), □ (PAPS). C8-PAP-F14 tracer is represented with the closed symbols: ● (PAP), ■ (PAPS). PAP or PAPS was serially diluted two-fold in black mutiwell plates containing 50 mM phosphate buffer (pH 7.4), 150 mM NaCl, 0.1 mg/mL BGG, 1 nM C8-PAP-F14, and 1.5 uL purified Ab 3642 in a total volume of 12 μl or 1 nM N6-PAP-F8 and 0.5 uL 3642 Ab in a 20 uL volume. Polarization values were read after one hour at room temperature.

The $IC_{50}$ for PAP with the C8-PAP-F14 tracer is 300 nM, low enough to allow use of these reagents for monitoring SULT1E1 activity. Note that a much higher concentration of PAP (and PAPS) is required to compete off the tighter binding N6-PAP-F8 tracer. This may be because in this case the tracer has the same linker group as the immunogen used to generate antibody, and a population of antibody is recognizing the linker, making the tracer more difficult to displace with free PAP. FIG. 20 also shows that PAPS is less effective than PAP at displacing the tracers from Ab 3642.

Figure 21:
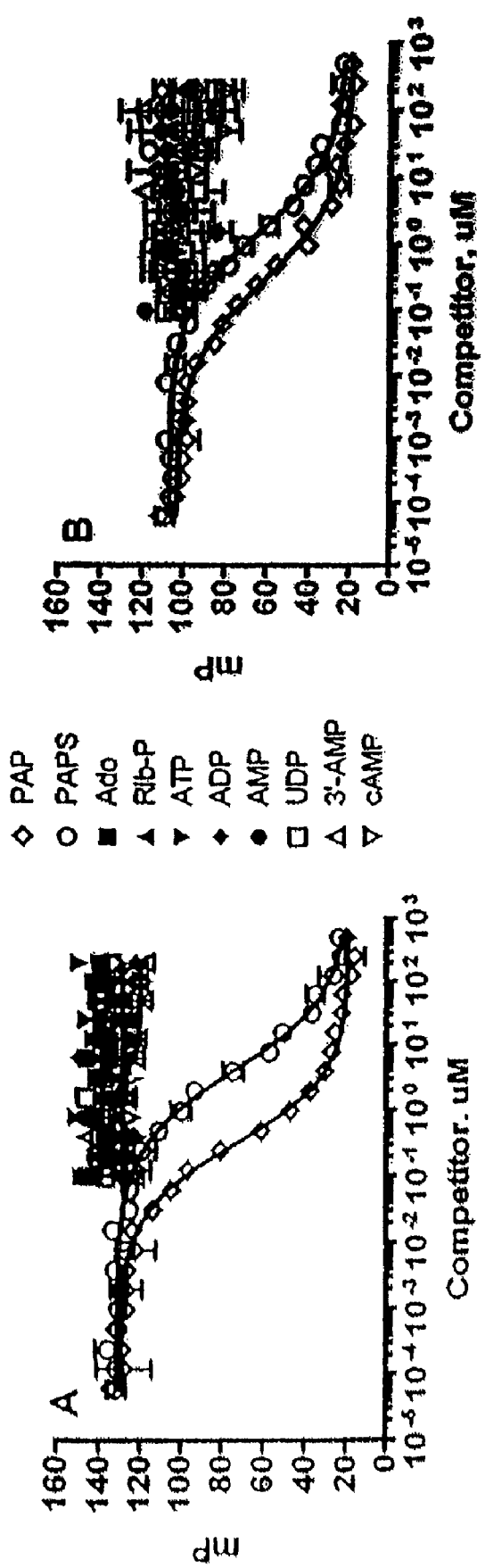
FIGS. 21 A-B show the competition curves with two Anti-PAP antibody/Tracer combinations.

Similar results were observed with the 1781 Ab as shown in FIG. 21, which includes complete curves for PAP, PAPS and several similar molecules in competition experiments with the C8-PAP-F14 tracer. FIG. 21 shows competition curves with two anti-PAP antibody/tracer combinations. Competitors were serially diluted two-fold in a black 384-well microtiter plate containing 50 mM phosphate buffer (pH 7.4), 150 mM NaCl, 0.1 mg/mL BGG, 1 nM Tracer C8-PAP-F14, and either 1.5 uL Ab 3642 (A) or 3 uL Ab 1781 (B) in a total volume of 12 uL. After one hour incubation at room temperature, the polarization values were read on a Tecan Ultra ($Ex_{485}/Em_{535}$). The mean and standard deviation of duplicates for all data sets are shown. The $IC_{50}$ values for PAP and PAPS with the 3641/tracer and 1781/tracer combinations were 0.3 uM PAP, 3.8 uM PAPS; and 0.3 uM PAP, 1.5 uM PAPS, respectively.

The 1781 and 3642 antibodies exhibited a 5- and 13-fold selectivity for PAP over PAPS respectively, and much higher selectivity for PAP over all of the other nucleotides tested. The cross reaction with PAPS is higher than expected given the lack of cross reaction with other adenine nucleotides. In this regard, it should be noted that most commercial PAPS preparations contain a significant fraction of PAP, but applicants purchased HPLC-purified preparations that were analyzed at greater than 95% purity, and took precautions in its storage and use to prevent hydrolysis. In any event, these results clearly show that applicants can generate antibodies that bind selectively to PAP in the presence of PAPS, which is a key feasibility issue for allowing sufficient signal:noise and dynamic range in the proposed SULT assay.

The results observed with other antibodies and tracers tested were similar. The additional antibodies produced from the N6-aminohexyl-PAP-KLH and 8-azido-PAP-BSA immunogens bound many of the tracers and the Ab/tracer complexes could be displaced in all cases by unlabeled PAP, indicating that the interaction was specific. The 1810 antibodies showed very poor or no tracer binding and were not tested further. The polarization of the free tracers ranged from 15-40 mP and increases observed upon Ab binding ranged from less than 100 mP to almost 300 mP. Interaction with some tracers was too weak to allow saturation with Ab, so maximal polarization changes were not always observed. More than ⅔ of the tracers tested bound to both types of Ab, but none of the tracers synthesized from N6-carboxymethyl-PAP bound to antibodies generated from either immunogen.

The FPIA-Based SULT Assay

Though applicants will need to produce an antibody that differentiates between PAP and PAPS more effectively to develop a high quality assay, applicants were able to use the 3642 Ab and C8-PAP-F14 tracer to monitor detection of PAP produced in reactions containing the purified SULT1E1-cHis. In the initial experiment applicants sought to identify the optimal PAPS concentration for maximal signal:noise. SULT1E1-cHis was incubated with estradiol and varying concentrations of PAPS in the presence of pre-formed Ab-tracer complex; SULT1E1 was present at a level sufficient to rapidly drive the reactions to completion (FIG. 22).

Figure 22:
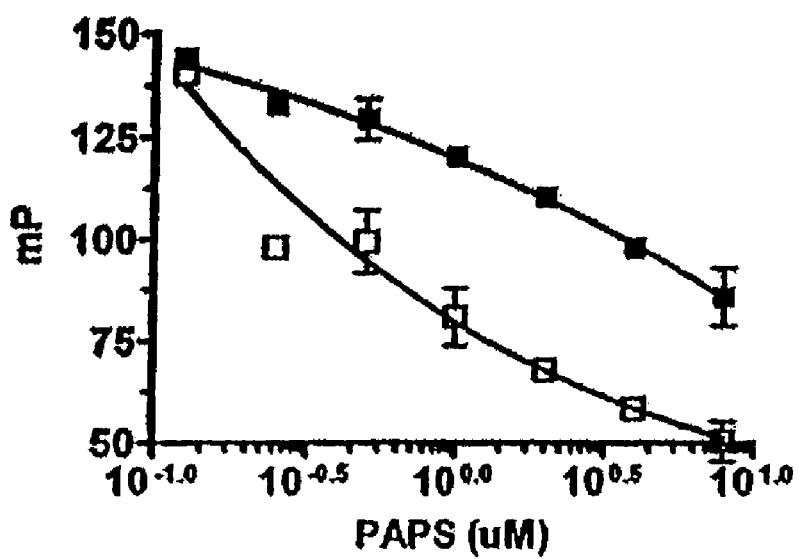
FIG. 22 shows the effect of PAPS concentration on detection of enzymatically generated PAP.

FIG. 22 illustrates the effect of PAPS concentration on detection of enzymatically generated PAP. The assay mixture included 200 ng of SULT1E1-6×His (□) or assay buffer (■) was added to wells containing 30 mM phosphate (pH 7.4), 7 mM DTT, 8 mM $MgCl_2$, 75 mM NaCl, 0.5 mg/mL BGG, 150 nM estradiol, 1 nM C8-PAP-F14 tracer, 12.5 uL Ab 3642, and varying concentrations of PAPS in a total assay volume of 100 μL. The plate was incubated for 24 hour at 37° C. and read in a Tecan Ultra ($Ex_{485}/Em_{535}$).

As in a typical FPIA, the tracer was used at a concentration well below the $K_d$ and the Ab was adjusted to a concentration that resulted in approximately 85% of maximal tracer polarization in the absence of competitor. FIG. 22 shows that there is a range of PAPS concentrations—from approximately 1 to 5 mM—where the enzymatically produced PAP causes a decrease in tracer polarization of approximately 40 mP (the difference between the open and solid squares in FIG. 22).

That is, even though this antibody cross-reacts with PAPS significantly, it can be used in a competitive FPIA mode to detect PAP produced in a SULT reaction with saturating PAPS ($K_m$ for PAPS with SULT1E1 is approximately 50 nM) with a dynamic range of 40 mP. Moreover, these were homogenous reactions, or single addition reactions, in which all of the reaction and detection components were added at the start of the reaction, which is the preferred approach for an HTS assay. Similar results are attained if the detection reagents are added after the enzymatic reaction is complete, thus the polarization signal is not affected by the enzymatic reaction (data not shown).

Figure 23:
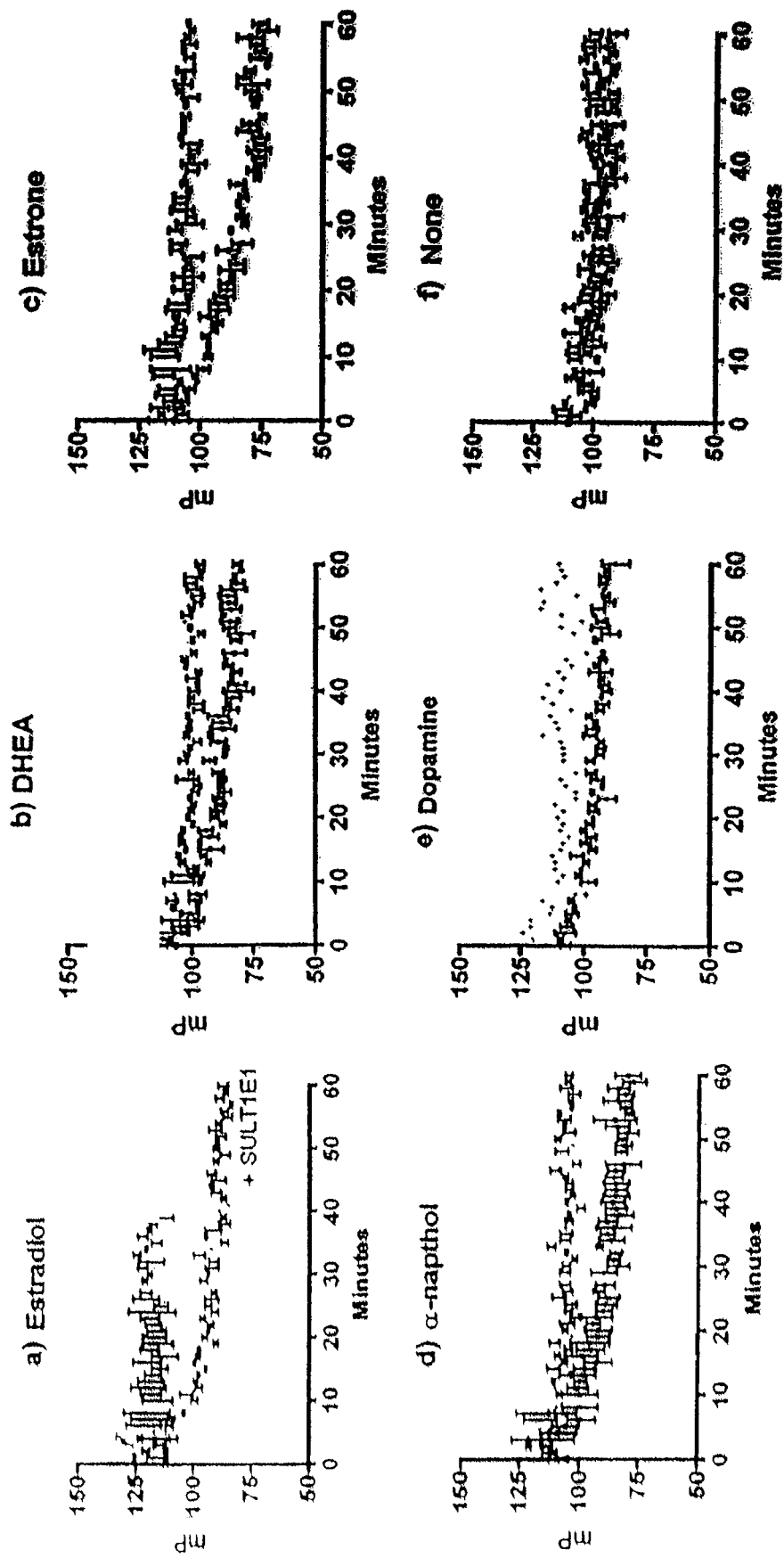
FIGS. 23 A-F show a continuous FPIA-based detection of SULT activity with diverse substrates.

Described above is an embodiment of how one of the Ab/tracer pairs applicants produced was used for detection of PAP in SULT reactions that are allowed to proceed to completion before reading. However, a continuous assay is the most desirable format for HTS because it allows accurate enzyme rate determinations and precludes the need for a quench step. FIG. 23 shows that the 3642 Ab and C8-PAP-F14 tracer can be used to continuously monitor SULT1E1 enzyme activity over time, allowing determination of enzyme rates with diverse substrates.

FIG. 23 provides graphs of continuous FPIA-based detection of SULT activity with diverse substrates. acceptor substrates (200 nM) were added to wells containing 30 mM phosphate (pH 7.4), 7 mM DTT, 0.8 mM $MgCl_2$, 75 mM NaCl, 0.5 mg/mL BGG, 2 uM PAPS, 200 ng SULT1E1-cHis, 1 nM C8-PAP-F14 Tracer, and 12.5 uL Ab 3642 in a total volume of 100 uL. Control reactions (top trace in each graph) lacked C-His-SULT1E1 and contained all other reaction components. The plate was incubated at room temp and polarization read at 1 minute intervals.

The top trace in each graph is a control reaction lacking SULT1E1, thus polarization does not change significantly, whereas in the reactions containing enzyme it decreases with time. The experimental setup was very similar to what might be done in an HTS setting: antibody and tracer were put into the SULT reaction mix, dispensed into a 384 well plate containing different acceptor substrates, and the reactions were started by the addition of SULT1E1-cHis. The plates were then read at regular intervals and polarization values plotted as a function of time. In reactions with known SULT substrates, the polarization decreased over time relative to control reactions lacking enzyme; as may be expected as enzymatically produced PAP displaces the tracer from Ab. Note that there is no significant change in polarization when no acceptor substrate is present (graph f) or if SULT1E1 is absent (top trace in each graph), indicating that the PAPS molecule is sufficiently resistant to non-productive chemical or enzymatic hydrolysis.

Figure 24:
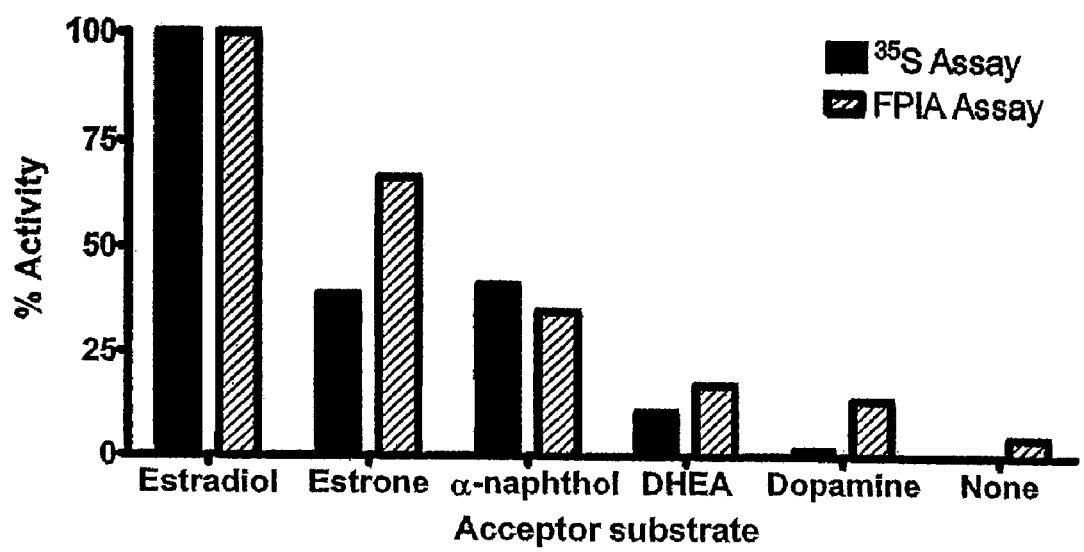
FIG. 24 shows a comparison of SULT1E1 acceptor substrate profiles determined using the FPIA-based assay and the $^{35}$S-PAPS radioassay.

These results show that a generic, fluorescence-based activity assay for sulfotransferases is technically feasible. In these experiments, the cross reaction of the 3642 Ab with PAPS contributes significant background (i.e., decrease in polarization), limiting the dynamic range of the assay, but enzymatic rates can still be obtained from the linear portions of the velocity curves. The bar graph in FIG. 24 shows rates for each substrate calculated from linear portions of the velocity curves in FIG. 23; though not a precise assay at this point, this rank-ordering of substrates does correlate inversely with their published $K_m$ values and with the substrate profile that applicants determined using purified SULT1E1 and the $^{35}$S-PAPS radioassay (FIG. 24). Accordingly, FIG. 24 is a comparison of SULT1E1 acceptor substrate profiles determined using the FPIA-based assay and the $^{35}$S-PAPS radioassay. Rates of FPIA-based reactions were calculated from linear portions of curves shown in FIG. 23. Acceptor substrates were used at 200 nM (FPIA) or 400 nM ($^{35}$S-radioassay).

Figure 25:
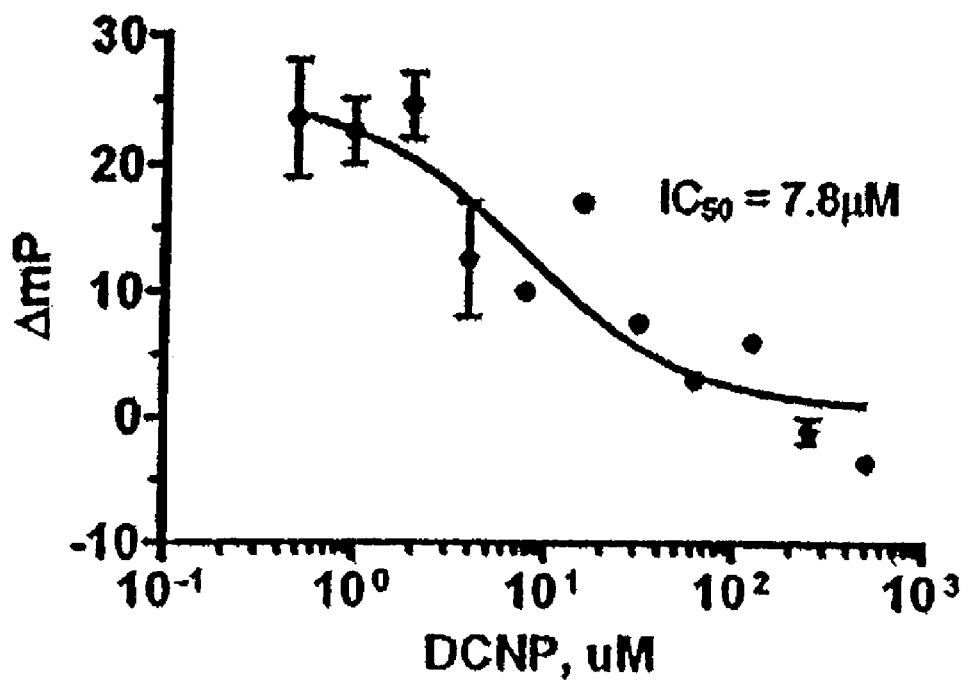
FIG. 25 shows inhibition of SULT1E1 by 2,6 Dichloro-4-nitrophenol (DCNP) measured with the FPIA-based assay.

Lastly, applicants used a known SULT inhibitor, DCNP, to show that the FPIA-based assay could be used to generate an inhibition curve (FIG. 25). Specifically, FIG. 25 is a graph showing inhibition of SULT1E1 by 2,6 Dichloro-4-nitrophenol (DCNP) measured with the FPIA-based assay. DCNP was serially diluted two-fold into wells in 46 uL of phosphate assay buffer (30 mM $KPO_4$ (pH 6.5), 0.5 mg/mL BGG, 15 mM DTT, 1.6 mM $MgCl_2$, 4 µM PAPS), followed by 50 µl of a 2× Antibody/tracer mix (5 uL 3642 Ab/2 nM Tracer C8-PAP-F14), and 200 ng of SULT1E in a total volume of 100 µl. The plate was incubated at room temp for 30 min, and read on the Tecan Ultra. AmP values were calculated by subtracting the SULT1E reactions from the no SULT1E controls. All values represent the mean of replicates.

The response of the FPIA assay to DCNP was validated by comparison with the $^{35}$S-radioassay (data not shown); the $K_i$ values determined with the two assay methods were 7.8 mM and 11 mM, respectively. Thus applicants have demonstrated that the assay can be used for detection of substrates and inhibitors—both of the key intended HTS applications.

Taken together, these results clearly establish feasibility for producing all of the components of the proposed FPIA based SULT assay: purified recombinant SULTs, antibody that selectively recognizes PAP in the presence of PAPS, and fluorescent PAP tracers whose binding and competitive displacement from Ab can be detected by significant changes in polarization. In addition, applicants were able to demonstrate that the assay reagents could be used to detect SULT activity in a continuous mode, very similar to how the assay may be used in an HTS setting, that the response to different substrates is similar to the standard radioassay, and that the assay can be used for detection of an inhibitor.

Accordingly, it is envisioned that an antibody, suitably a monoclonal antibody with approximately 10-fold greater affinity and selectivity for PAP will be produced that will enable development of an assay with suitable dynamic range and signal:noise for commercial HTS applications.

Example 6

Assay Systems

Although, the methods described herein may be utilized in a variety of different assay systems, in its simplest form, the present assay system comprises an assay receptacle in which the assayed reaction is carried out, and a detector for detecting the results of that reaction. In preferred aspects, the assay receptacle is selected from a test tube, a well in a multiwell plate, or other similar reaction vessel. In such cases, the various reagents are introduced into the receptacle and typically assayed in the receptacle using an appropriate detection system, described above such as a fluorescence polarization detector. In addition to a receptacle, a flat surface such as glass or plastic could also be used and the reaction components spotted onto the surface in a defined array (such as a microarray).

Alternatively, and equally preferred is where the reaction receptacle comprises a fluidic channel, and preferably, a microfluidic channel. As used herein, the term microfluidic refers to a channel or other conduit that has at least one cross-sectional dimension in the range of from about 1 micron to about 500 micron. Examples of microfluidic devices useful for practicing the methods described herein include, e.g., those described in e.g., U.S. Pat. Nos. 5,942,443, 5,779,868, and International Patent Application No. WO 98/46438, the disclosures of which are incorporated herein by reference.

In accordance with the above-described methods, it is envisioned that an enzyme mediated coupling reaction between a first and second reactant may be carried out in channels of a microfluidic device. As such, by using a microfluidics platform, it may be possible to mimic the compartmentalization of a eukaryotic cell. This method could then be used to monitor the activity of group transfer reactions catalyzed by enzymes in a more native environment, in the context of other proteins and with cellular components that may affect enzymatic activity. Therefore, data on the activity of enzymes that catalyze group transfer reactions and the consequences of their inhibition can be obtained in a setting that will more accurately reflect an in vivo environment.

It is envisioned that these assay systems may be capable of screening test compounds that affect enzymatic reaction of interest. Optionally, devices used in accordance with the present invention are configured to operate in a high-throughput screening format, e.g., as described in U.S. Pat. No. 5,942,443. In particular, instead of delivering potential test compounds to the reaction zone from a reservoir integrated into the body of the device, such test compounds are introduced into the reaction zone via an external sampling pipettor or capillary that is attached to the body of the device and fluidly coupled to the reaction zone. Such pipettor systems are described in, e.g., U.S. Pat. No. 5,779,868 (fully incorporated by reference). The sampling Pipettor is serially dipped into different sources of test compounds which are separately and serially brought into the reaction zone to ascertain their affect, if any, on the reaction of interest.

Movement of materials through the channels of these microfluidic channel networks is typically carried out using any of a variety of known techniques, including electrokinetic material movement (e.g., as described in U.S. Pat. No., 5,858,195 (fully incorporated by reference), pressure based flow, axial flow, gravity flow, or hybrids of any of these.

Example 7

Assay Kit

Another embodiment of the invention is a kit for detecting and quantifying a donor product of a group transfer reaction or a catalytic activity generating the donor-product of a group transfer reaction. The general equation for the group transfer reaction includes a donor-X+acceptor→donor-product+acceptor-X, wherein the donor-product is detected by the general detection reaction: first complex+donor-product→second complex+displaced detectable tag. In its most simplest form, the kit for an FPIA immunoassay may include a macromolecule (i.e., antibody or an inactivated enzyme) and a tracer (displaced) and optionally the specific group transfer enzyme of interest. It is noted that the macromolecule and the tracer may either be separate or incorporated into one solution vessel.

The kit may also include components such as, an activated donor, a detectable tag, acceptor substrates, inhibitors, buffers, cofactors, stabilizing agents, a set of instructions for using the kit, or packaging and any combination thereof. In addition, the kit may be formatted for multiplex detection by using more than one antibody/detectable tag pair where the detectable tags can be differentiated on the basis of the observables they produce. The immunoassay may be used to detect the donor product or the catalytic activity generating the donor product.

In practicing the invention, it is encompassed that the kit may be used for screening a library for a molecule or a set of molecules, capable of contacting an enzyme, wherein the enzyme generates the donor-product in a group transfer reaction. The library may include at least one of a plurality of chemical molecules, a plurality of nucleic acids, a plurality of peptides, or a plurality of proteins, and a combination thereof; wherein the screening is performed by a high-throughput screening technique using a multi-well plate or a microfluidic system.

It is further envisioned that the macromolecule in the kit includes at least one of an antibody, a polypeptide, a protein, a nucleic acid molecule, an inactivated enzyme, and a combination thereof that is capable of contacting the donor-product with high affinity. It is further envisioned that the kit optionally include at least one of the following enzyme classes: sulfotransferases, kinases, UDP-glucuronosyl transferases, methyl transferases, acetyl transferases, glutathione transferases, ADP-ribosyltransferases, ATPases, GTPases, or a combination thereof.

Although FPIA is a suitable mode of detection, also encompassed within the scope of the invention are kits designed to be used for detecting donor product or the catalytic activity generating the donor product through other means such as a homogeneous assay, a homogeneous fluorescence intensity immunoassay, a homogeneous fluorescence lifetime immunoassay, a homogeneous fluorescence resonance energy transfer (FRET) immunoassay or a homogenous chemiluminescent immunoassay, or a non-homogenous assay such as enzyme-linked immunoassay (ELISA). In the case of a homogeneous fluorescence intensity immunoassay or a homogeneous fluorescence lifetime immunoassay, the kit could be composed of an antibody and fluorescent detectable tag where the intensity and/or lifetime of the detectable tag is different when it is bound to antibody and than it is free in solution. The difference in fluorescence; i.e., the assay signal, could be enhanced by modification of the antibody such that its interaction with the detectable tag results in a further change in its fluorescence properties; i.e., quenching, enhancement, or a change in the lifetime. In the case of a homogenous FRET immunoassay, the interaction of a first fluor associated with the detectable tag with a second fluor that is attached to the antibody—either directly or via associated binding molecules such as biotin and streptavidin—could result in the excitation of the second fluor (or the reverse), thereby generating a fluorescence emission at a wavelength different from that of the detectable tag. The second fluor could be a small organic molecule or a luminescent lanthanide probe. (It is noted that lanthanide emission is not fluorescence and is referred to as luminescence-based resonance energy transfer, or LRET). In the case of chemiluminescent detection, the detectable tag could be the donor product bound to one fragment of an enzyme used for chemiluminescent detection such as β-galactosidase. When the donor product-fragment-one complex is displaced from antibody by the donor product, it would then bind to fragment two of the enzyme, producing an intact, active enzyme that would be capable of producing a chemiluminescent signal with an appropriate substrate. In the case of an ELISA, the assay would not be homogenous, and would require donor product or antibody be immobilized to the surface of multiwell plates. A secondary antibody conjugated to a detection enzyme would also be included in this format.

All publications cited herein are hereby incorporated by reference in their entirety. In the case of conflict between the present disclosure and the incorporated publications, the present disclosure should control.

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

REFERENCES

Adamia, S., C. A. Maxwell, et al. (2005). "Hyaluronan and hyaluronan synthases: potential therapeutic targets in cancer." *Curr Drug Targets Cardiovasc Haematol Disord* 5(1): 3-14.

Adjei, A. A., B. A. Thomae, et al. (2003). "Human estrogen sulfotransferase (SULT1E1) pharmacogenomics: gene resequencing and functional genomics." *Br J Pharmacol* 139(8): 1373-82.

Adjei, A. A. and R. M. Weinshilboum (2002). "Catecholestrogen sulfation: possible role in carcinogenesis." *Biochem Biophys Res Commun* 292(2): 402-8.

Allison Miller-Wing, E. G., Barbara Armstrong, Lindsey Yeats, Ram Bhatt, Frank Gonzales, and Steven Gessert. (2003). "Polaris Protein Kinase Assays: Homgenous, Chemistry-based Fluorescence Polarization Detection Method for Primary Screening of Protein Kinase Inhibitors." *SBS 9th Annual Conference and Exhibition*, Portland, Oreg.

Breitling, F., Dubel, S. (1999). *Recombinant Antibodies*, Wiley-Liss.

Brodelius, P., P. O. Larsson, et al. (1974). "The synthesis of three AMP-analogues: N6-(6-aminohexyl)-adenosine 5'-monophosphate, N6-(6-aminohexyl)-adenosine 2',5'-bisphosphate, and N6-(6-aminohexyl)-adenosine 3',5'-bisphosphate and their application as general ligands in biospecific affinity chromatography." *Eur J Biochem* 47(1): 81-9.

Broudy, M. C., C L; Patten, C J "Fluorometirc High Throughput Inhibition Assay for Human UDP Glucuronosyltransferase 1A1" http://www.bdbiosciences.com/discovery_labware/gentest/products/pdf/S01T044R2.pdf.

Brune, M., J. L. Hunter, et al. (1994). "Direct, real-time measurement of rapid inorganic phosphate release using a novel fluorescent probe and its application to actomyosin subfragment 1 ATPase." *Biochemistry* 33(27): 8262-71.

Burkart, M. D. and C. H. Wong (1999). "A continuous assay for the spectrophotometric analysis of sulfotransferases using aryl sulfotransferase IV." *Anal Biochem* 274(1): 131-7.

Butters, T. D., H. R. Mellor, et al. (2003). "Small-molecule therapeutics for the treatment of glycolipid lysosomal storage disorders." *Philos Trans R Soc Lond B Biol Sci* 358 (1433): 927-45.

Camaioni, E., J. L. Boyer, et al. (1998). "Deoxyadenosine bisphosphate derivatives as potent antagonists at P2Y1 receptors." *J Med Chem* 41(2): 183-90.

Carlini, E. J., R. B. Raftogianis, et al. (2001). "Sulfation pharmacogenetics: SULT1A1 and SULT1A2 allele frequencies in Caucasian, Chinese and African-American subjects." *Pharmacogenetics* 11(1): 57-68.

Checovich, W. J., R. E. Bolger, et al. (1995). "Fluorescence polarization—a new tool for cell and molecular biology." *Nature* 375(6528): 254-6.

Chene, P. (2002). "ATPases as drug targets: learning from their structure." *Nat Rev Drug Discov* 1(9): 665-73.

Chemite, G. S, and J. R. Pasqualini (2001). "The selective estrogen enzyme modulator (SEEM) in breast cancer." *J Steroid Biochem Mol Biol* 76(1-5): 95-104.

Cohen, P. (2000). "The regulation of protein function by multisite phosphorylation—a 25 year update." *Trends Biochem Sci* 25(12): 596-601.

Cohen, P. (2002). "Protein kinases—the major drug targets of the twenty-first century?" *Nat Rev Drug Discov* 1(4): 309-15.

Coughtrie, M. W. and L. E. Johnston (2001). "Interactions between dietary chemicals and human sulfotransferases-molecular mechanisms and clinical significance." *Drug Metab Dispos* 29(4 Pt 2): 522-8.

Crabbe, P., C. Van Peteghem, et al. (2000). "Influence of the hapten conjugation site on the characteristics of antibodies generated against metabolites of clostebol acetate." *J Agric Food Chem* 48(8): 3633-8.

Dancey, J. and E. A. Sausville (2003). "Issues and progress with protein kinase inhibitors for cancer treatment." *Nat Rev Drug Discov* 2(4): 296-313.

DeBonis, S., D. A. Skoufias, et al. (2004). "In vitro screening for inhibitors of the human mitotic kinesin Eg5 with antimitotic and antitumor activities." *Mol Cancer Ther* 3(9): 1079-90.

Deng, C. and R. R. Chen (2004). "A pH-sensitive assay for galactosyltransferase." *Anal Biochem* 330(2): 219-26.

Dwek, M. V. and S. A. Brooks (2004). "Harnessing changes in cellular glycosylation in new cancer treatment strategies." *Curr Cancer Drug Targets* 4(5): 425-42.

Eglen, R. M. and R. Singh (2003). "Beta galactosidase enzyme fragment complementation as a novel technology for high throughput screening." *Comb Chem High Throughput Screen* 6(4): 381-7.

Ethell, B. T., G. D. Anderson, et al. (1998). "A universal radiochemical high-performance liquid chromatographic assay for the determination of UDP-glucuronosyltransferase activity." *Anal Biochem* 255(1): 142-7.

Evans, W. E. R., M. V. (1999). *Science* 286: 487-491.

Falany, C. N. (1997). "Enzymology of human cytosolic sulfotransferases." *Faseb J* 11(4): 206-16.

Foldes, A. and J. L. Meek (1973). "Rat brain phenolsulfotransferase: partial purification and some properties." *Biochim Biophys Acta* 327(2): 365-74.

Fowler, A., D. Swift, et al. (2002). "An evaluation of fluorescence polarization and lifetime discriminated polarization for high throughput screening of serine/threonine kinases." *Anal Biochem* 308(2): 223-31.

Frame, L. T., S. Ozawa, et al. (2000). "A simple colorimetric assay for phenotyping the major human thermostable phenol sulfotransferase (SULT1A1) using platelet cytosols." *Drug Metab Dispos* 28(9): 1063-8.

Freimuth, R. R., B. Eckloff, et al. (2001). "Human sulfotransferase SULT1C1 pharmacogenetics: gene resequencing and functional genomic studies." *Pharmacogenetics* 11(9): 747-56.

Funk, C. J., A. S. Davis, et al. (2004). "Development of high-throughput screens for discovery of kinesin adenosine triphosphatase modulators." *Anal Biochem* 329(1): 68-76.

Fuster, M. M. and J. D. Esko (2005). "The sweet and sour of cancer: glycans as novel therapeutic targets." *Nat Rev Cancer* 5(7): 526-42.

Glatt, H. (2000). "Sulfotransferases in the bioactivation of xenobiotics." *Chem Biol Interact* 129(1-2): 141-70.

Guo, H. B., I. Lee, et al. (2002). "Aberrant N-glycosylation of beta1 integrin causes reduced alpha5beta1 integrin clustering and stimulates cell migration." *Cancer Res* 62(23): 6837-45.

Hanks, S. K. (2003). "Genomic analysis of the eukaryotic protein kinase superfamily: a perspective." *Genome Biol* 4(5): 111.

Harlow, E. L., D. (1999). *Using Antibodies: A Laboratory Manual*, Cold Spring Harbor Press.

Hemmerich, S., D. Verdugo, et al. (2004). "Strategies for drug discovery by targeting sulfation pathways." *Drug Discov Today* 9(22): 967-75.

High Tech Business Decisions, M., CA (2002). "High-Throughput Screening 2002: New Strategies and Technologies." *Commisioned Market Analysis*.

Horton, J. K., R. C. Martin, et al. (1992). "Enzyme immunoassays for the estimation of adenosine 3',5' cyclic monophosphate and guanosine 3',5' cyclic monophosphate in biological fluids." *J Immunol Methods* 155(1): 31-40.

Ishiguro, H., T. Shimokawa, et al. (2002). "Isolation of HELAD1, a novel human helicase gene up-regulated in colorectal carcinomas." *Oncogene* 21(41): 6387-94.

Kiang, T. K., M. H. Ensom, et al. (2005). "UDP-glucuronosyltransferases and clinical drug-drug interactions." *Pharmacol Ther* 106(1): 97-132.

Kim, J., S. Felts, et al. (2004). "Development of a fluorescence polarization assay for the molecular chaperone Hsp90." *J Biomol Screen* 9(5): 375-81.

Kimple, R. J., M. B. Jones, et al. (2003). "Established and emerging fluorescence-based assays for G-protein function: heterotrimeric G-protein alpha subunits and regulator of G-protein signaling (RGS) proteins." *Comb Chem High Throughput Screen* 6(4): 399-407.

Kostich, M., J. English, et al. (2002). "Human members of the eukaryotic protein kinase family." *Genome Biol* 3(9): RESEARCH0043.

Kupcho, K., R. Somberg, et al. (2003). "A homogeneous, nonradioactive high-throughput fluorogenic protein kinase assay." *Anal Biochem* 317(2): 210-7.

Lindberg, M. and K. Mosbach (1975). "Preparation of analogues of ATP, ADP and AMP suitable for binding to matrices and the enzymic interconversion of ATP and ADP in solid phase." *Eur J Biochem* 53(2): 481-6.

Mallari, R., E. Swearingen, et al. (2003). "A generic high-throughput screening assay for kinases: protein kinase a as an example." *J Biomol Screen* 8(2): 198-204.

Manning, G., D. B. Whyte, et al. (2002). "The protein kinase complement of the human genome." *Science* 298(5600): 1912-34.

McCudden, C. R., M. D. Hains, et al. (2005). "G-protein signaling: back to the future." *Cell Mol Life Sci* 62(5): 551-77.

Merten, M., J. F. Dong, et al. (2001). "Cholesterol sulfate: a new adhesive molecule for platelets." *Circulation* 103(16): 2032-4.

Mulder, G. J. and A. B. van Doom (1975). "A rapid NAD+-linked assay for microsomal uridine diphosphate glucuronyltransferase of rat liver and some observations on substrate specificity of the enzyme." *Biochem J* 151(1): 131-40.

Nasir, M. S, and M. E. Jolley (1999). "Fluorescence polarization: an analytical tool for immunoassay and drug discovery." *Comb Chem High Throughput Screen* 2(4): 177-90.

Nowell, S., C. Sweeney, et al. (2002). "Association between sulfotransferase 1A1 genotype and survival of breast cancer patients receiving tamoxifen therapy." *J Natl Cancer Inst* 94(21): 1635-40.

Owicki, J. C. (2000). "Fluorescence polarization and anisotropy in high throughput screening: perspectives and primer." *J Biomol Screen* 5(5): 297-306.

Parker, G. J., T. L. Law, et al. (2000). "Development of high throughput screening assays using fluorescence polarization: nuclear receptor-ligand-binding and kinase/phosphatase assays." *J Biomol Screen* 5(2): 77-88.

Parkinson-A (2001). "Biotransformation of Xenobiotics." *Casaret & Doull's Toxicology Sixth Edition:* 133-224.

Pellegrini, F. and D. R. Budman (2005). "Review: tubulin function, action of antitubulin drugs, and new drug development." *Cancer Invest* 23(3): 264-73.

Plassart-Schiess, E. and E. E. Baulieu (2001). "Neurosteroids: recent findings." *Brain Res Brain Res Rev* 37(1-3): 133-40.

Raftogianis, R., C. Creveling, et al. (2000). "Estrogen metabolism by conjugation." *J Natl Cancer Inst Monogr* (27): 113-24.

Rojas, R. J., R. J. Kimple, et al. (2003). "Established and emerging fluorescence-based assays for 2G-protein function: Ras-superfamily GTPases." *Comb Chem High Throughput Screen* 6(4): 409-18.

Ross, H., C. G. Armstrong, et al. (2002). "A non-radioactive method for the assay of many serine/threonine-specific protein kinases." *Biochem J* 366(Pt 3): 977-81.

Rowlands, M. G., Y. M. Newbatt, et al. (2004). "High-throughput screening assay for inhibitors of heat-shock protein 90 ATPase activity." *Anal Biochem* 327(2): 176-83.

Schaffitzel, C., J. Hanes, et al. (1999). "Ribosome display: an in vitro method for selection and evolution of antibodies from libraries." *J Immunol Methods* 231(1-2): 119-35.

Scott, J. E. and J. W. Carpenter (2003). "A homogeneous assay of kinase activity that detects phosphopeptide using fluorescence polarization and zinc." *Anal Biochem* 316(1): 82-91.

Signorini, N., D. Molko, et al. (1998). "Polyclonal antibodies to adenine N1-oxide: characterization and use for the measurement of DNA damage." *Chem Res Toxicol* 11(10): 1169-75.

Sills, M. A., D. Weiss, et al. (2002). "Comparison of assay technologies for a tyrosine kinase assay generates different results in high throughput screening." *J Biomol Screen* 7(3): 191-214.

Simpson, M. A., C. M. Wilson, et al. (2002). "Inhibition of prostate tumor cell hyaluronan synthesis impairs subcutaneous growth and vascularization in immunocompromised mice." *Am J Pathol* 161(3): 849-57.

Song, C., R. A. Hiipakka, et al. (2001). "Auto-oxidized cholesterol sulfates are antagonistic ligands of liver X receptors: implications for the development and treatment of atherosclerosis." *Steroids* 66(6): 473-9.

Sridhar, R., O. Hanson-Painton, et al. (2000). "Protein kinases as therapeutic targets." *Pharm Res* 17(11): 1345-53.

Strott, C. A. (2002). "Sulfonation and molecular action." *Endocr Rev* 23(5): 703-32.

Thomae, B. A., B. W. Eckloff, et al. (2002). "Human sulfotransferase SULT2A1 pharmacogenetics: genotype-to-phenotype studies." *Pharmacogenomics J* 2(1): 48-56.

Thomae, B. A., O. F. Rifki, et al. (2003). "Human catecholamine sulfotransferase (SULT1A3) pharmacogenetics: functional genetic polymorphism." *J Neurochem* 87(4): 809-19.

Trubetskoy, O. V. and P. M. Shaw (1999). "A fluorescent assay amenable to measuring production of beta-D-glucuronides produced from recombinant UDP-glycosyl transferase enzymes." *Drug Metab Dispos* 27(5): 555-7.

Tukey, R. H. and C. P. Strassburg (2000). "Human UDP-glucuronosyltransferases: metabolism, expression, and disease." *Annu Rev Pharmacol Toxicol* 40: 581-616.

Walters, W. P. and M. Namchuk (2003). "Designing screens: how to make your hits a hit." *Nat Rev Drug Discov* 2(4): 259-66.

Willard, F. S., R. J. Kimple, et al. (2004). "Fluorescence-based assays for RGS box function." *Methods Enzymol* 389: 56-71.

Workman, P. (2003). "Overview: translating Hsp90 biology into Hsp90 drugs." *Curr Cancer Drug Targets* 3(5): 297-300.

Xie, Z. and J. Xie (2005). "The Na/K-ATPase-mediated signal transduction as a target for new drug development." *Front Biosci* 10: 3100-9.

Xu, K., A. S. Stem, et al. (2003). "A generic time-resolved fluorescence assay for serine/threonine kinase activity: application to Cdc7/Dbf4." *J Biochem Mol Biol* 36(4): 421-5.

Xue, Q., A. Wainright, et al. (2001). "Multiplexed enzyme assays in capillary electrophoretic single-use microfluidic devices." *Electrophoresis* 22(18): 4000-7.

Yabushita, H., M. Noguchi, et al. (2004). "Hyaluronan synthase expression in ovarian cancer." *Oncol Rep* 12(4): 739-43.

Zaman, G. J., A. Garritsen, et al. (2003). "Fluorescence assays for high-throughput screening of protein kinases." *Comb Chem High Throughput Screen* 6(4): 313-20.

Zawadzke, L. E., P. Wu, et al. (2003). "Targeting the MraY and MurG bacterial enzymes for antimicrobial therapeutic intervention." *Anal Biochem* 314(2): 243-52.

Zhang, B., D. Senator, et al. (2005). "Development of a high-throughput robotic fluorescence-based assay for HsEg5 inhibitor screening." *Anal Biochem* 345(2): 326-35.

We claim:

1. An isolated antibody produced against a donor product of an enzymatically catalyzed group transfer reaction, wherein the antibody has the ability to preferentially recognize a donor-product in the presence of a donor molecule, and wherein the antibody binds the donor-product, guanosine diphosphate (GDP) with at least ten-fold higher affinity than to the donor molecule, GTP.

2. The antibody of claim 1, wherein the antibody is generated using an immunogen made from a nucleotide conjugated to a carrier protein.

3. The antibody of claim 2, wherein the immunogen includes a linker region between the nucleotide and the carrier protein comprising a chemical formula of $NH_2$—X-Z, wherein X is a saturated or unsaturated chain of 2 to 20 carbons and Z is a functional group capable of covalently binding to a protein, and wherein the group includes an $NH_3$.

4. The antibody of claim 1, wherein the antibody binds the GDP, with at least fifty-fold higher affinity than to GTP.

5. The antibody of claim 1, wherein the antibody binds the GDP with at least one hundred-fold higher affinity than to GTP.

6. The antibody of claim 1, wherein the antibody binds the GDP with at least one hundred and thirty-fold higher affinity than to GTP.

7. A universal homogenous assay method for directly detecting a donor-product produced in a group transfer reaction in the presence of a donor molecule, the method comprising the steps of:
  a) reacting a donor molecule, which is guanosine triphosphate (GTP), with an acceptor in the presence of a catalytically active enzyme to form the donor-product, which is guanosine diphosphate (GDP), such that the GTP is partially consumed;
  b) combining the GDP produced in a group transfer reaction with a tracer and the antibody of claim 1 to provide a reaction mixture, the tracer comprising a nucleotide conjugated to a fluorophore, and capable of binding to the antibody to produce a detectable change in fluorescence polarization;
  c) measuring the fluorescence polarization of the mixture to obtain a measured fluorescence polarization; and
  d) comparing the measured fluorescence polarization with a characterized fluorescence polarization value corresponding to a known GDP concentration to directly detect the GDP produced in the group transfer reaction.

8. A method of using the assay of claim 7, for screening a chemical library to identify a molecule which is an acceptor substrate for an enzyme catalyzing a group transfer reaction or is capable of inhibiting or activating such an enzyme.

9. A universal homogenous assay method for directly detecting a donor-product produced in a group transfer reaction, the method comprising:
  a) reacting a donor molecule which is an guanosine triphosphate (GTP) with an acceptor, in the presence of a group transfer enzyme;
  b) forming the donor-product which is an guanosine diphosphate (GDP), such that the GTP is partially consumed;
  c) contacting the GDP with a first complex comprising an antibody that specifically recognizes the GDP and a tracer capable of producing an observable, wherein the antibody is the antibody of claim 1;
  d) competitively displacing the tracer of the first complex by the GDP, to generate a second complex, GDP-antibody complex and a displaced tracer, to directly detect the donor-product in the group transfer reaction; and
  e) detecting a change in the observable produced by the tracer in the first complex bound to the antibody and the displaced or free tracer.

10. A universal homogenous assay method for directly detecting a donor-product produced in a group transfer reaction, the method comprising the steps of:
  a) providing a reaction mixture having products of the group transfer reaction, a tracer and an antibody, wherein the products of the reaction include the donor-product, which is a guanosine diphosphate (GDP), in the presence of a donor molecule which is a guanosine triphosphate (GTP), wherein the antibody is the antibody of claim 1, and wherein the tracer comprises a nucleotide conjugated to a fluorophore and is capable of binding to the antibody to produce a detectable change in the fluorescence properties of the tracer;
  b) measuring the fluorescence properties of the reaction mixture to obtain a measured value; and
  c) comparing the measured fluorescence properties with a characterized fluorescence property value corresponding to a known GDP concentration to directly detect the GDP produced in the group transfer reaction.

11. An assay kit for detecting the donor-product of a group transfer reaction, the assay kit comprising
  an isolated antibody produced against a donor product of an enzymatically catalyzed group transfer reaction, wherein the antibody has the ability to preferentially recognize a donor-product in the presence of a donor molecule, and wherein the antibody binds the donor-product, guanosine diphosphate (GDP) with at least ten-fold higher affinity than to the donor molecule, GTP; and a tracer.

* * * * *